US010357554B2

(12) United States Patent
Dutta et al.

(10) Patent No.: US 10,357,554 B2
(45) Date of Patent: Jul. 23, 2019

(54) AMA-1 EPITOPES, ANTIBODIES, COMPOSITIONS, AND METHODS OF MAKING AND USING THE SAME

(71) Applicant: The United States of America, as represented by the Secretary of the Army, Washington, DC (US)

(72) Inventors: Sheetij Dutta, Silver Spring, MD (US); Adrian Batchelor, Hinckley, OH (US); Michael Foley, Fort Detrick, MD (US)

(73) Assignee: THE UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 0 days.

(21) Appl. No.: 15/035,914

(22) PCT Filed: Nov. 11, 2014

(86) PCT No.: PCT/US2014/064972
§ 371 (c)(1),
(2) Date: May 11, 2016

(87) PCT Pub. No.: WO2015/070207
PCT Pub. Date: May 14, 2015

(65) Prior Publication Data
US 2016/0279221 A1 Sep. 29, 2016

Related U.S. Application Data

(60) Provisional application No. 61/902,521, filed on Nov. 11, 2013, provisional application No. 61/921,031, filed on Dec. 26, 2013.

(51) Int. Cl.
| | | |
|---|---|---|
| A61K 39/00 | (2006.01) |
| A61K 39/395 | (2006.01) |
| A61K 39/015 | (2006.01) |
| C07K 16/20 | (2006.01) |
| C07K 14/445 | (2006.01) |
| A61K 38/00 | (2006.01) |

(52) U.S. Cl.
CPC .......... *A61K 39/015* (2013.01); *C07K 14/445* (2013.01); *C07K 16/205* (2013.01); *A61K 38/00* (2013.01); *A61K 2039/55566* (2013.01); *C07K 2317/34* (2013.01); *C07K 2317/565* (2013.01); *C07K 2317/76* (2013.01); *Y02A 50/412* (2018.01); *Y02A 50/58* (2018.01)

(58) Field of Classification Search
CPC .............................. A61K 39/00; A61K 39/395
USPC ............................................ 424/184.1, 185.1
See application file for complete search history.

(56) References Cited

U.S. PATENT DOCUMENTS

| 4,816,567 A | 3/1989 | Cabilly et al. |
| 5,422,109 A | 6/1995 | Brancq et al. |
| 7,029,685 B2* | 4/2006 | Lanar ...................... C12N 1/10 424/185.1 |
| 2003/0032787 A1* | 2/2003 | Lanar .................. C07K 14/445 536/23.1 |

FOREIGN PATENT DOCUMENTS

| WO | 96/02555 | 2/1996 |
| WO | 98/16247 | 4/1998 |
| WO | 98/56414 | 12/1998 |
| WO | 99/11241 | 3/1999 |
| WO | 99/12565 | 3/1999 |

OTHER PUBLICATIONS

Coley, A.M., et al. PLoS Pathogens, vol. 3, Issue 9, pp. 1308-1319, Sep. 2007.*
Thomas et al., Amer. J. Tropical Med. and Hygiene, vol. 51, No. 6, pp. 730-740, 1994.*
Abiola, A.W., Amer. J. Tropical Med. and Hygiene, vol. 85, No. 6, suppl. 1, pp. 358-359, Abstract 1192, 2011.*
Andagalu, B., et al., Amer. J. Tropical Med. and Hygiene, vol. 89, No. 5, suppl. 1, p. 258, Abstract 849, 2013.*
International Search Report dated May 18, 2015 for PCT Patent Application No. PCT/US2014/064972.
UniProt Q7KQK5, Apical Membrane Antigen 1, AMA1 (Oct. 16, 2013) [Retrieved from the internet Jan. 30, 2015; <http://www.uniprot.org/uniprot/Q7KQK5.txt?version=64>]; amino acids 225-336.
Coley, et al., Structure of the Malaria Antigen AMA1 in Complex with a Growth-Inhibitory Antibody, PLoS Pathog 2007, 3(9): e138: p. 1310, Fig 3 and its legend.
Hodder et al., "Specificity of the Protective Antibody Response to Apical Membrane Antigen 1", Infection and Immunity, vol. 69, No. 5, May 2001, p. 3286-3294.

* cited by examiner

*Primary Examiner* — Rodney P Swartz
(74) *Attorney, Agent, or Firm* — McAndrews, Held & Malloy, Ltd.

(57) ABSTRACT

Disclosed are AMA-1 immunogenic peptides and epitopes, nucleotide sequences encoding the peptides and epitopes, compositions, and vaccines including the peptides and/or epitopes. Antibodies that specifically bind to AMA-1 and the AMA-1 epitopes and immunogenic peptides disclosed herein are also provided. The disclosure provides for expression vectors, host cells, and methods for making the polypeptides and antibodies. Also provided are methods of treatment, prevention, vaccination, and/or immunization of a subject against malaria and the clinical indications associated with malaria.

12 Claims, 13 Drawing Sheets
(12 of 13 Drawing Sheet(s) Filed in Color)
Specification includes a Sequence Listing.

| Used in invasion assay | Duan et al. PNAS. | Polley et. al. 2001 Genetics | Escalante et al. Mol. Biochem Parasitol 2001. | Kocken et al Mol Biochem Parasitol 2000 |
|---|---|---|---|---|
| 3D7 | M27133 FC27 | AJ408318 isolate nigerian 054 | AY016415 Ven 61 | AJ271170 benin |
| FVO | M58546 FCR3 | AJ408300 isolate nigerian 002 | AY016412 Ven60 | AJ271171 benin |
| W2mef | M58547 THAI | AJ408301 isolate nigerian 005 | AY016413 Isolate 08-0697 | AJ271172 benin |
| U33277 HB3 | PC26 | AJ408330 isolate nigerian 078 | AY016414 Ven 66 | AJ271173 benin |
| M24 | S35 | AJ408342 isolate nigerian 105 | AY016416 Ven 67 | AJ271174 benin |
| M58548 7G8 | U33275CMP1 | AJ408348 isolate nigerian 114b | AY016417 Ven 65 | AJ271175 benin |
| 102-1 | U33276 V1 | AJ408302 isolate nigerian 006 | AY016418 Ven 62 | AJ271176 benin |
| SA250 | 425 | AJ408303 isolate nigerian 015 | AY016419 Ven 64 | AJ271177 benin |
| CP887 | AF061332 PNG | AJ408304 isolate nigerian 016 | AY016420 Ven 63 | AJ271179 benin |
| CP803 | FAB9 | AJ408305 isolate nigerian 026 | AY016421 Ven 68 | AJ271180 benin |
| CP845 | FCB strain | AJ408306 isolate nigerian 029 | AY016422 Ven 59 | AJ271181 benin |
| CP806 | L32 | AJ408307 isolate nigerian 030 | AY016423 isolate 14-0606 | AJ271182 benin |
| CP830 | M5 | AJ408308 isolate nigerian 034a | AY016424 isolate 03-0706 | AJ271183 benin |
| MT_s1 | U33280 NF7 | AJ408309 isolate nigerian 034b | AY016426 isolate 03-0243 | AJ271184 benin |
| GB4 | D6 | AJ408310 isolate nigerian 035 | AY016427 isolate 04-0654 | AJ271185 benin |
| XIE | C235 | AJ408311 isolate nigerian 036 | AY016428 isolate Fas | AJ271186 benin |
| E8B07 | ACB87904 Thy19 | AJ408312 isolate nigerian 039 | AY016429 isolate SL81 | AJ271187 benin |
| CSL-2 | ACB87902 Thai2_1 | AJ408313 isolate nigerian 043 | AY016430 isolate T422 | AJ271188 benin |
| CAMP | ACB87900 tha18_1 | AJ408314 isolate nigerian 044 | AY016431 isolate FJB D9E | AJ271189 benin |
| D10 | ACB87898 SL_d6 | AJ408315 isolate nigerian 035 | AY016432 isolate 395-94 | AJ271190 benin |
| K1 | ACB87896 ren | AJ408316 isolate nigerian 050 | AY016433 isolate 13-0608 | AJ271178 benin |
| T996 | ACB87894 PNG_9-1 | AJ408317 isolate nigerian 050 | AY016434 isolate RPF 2 | AJ271168 benin |
| HCS-E5 | ACB87892 png_4 | AJ408319 isolate nigerian 057 | AY016435 isolate T424 | AJ271169. benin |
| 2006 | ACB87890 png2 | AJ408320 isolate nigerian 057 | AY016436 isolate T420 | AJ252087 P. reichenowi |
| 2004 | ACB87888 png10_1 | AJ408321 isolate nigerian 058 | AY016437 isolate HD C15-1 | |
| C2A | ACB87886 pc26 | AJ408322 isolate nigerian 059 | AY016438 isolate 2180 | |
| | ACB87884 pc15 | AJ408323 isolate nigerian 060 | AY016439 isolate FDL NG | |
| | ACB87882 par | AJ408324 isolate nigerian 062 | | |
| U45969 P. berghei | ACB87880 p98_5 | AJ408325 isolate nigerian 064 | | |
| | ACB87878 p98_18 | AJ408326 isolate nigerian 065 | | |
| | ACB87876 p98_11 | AJ408327 isolate nigerian 066 | | |
| | ACB87874 p13 | AJ408328 isolate nigerian 067 | | |
| | ACB87872 s824 | AJ408329 isolate nigerian 077 | | |
| | ACB87870 s626 | AJ408331 isolate nigerian 083 | | |
| | ACB87868 s584 | AJ408332 isolate nigerian 080 | | |
| | ACB87866 | AJ408333 isolate nigerian 087 | | |
| | ACB87788 | AJ408334 isolate nigerian 088 | | |
| | ACB87790 | AJ408335 isolate nigerian 089 | | |
| | ACB87792 | AJ408336 isolate nigerian 091 | | |
| | ACB87794 | AJ408337 isolate nigerian 092 | | |
| | ACB87796 | AJ408338 isolate nigerian 094 | | |
| | ACB87798 | AJ408339 isolate nigerian 096 | | |
| | ACB87800 | AJ408340 isolate nigerian 100 | | |
| | ACB87802 | AJ408341 isolate nigerian 101 | | |
| | ACB87804 | AJ408343 isolate nigerian 107 | | |
| | ACB87806 | AJ408344 isolate nigerian 108 | | |
| | ACB87808 | AJ408345 isolate nigerian 110 | | |
| | ACB87810 | AJ408346 isolate nigerian 113 | | |
| | ACB87812 | AJ408347 isolate nigerian 114a | | |
| | ACB87814 | AJ408349 isolate nigerian 117 | | |
| | ACB87816 | AJ408350 isolate nigerian 119 | | |
| | ACB87818 | | | |
| | ACB87820 | | | |
| | ACB87822 | | | |
| | ACB87824 | | | |
| | ACB87826 | | | |
| | ACB87828 | | | |
| | ACB87830 | | | |
| | ACB87832 | | | |
| | ACB87834 | | | |
| | ACB87836 | | | |
| | ACB87838 | | | |
| | ACB87840 | | | |
| | ACB87842 | | | |
| | ACB87844 | | | |
| | ACB87846 | | | |
| | ACB87848 | | | |
| | ACB87850 | | | |
| | ACB87852 | | | |
| | ACB87854 | | | |
| | ACB87856 | | | |
| | ACB87858 | | | |
| | ACB87860 | | | |
| | ACB87862 | | | |

SEQUENCE LISTING

<160> NUMBER OF SEQ ID NOS: 73

<210> SEQ ID NO 1
<211> LENGTH: 12
<212> TYPE: PRT
<213> ORGANISM: Artificial Sequence
<220> FEATURE:
<223> OTHER INFORMATION: Amino Acid Sequence of 1 e loop AMA protein

<400> SEQUENCE: 1

Ile Pro Asp Asn Asp Lys Asn Ser Asn Tyr Lys Tyr
1               5                   10

<210> SEQ ID NO 2
<211> LENGTH: 113
<212> TYPE: PRT
<213> ORGANISM: Artificial Sequence
<220> FEATURE:
<223> OTHER INFORMATION: Amino Acid Sequence of Domain 3 region of AMA-1

<400> SEQUENCE: 2

Leu Ile Asn Asn Ser Ser Tyr Ile Ala Thr Thr Ala Leu Ser His Pro
1               5                   10                  15

Ile Glu Val Glu Asn Asn Phe Pro Cys Ser Leu Tyr Lys Asp Glu Ile
            20                  25                  30

Met Lys Glu Ile Glu Arg Glu Ser Lys Arg Ile Lys Leu Asn Asp Asn
35 40 45

Asp Asp Glu Gly Asn Lys Lys Ile Ile Ala Pro Arg Ile Phe Ile Ser
50 55 60

Asp Asp Lys Asp Ser Leu Lys Cys Pro Cys Asp Pro Glu Met Val Ser
65 70 75 80

Asn Ser Thr Cys Arg Phe Phe Val Cys Lys Cys Val Glu Arg Arg Ala
85 90 95

Glu Val Thr Ser Asn Asn Glu Val Val Val Lys Glu Glu Tyr Lys Asp
100 105 110

Glu

<210> SEQ ID NO 3
<211> LENGTH: 449
<212> TYPE: PRT
<213> ORGANISM: Artificial Sequence
<220> FEATURE:
<223> OTHER INFORMATION: Amino Acid Sequence of FVO AMA-1 protein

<400> SEQUENCE: 3

Gly Ala Glu Pro Ala Pro Gln Glu Gln Asn Leu Phe Pro Ser Ile Glu
1 5 10 15

Ile Val Glu Arg Ser Asn Tyr Met Gly Asn Pro Trp Thr Glu Tyr Met
20 25 30

Ala Lys Tyr Asp Ile Glu Glu Val His Gly Ser Gly Ile Arg Val Asp
35 40 45

Leu Gly Glu Asp Ala Glu Val Ala Gly Thr Gln Tyr Arg Leu Pro Ser
50 55 60

Gly Lys Cys Pro Val Phe Gly Lys Gly Ile Ile Ile Glu Asn Ser Asn
65 70 75 80

Thr Thr Phe Leu Lys Pro Val Ala Thr Gly Asn Gln Asp Leu Lys Asp
85 90 95

Gly Gly Phe Ala Phe Pro Pro Thr Asn Pro Leu Ile Ser Pro Met Thr
100 105 110

Leu Asn Gly Met Arg Asp Phe Tyr Lys Asn Asn Glu Tyr Val Lys Asn
            115                 120                 125

Leu Asp Glu Leu Thr Leu Cys Ser Arg His Ala Gly Asn Met Asn Pro
        130                 135                 140

Asp Asn Asp Lys Asn Ser Asn Tyr Lys Tyr Pro Ala Val Tyr Asp Tyr
145                 150                 155                 160

Asn Asp Lys Lys Cys His Ile Leu Tyr Ile Ala Ala Gln Glu Asn Asn
                165                 170                 175

Gly Pro Arg Tyr Cys Asn Lys Asp Gln Ser Lys Arg Asn Ser Met Phe
            180                 185                 190

Cys Phe Arg Pro Ala Lys Asp Lys Leu Phe Glu Asn Tyr Thr Tyr Leu
        195                 200                 205

Ser Lys Asn Val Val Asp Asn Trp Glu Glu Val Cys Pro Arg Lys Asn
    210                 215                 220

Leu Glu Asn Ala Lys Phe Gly Leu Trp Val Asp Gly Asn Cys Glu Asp
225                 230                 235                 240

Ile Pro His Val Asn Glu Phe Ser Ala Asn Asp Leu Phe Glu Cys Asn
                245                 250                 255

Lys Leu Val Phe Glu Leu Ser Ala Ser Asp Gln Pro Lys Gln Tyr Glu
            260                 265                 270

Gln His Leu Thr Asp Tyr Glu Lys Ile Lys Glu Gly Phe Lys Asn Lys
        275                 280                 285

Asn Ala Ser Met Ile Lys Ser Ala Phe Leu Pro Thr Gly Ala Phe Lys
    290                 295                 300

Ala Asp Arg Tyr Lys Ser His Gly Lys Gly Tyr Asn Trp Gly Asn Tyr
305                 310                 315                 320

Asn Arg Glu Thr Gln Lys Cys Glu Ile Phe Asn Val Lys Pro Thr Cys
                325                 330                 335

Leu Ile Asn Asn Ser Ser Tyr Ile Ala Thr Thr Ala Leu Ser His Pro
            340                 345                 350

Ile Glu Val Glu His Asn Phe Pro Cys Ser Leu Tyr Lys Asp Glu Ile
        355                 360                 365

Lys Lys Glu Ile Glu Arg Glu Ser Lys Arg Ile Lys Leu Asn Asp Asn
    370                 375                 380

Asp Asp Glu Gly Asn Lys Lys Ile Ile Ala Pro Arg Ile Phe Ile Ser
385                 390                 395                 400

Asp Asp Lys Asp Ser Leu Lys Cys Pro Cys Asp Pro Glu Met Val Ser
                405                 410                 415

Asn Ser Thr Cys Arg Phe Phe Val Cys Lys Cys Val Glu Arg Arg Ala
            420                 425                 430

Glu Val Thr Ser Asn Asn Glu Val Val Lys Glu Glu Tyr Lys Asp
        435                 440                 445

Glu

<210> SEQ ID NO 4
<211> LENGTH: 449
<212> TYPE: PRT
<213> ORGANISM: Artificial Sequence
<220> FEATURE:
<223> OTHER INFORMATION: Amino acid sequence of HB3 AMA-1 protein

<400> SEQUENCE: 4

Gly Ala Glu Pro Ala Pro Gln Glu Gln Asn Leu Phe Ser Ser Ile Glu
1               5                   10                  15

Ile Val Glu Arg Ser Asn Tyr Met Gly Asn Pro Trp Thr Glu Tyr Met

-continued

```
                20                  25                  30
Ala Lys Tyr Asp Ile Glu Lys Val His Gly Ser Gly Ile Arg Val Asp
            35                  40                  45
Leu Gly Glu Asp Ala Glu Val Ala Gly Thr Gln Tyr Arg Leu Pro Ser
        50                  55                  60
Gly Lys Cys Pro Val Phe Gly Lys Gly Ile Ile Glu Asn Ser Lys
65                  70                  75                  80
Thr Thr Phe Leu Thr Pro Val Ala Thr Glu Asn Gln Asp Leu Lys Asp
                85                  90                  95
Gly Gly Phe Ala Phe Pro Pro Thr Glu Pro Leu Ile Ser Pro Met Thr
            100                 105                 110
Leu Asp Gln Met Arg His Leu Tyr Lys Asp Asn Glu Tyr Val Lys Asn
        115                 120                 125
Leu Asp Glu Leu Thr Leu Cys Ser Arg His Ala Gly Asn Met Asn Pro
        130                 135                 140
Asp Asn Asp Lys Asn Ser Asn Tyr Lys Tyr Pro Ala Val Tyr Asp Tyr
145                 150                 155                 160
Glu Asp Lys Lys Cys His Ile Leu Tyr Ile Ala Ala Gln Glu Asn Asn
                165                 170                 175
Gly Pro Arg Tyr Cys Asn Lys Asp Glu Ser Lys Arg Asn Ser Met Phe
            180                 185                 190
Cys Phe Arg Pro Ala Lys Asp Lys Leu Phe Glu Asn Tyr Thr Tyr Leu
        195                 200                 205
Ser Lys Asn Val Val Asp Asn Trp Glu Glu Val Cys Pro Arg Lys Asn
        210                 215                 220
Leu Glu Asn Ala Lys Phe Gly Leu Trp Val Asp Gly Asn Cys Glu Asp
225                 230                 235                 240
Ile Pro His Val Asn Glu Phe Ser Ala Asn Asp Leu Phe Glu Cys Asn
                245                 250                 255
Lys Leu Val Phe Glu Leu Ser Ala Ser Asp Gln Pro Lys Gln Tyr Glu
            260                 265                 270
Gln His Leu Thr Asp Tyr Glu Lys Ile Lys Glu Gly Phe Lys Asn Lys
        275                 280                 285
Asn Ala Ser Met Ile Lys Ser Ala Phe Leu Pro Thr Gly Ala Phe Lys
        290                 295                 300
Ala Asp Arg Tyr Lys Ser Arg Gly Lys Gly Tyr Asn Trp Gly Asn Tyr
305                 310                 315                 320
Asn Thr Glu Thr Gln Lys Cys Glu Ile Phe Asn Val Lys Pro Thr Cys
                325                 330                 335
Leu Ile Asn Asn Ser Ser Tyr Ile Ala Thr Thr Ala Leu Ser His Pro
            340                 345                 350
Asn Glu Val Glu Asn Asn Phe Pro Cys Ser Leu Tyr Lys Asp Glu Ile
        355                 360                 365
Lys Lys Glu Ile Glu Arg Glu Ser Lys Arg Ile Lys Leu Asn Asp Asn
        370                 375                 380
Asp Asp Glu Gly Asn Lys Lys Ile Ile Ala Pro Arg Ile Phe Ile Ser
385                 390                 395                 400
Asp Asp Lys Asp Ser Leu Lys Cys Pro Cys Asp Pro Glu Ile Val Ser
                405                 410                 415
Asn Ser Thr Cys Asn Phe Phe Val Cys Lys Cys Val Glu Lys Arg Ala
            420                 425                 430
Glu Val Thr Ser Asn Asn Glu Val Val Lys Glu Glu Tyr Lys Asp
        435                 440                 445
```

Glu

<210> SEQ ID NO 5
<211> LENGTH: 449
<212> TYPE: PRT
<213> ORGANISM: Artificial Sequence
<220> FEATURE:
<223> OTHER INFORMATION: Amino Acid Sequence of W2Mef AMA-1 protein

<400> SEQUENCE: 5

```
Gly Ala Glu Pro Ala Pro Gln Glu Gln Asn Leu Phe Ser Ser Ile Glu
1               5                   10                  15

Ile Val Glu Arg Ser Asn Tyr Met Gly Asn Pro Trp Thr Glu Tyr Met
            20                  25                  30

Ala Lys Tyr Asp Ile Glu Glu Val His Gly Ser Gly Ile Arg Val Asp
        35                  40                  45

Leu Gly Glu Asp Ala Glu Val Ala Gly Thr Gln Tyr Arg Leu Pro Ser
    50                  55                  60

Gly Lys Cys Pro Val Phe Gly Lys Gly Ile Ile Ile Glu Asn Ser Asn
65                  70                  75                  80

Thr Thr Phe Leu Thr Pro Val Ala Thr Gly Asn Gln Tyr Leu Lys Asp
                85                  90                  95

Gly Gly Phe Ala Phe Pro Pro Thr Lys Pro Leu Met Ser Pro Met Thr
            100                 105                 110

Leu Asp Asp Met Arg Leu Leu Tyr Lys Asp Asn Glu Asp Val Lys Asn
        115                 120                 125

Leu Asp Glu Leu Thr Leu Cys Ser Arg His Ala Gly Asn Met Asn Pro
    130                 135                 140

Asp Asn Asp Lys Asn Ser Asn Tyr Lys Tyr Pro Ala Val Tyr Asp Tyr
145                 150                 155                 160

Asn Asp Lys Lys Cys His Ile Leu Tyr Ile Ala Ala Gln Glu Asn Asn
                165                 170                 175

Gly Pro Arg Tyr Cys Asn Lys Asp Glu Ser Lys Arg Asn Ser Met Phe
            180                 185                 190

Cys Phe Arg Pro Ala Lys Asp Lys Ser Phe Gln Asn Tyr Thr Tyr Leu
        195                 200                 205

Ser Lys Asn Val Val Asp Asn Trp Glu Glu Val Cys Pro Arg Lys Asn
    210                 215                 220

Leu Glu Asn Ala Lys Phe Gly Leu Trp Val Asp Gly Asn Cys Glu Asp
225                 230                 235                 240

Ile Pro His Val Asn Glu Phe Ser Ala Asn Asp Leu Phe Glu Cys Asn
                245                 250                 255

Lys Leu Val Phe Glu Leu Ser Ala Ser Asp Gln Pro Lys Gln Tyr Glu
            260                 265                 270

Gln His Leu Thr Asp Tyr Glu Lys Ile Lys Glu Gly Phe Lys Asn Lys
        275                 280                 285

Asn Ala Ser Met Ile Lys Ser Ala Phe Leu Pro Thr Gly Ala Phe Lys
    290                 295                 300

Ala Asp Arg Tyr Lys Ser His Gly Lys Gly Tyr Asn Trp Gly Asn Tyr
305                 310                 315                 320

Asn Arg Lys Thr Gln Lys Cys Glu Ile Phe Asn Val Lys Pro Thr Cys
                325                 330                 335

Leu Ile Asn Asn Ser Ser Tyr Ile Ala Thr Thr Ala Leu Ser His Pro
            340                 345                 350
```

-continued

```
Ile Glu Val Glu His Asn Phe Pro Cys Ser Leu Tyr Lys Asp Glu Ile
            355                 360                 365

Lys Lys Glu Ile Glu Arg Glu Ser Lys Arg Ile Lys Leu Asn Asp Asn
370                 375                 380

Asp Asp Glu Gly Asn Lys Lys Ile Ile Ala Pro Arg Ile Phe Ile Ser
385                 390                 395                 400

Asp Asp Ile Asp Ser Leu Lys Cys Pro Cys Asp Pro Glu Ile Val Ser
                405                 410                 415

Asn Ser Thr Cys Asn Phe Phe Val Cys Lys Cys Val Glu Lys Arg Ala
            420                 425                 430

Glu Val Thr Ser Asn Asn Glu Val Val Val Lys Glu Gly Tyr Lys Asp
            435                 440                 445

Glu

<210> SEQ ID NO 6
<211> LENGTH: 449
<212> TYPE: PRT
<213> ORGANISM: Artificial Sequence
<220> FEATURE:
<223> OTHER INFORMATION: Amino acid sequence of 3D7 AMA-1 protein

<400> SEQUENCE: 6

Gly Ala Glu Pro Ala Pro Gln Glu Gln Asn Leu Phe Ser Ser Ile Glu
1               5                   10                  15

Ile Val Glu Arg Ser Asn Tyr Met Gly Asn Pro Trp Thr Glu Tyr Met
            20                  25                  30

Ala Lys Tyr Asp Ile Glu Glu Val His Gly Ser Gly Ile Arg Val Asp
        35                  40                  45

Leu Gly Glu Asp Ala Glu Val Ala Gly Thr Gln Tyr Arg Leu Pro Ser
    50                  55                  60

Gly Lys Cys Pro Val Phe Gly Lys Gly Ile Ile Ile Glu Asn Ser Asn
65                  70                  75                  80

Thr Thr Phe Leu Thr Pro Val Ala Thr Gly Asn Gln Tyr Leu Lys Asp
                85                  90                  95

Gly Gly Phe Ala Phe Pro Pro Thr Glu Pro Leu Met Ser Pro Met Thr
            100                 105                 110

Leu Asp Glu Met Arg His Phe Tyr Lys Asp Asn Lys Tyr Val Lys Asn
        115                 120                 125

Leu Asp Glu Leu Thr Leu Cys Ser Arg His Ala Gly Asn Met Ile Pro
    130                 135                 140

Asp Asn Asp Lys Asn Ser Asn Tyr Lys Tyr Pro Ala Val Tyr Asp Asp
145                 150                 155                 160

Lys Asp Lys Lys Cys His Ile Leu Tyr Ile Ala Ala Gln Glu Asn Asn
                165                 170                 175

Gly Pro Arg Tyr Cys Asn Lys Asp Glu Ser Lys Arg Asn Ser Met Phe
            180                 185                 190

Cys Phe Arg Pro Ala Lys Asp Ile Ser Phe Gln Asn Tyr Thr Tyr Leu
        195                 200                 205

Ser Lys Asn Val Val Asp Asn Trp Glu Lys Val Cys Pro Arg Lys Asn
    210                 215                 220

Leu Gln Asn Ala Lys Phe Gly Leu Trp Val Asp Gly Asn Cys Glu Asp
225                 230                 235                 240

Ile Pro His Val Asn Glu Phe Pro Ala Ile Asp Leu Phe Glu Cys Asn
                245                 250                 255

Lys Leu Val Phe Glu Leu Ser Ala Ser Asp Gln Pro Lys Gln Tyr Glu
```

```
                260                 265                 270
Gln His Leu Thr Asp Tyr Glu Lys Ile Lys Glu Gly Phe Lys Asn Lys
                275                 280                 285

Asn Ala Ser Met Ile Lys Ser Ala Phe Leu Pro Thr Gly Ala Phe Lys
            290                 295                 300

Ala Asp Arg Tyr Lys Ser His Gly Lys Gly Tyr Asn Trp Gly Asn Tyr
305                 310                 315                 320

Asn Thr Glu Thr Gln Lys Cys Glu Ile Phe Asn Val Lys Pro Thr Cys
                325                 330                 335

Leu Ile Asn Asn Ser Ser Tyr Ile Ala Thr Thr Ala Leu Ser His Pro
            340                 345                 350

Ile Glu Val Glu Asn Asn Phe Pro Cys Ser Leu Tyr Lys Asp Glu Ile
                355                 360                 365

Met Lys Glu Ile Glu Arg Glu Ser Lys Arg Ile Lys Leu Asn Asp Asn
            370                 375                 380

Asp Asp Glu Gly Asn Lys Lys Ile Ile Ala Pro Arg Ile Phe Ile Ser
385                 390                 395                 400

Asp Asp Lys Asp Ser Leu Lys Cys Pro Cys Asp Pro Glu Met Val Ser
                405                 410                 415

Asn Ser Thr Cys Arg Phe Phe Val Cys Lys Cys Val Glu Arg Arg Ala
            420                 425                 430

Glu Val Thr Ser Asn Asn Glu Val Val Val Lys Glu Gly Tyr Lys Asp
                435                 440                 445

Glu

<210> SEQ ID NO 7
<211> LENGTH: 449
<212> TYPE: PRT
<213> ORGANISM: Artificial Sequence
<220> FEATURE:
<223> OTHER INFORMATION: Amino acid sequence of 7G8 AMA1

<400> SEQUENCE: 7

Gly Ala Glu Pro Ala Pro Gln Glu Gln Asn Leu Phe Ser Ser Ile Glu
1               5                   10                  15

Ile Val Glu Arg Ser Asn Tyr Met Gly Asn Pro Trp Thr Glu Tyr Met
                20                  25                  30

Ala Lys Tyr Asp Ile Lys Glu Val His Gly Ser Gly Ile Arg Val Asp
            35                  40                  45

Leu Gly Glu Asp Ala Glu Val Ala Gly Thr Gln Tyr Arg Leu Pro Ser
50                  55                  60

Gly Lys Cys Pro Val Phe Gly Lys Gly Ile Ile Ile Glu Asn Ser Asn
65                  70                  75                  80

Thr Thr Phe Leu Lys Pro Val Ala Thr Gly Asn Gln Asp Leu Lys Asp
                85                  90                  95

Gly Gly Phe Ala Phe Pro Pro Thr Asn Pro Leu Ile Ser Pro Met Thr
            100                 105                 110

Leu Asp His Met Arg Asp Phe Tyr Lys Asn Asn Glu Tyr Val Lys Asn
        115                 120                 125

Leu Asp Glu Leu Thr Leu Cys Ser Arg His Ala Gly Asn Met Asn Pro
    130                 135                 140

Asp Asn Asp Lys Asn Ser Asn Tyr Lys Tyr Pro Ala Val Tyr Asp Tyr
145                 150                 155                 160

Asn Asp Lys Lys Cys His Ile Leu Tyr Ile Ala Ala Gln Glu Asn Asn
                165                 170                 175
```

Gly Pro Arg Tyr Cys Asn Lys Asp Glu Ser Lys Arg Asn Ser Met Phe
            180                 185                 190

Cys Phe Arg Pro Ala Lys Asp Lys Ser Phe Gln Asn Tyr Thr Tyr Leu
            195                 200                 205

Ser Lys Asn Val Val Asp Asn Trp Glu Lys Val Cys Pro Arg Lys Asn
210                 215                 220

Leu Glu Asn Ala Lys Phe Gly Leu Trp Val Asp Gly Asn Cys Glu Asp
225                 230                 235                 240

Ile Pro His Val Asn Glu Phe Ser Ala Asn Asp Leu Phe Glu Cys Asn
            245                 250                 255

Lys Leu Val Phe Glu Leu Ser Ala Ser Asp Gln Pro Lys Gln Tyr Glu
            260                 265                 270

Gln His Leu Thr Asp Tyr Glu Lys Ile Lys Glu Gly Phe Lys Asn Lys
            275                 280                 285

Asn Ala Ser Met Ile Lys Ser Ala Phe Leu Pro Thr Gly Ala Phe Lys
            290                 295                 300

Ala Asp Arg Tyr Lys Ser Arg Gly Lys Gly Tyr Asn Trp Gly Asn Tyr
305                 310                 315                 320

Asn Arg Lys Thr Gln Lys Cys Glu Ile Phe Asn Val Lys Pro Thr Cys
            325                 330                 335

Leu Ile Asn Asn Ser Ser Tyr Ile Ala Thr Thr Ala Leu Ser His Pro
            340                 345                 350

Asn Glu Val Glu His Asn Phe Pro Cys Ser Leu Tyr Lys Asp Glu Ile
            355                 360                 365

Lys Lys Glu Ile Glu Arg Glu Ser Lys Arg Ile Lys Leu Asn Asp Asn
            370                 375                 380

Asp Asp Glu Gly Asn Lys Lys Ile Ile Ala Pro Arg Ile Phe Ile Ser
385                 390                 395                 400

Asp Asp Ile Asp Ser Leu Lys Cys Pro Cys Asp Pro Glu Ile Val Ser
            405                 410                 415

Asn Ser Thr Cys Asn Phe Phe Val Cys Lys Cys Val Glu Lys Arg Ala
            420                 425                 430

Glu Val Thr Ser Asn Asn Glu Val Val Lys Glu Gly Tyr Lys Asp
            435                 440                 445

Glu

<210> SEQ ID NO 8
<211> LENGTH: 1358
<212> TYPE: DNA
<213> ORGANISM: Artificial Sequence
<220> FEATURE:
<223> OTHER INFORMATION: 7G8 AMA-1 nucleic acid sequence

<400> SEQUENCE: 8
ggcgcagaac cagcaccgca agaacagaac ttattcagca gcattgagat tgtcgagcgc      60
tccaattaca tgggcaaccc gtggaccgag tacatggcca agtatgacat aaagagggtc     120
cacggtagcg gcattcgtgt ggacctgggc gaagatgcgg aagtagcagg tacccagtac     180
cgcttgccga gcggcaaatg cccggttttc ggcaaaggta tcatcatcga aactctaac      240 accaccttcc tgaagccggt tgccaccggt aatcaagatc tgaaggacgg cggttttgcc     300
tttccgccga ccaacccact gattagccct atgacgctgg atcacatgcg tgacttttac     360
aaaaacaacg agtacgtgaa gaaccttgat gaactgacgc tgtgtagccg tcatgcgggt     420
aatatgaatc cggacaatga taagaatagc aactacaaat acccggcagt ttatgactat     480

```
aatgacaaga aatgccatat tctgtacatt gcggcacaag agaataatgg tccgcgttat      540
tgtaacaaag atgaaagcaa acgcaacagc atgttctgtt ttcgtccggc aaaggataaa      600
agcttccaaa actacaccta tctgagcaaa aacgttgtgg acaactggga gaaagtttgc      660
ccgcgtaaaa acttggagaa cgccaagttc ggtctgtggg tggacggcaa ttgcgaggat      720
atcccgcacg tcaatgaatt cagcgcgaat gacctgttcg agtgcaataa gttagttttt      780
gagctgagcg ctagcgacca gccgaagcag tacgagcagc acctgaccga ctatgagaag      840
atcaaagaag gtttcaagaa caagaatgca tccatgatca aaagcgcctt tcttccaact      900
ggcgcgttca agctgatccg ttacaagagc cgtggtaaag gctataactg gggcaactat      960
aatcgtaaga cgcagaagtg tgagattttc aatgtaaagc cgacgtgcct gatcaataac     1020
agcagctaca tcgccacgac cgcgctgagc caccgaacg aggtggagca taactttccg     1080
tgcagcctgt ataaggacga gatcaagaag gagatcgaac gcgagtccaa acgcatcaag     1140
ctgaatgata cgacgatga gggtaacaag aagattatcg ctccgagaat tttcatttct     1200
gatgatattg acagcttgaa gtgcccgtgt gatccggaaa tcgtttcgaa tagcacctgc     1260
aatttctttg tgtgcaaatg tgtcgagaaa cgcgcagagg tcaccagcaa taacgaggtc     1320
gtggtcaaag aggaatacaa agacgagtaa gcggccgc                            1358

<210> SEQ ID NO 9
<211> LENGTH: 1358
<212> TYPE: DNA
<213> ORGANISM: Artificial Sequence
<220> FEATURE:
<223> OTHER INFORMATION: M24 AMA-1 nucleic acid acid sequence

<400> SEQUENCE: 9
ggtgcggagc cagccccgca ggagcaaaat ctgttcagct ccattgagat tgtcgaacgc       60
tctaactata tgggcaatcc atggaccgag tatatggcga agtacgatat tgaagaagtg      120
cacggttccg gtattcgtgt tgatttgggt gaggatgcgg aggtcgctgg cacccagtac      180
cgtttgccga gcggtaagtg cccggttttt ggcaaaggta tcatcatcga aaacagcaac      240 accaccttc tgactccggt cgcaacggaa atcaggacc tgaaggacgg tggttttgcg      300
tttccgccga cgaaaccgct gatgtccccg atgacgctgg atcaaatgcg tgatttctac      360
aaaaacaatg aatatgtcaa aaacctggac gagctgacgt tgtgctctcg ccacgccggt      420
aacatgaatc cggataacga cgagaataga aactataagt atccggcagt gtatgattac      480
aaagacaaga aatgccatat cctgtacatt gcagcacaag aaaacaatgg tccgcgttac      540
tgcaacaaag atcagagcaa acgcaacagc atgttctgct ttcgtcctgc aaaggataag      600
ctgttcgaga attacaccta tctgagcaaa acgtggtgc acaattggga gaaggtgtgt      660
cctcgtaaga atctgcagaa cgcgaaattc ggcctgtggg tcgacggtaa ctgtgaggac      720
atcccgcatg tgaacgaatt cagcgcgaac gatctgttcg aatgcaacaa gctggtctttt     780 gaactgtccg ccagcgatca accgaagcaa tacgaacagc atctgaccga ctacgagaag      840
atcaaagagg gtttcaaaaa caagaacgca agcatgatta gtccgcgtt tttgccgacg      900 ggtgcgttta aggccgaccg ctacaagagc cgtggcaaag ctacaattg gggtaactac      960 aataccaaaa ctcaaaagtg tgagatcttt aacgtgaaac caacgtgtct gattaacaat     1020
agctcttaca tcgcgaccac cgcgttgagc caccgattg aggtggaaca caatttcccg     1080
tgtagcttgt ataaggacga gattaagaaa gagatcgagc gtgagagcaa agcgcatcaag    1140
```

```
ctgaacgata atgatgacga gggcaataag aagattatcg caccgcgtat cttcattagc    1200
gacgacattg atagcctgaa atgtccgtgt gacccggaga tggtcagcaa cagcacttgc    1260
cgcttctatg tctgcaagtg cgttgagcgt cgtgctgagg tgaccagcaa caacgaggtc    1320
gtggttaaag aagaatacaa ggatgagtga gcggccgc                            1358
```

<210> SEQ ID NO 10
<211> LENGTH: 1358
<212> TYPE: DNA
<213> ORGANISM: Artificial Sequence
<220> FEATURE:
<223> OTHER INFORMATION: HB3 AMA-1 nucleic acid sequence

<400> SEQUENCE: 10

```
ggtgcggagc cggcaccgca ggagcagaat ctgttttcct ctatcgagat tgttgagcgt     60
agcaattaca tgggcaatcc gtggaccgag tatatggcca gtacgacat cgagaaagtt    120 catggcagcg gtatccgcgt cgatctgggc gaagatgcgg aggttgcagg cacccaatac    180
cgcctgccgt ctggtaaatg ccctgttttc ggtaaaggca ttatcatcga aatagcaaa    240 acgacctttc tgaccccggt tgcaactgag aaccaagacc tgaaagacgg tggcttcgcc    300
tttccgccga ccgagccatt gatttccccg atgacgctgg accagatgcg tcacctgtat    360
aaggacaatg agtacgtgaa aaatctggat gaactgaccc tgtgctcgcg tcacgcgggt    420
aacatgaatc cggacaacga taagaatagc aactataagt atccagcagt ctacgattac    480
gaggacaaga gtgccatat tctgtacatt gcggcacaag aaaacaatgg tccgcgttat    540
tgtaacaagg atgagtctaa acgtaattcc atgttctgct ttcgtccggc gaaagataaa    600
ctgttcgaaa actataccta cttgagcaag aatgtggtgg acaactggga gaggtctgt    660 ccgcgtaaga acttggaaaa cgctaaattc ggtctgtggg tggatggtaa ctgtgaagat    720
attccgcacg tgaatgagtt cagcgcgaat gatctgtttg aatgcaacaa actggtcttt    780
gagttgagcg cgagcgacca gccgaaacaa tatgaacagc acttgaccga ttacgaaaag    840
atcaaggaag gttttaagaa taagaacgcg agcatgatca aaagcgcatt tctgccgacc    900
ggtgcgttca agccgaccg ctacaagagc cgcggtaaag gttataactg ggcaattac    960 aacaccgaaa cgcaaaaatg cgagatcttc aacgtgaaac cgacttgtct gatcaacaat    1020
tctagctaca ttgctacgac cgccctgagc catccaaacg aagttgagaa caactttccg    1080
tgcagcctgt ataaagacga gatcaaaaag gagatcgaac gtgaatccaa cgcattaaa    1140 ctgaatgaca cgacgatga gggcaataag aaaatcattg ctccgcgtat tttcattagc    1200
gatgacaagg acagcctgaa gtgtccgtgt gatcctgaga ttgtcagcaa tagcacgtgt    1260
aatttcttcg tgtgcaagtg cgttgaaaag cgtgcggaag ttacgagcaa caacgaggtc    1320
gtggttaagg aagagtacaa agacgagtaa gcggccgc                            1358
```

<210> SEQ ID NO 11
<211> LENGTH: 1347
<212> TYPE: DNA
<213> ORGANISM: Artificial Sequence
<220> FEATURE:
<223> OTHER INFORMATION: W2mef AMA-1 nucleic acid sequence

<400> SEQUENCE: 11

```
ggtgccgagc cagcgccgca agaacagaac ttgtttagct ccattgagat tgtagagcgt     60
agcaactaca tgggtaaccc gtggaccgaa tacatggcga gtatgatat tgaggaagtt    120 cacggcagcg gcattcgtgt tgacttgggt gaggacgctg aagtcgccgg cacccagtac    180
```

```
cgtctgccgt ctggtaaatg cccggtgttt ggcaaaggca tcatcatcga gaatagcaat      240 accaccttc  tgaccccgt  tgcgacgggc aatcagtatc tgaaagatgg tggcttcgcg      300
tttccgccga cgaagccgct gatgagcccg atgacgctgg atgacatgcg tctgctgtac      360
aaagataacg aggatgtgaa aaacctggac gaactgacgt tgtgtagccg tcatgcgggt      420
aatatgaacc cggacaacga caaaaactcc aattacaagt atccggcggt ctatgattac      480
aatgataaga agtgtcacat cctgtatatt gcggcccaag agaacaacgg tccgcgttac      540
tgcaacaaag acgaaagcaa acgtaacagc atgttttgct tccgtccggc taaagacaaa      600
tctttccaga attacaccta tctgtcgaaa acgtcgtgg  acaactggga ggaagtttgt      660
ccgcgtaaaa acttggagaa tgcaaaattc ggtctgtggg ttgacggtaa ctgtgaagat      720
attccgcatg tgaacgagtt tagcgcaaat gatctgtttg aatgtaacaa gttggttttc      780
gaactgtccg cgagcgatca acctaagcag tacgagcagc atctgaccga ctacgaaag    840 atcaaagagg gcttcaagaa caagaatgcc agcatgatca gagcgcgtt  cctgccgacc     900 ggtgcctta  aagcagaccg ctacaagagc cacggtaagg gttacaattg gggtaattac      960
aatcgcaaga ctcaaaaatg tgaaatcttc aatgtgaaac cgacctgcct gatcaacaat     1020
agcagctata ttgcaaccac ggcgctgagc caccccgattg aagtggagca caacttcccg     1080
tgcagcctgt ataagatga gatcaaaaag gagatcgagc gcgaatcgaa gcgtattaag     1140
ctgaatgaca atgacgatga aggcaataag aagattatcg caccacgcat cttcatctct     1200
gacgacattg atagcctgaa atgcccgtgc gatccggaga ttgtctccaa cagcacctgc     1260
aatttctttg tttgcaaatg tgtggaaaag cgcgcagagg ttacgagcaa caatgaggtg     1320
gtcgtcaaag aagagtataa ggacgaa                                         1347
```

<210> SEQ ID NO 12
<211> LENGTH: 1347
<212> TYPE: DNA
<213> ORGANISM: Artificial Sequence
<220> FEATURE:
<223> OTHER INFORMATION: 102-1 AMA-1 nucleic acid sequence

<400> SEQUENCE: 12

```
ggcgcagaac cagcaccgca ggaacagaac ttattcagct ccatcgagat tgtagaacgt       60
agcaactaca tgggtaatcc gtggaccgag tacatggcga agtatgatat cgaagaggtg      120
catggtagcg gcattcgcgt ggatttgggc gaggatgcgg aggttgcggg tacccaatac      180
cgcctgccgt ctggtaagtg cccggttttt ggcaaaggta tcatcatcga aaactctaac      240 actaccttc  tgacgccggt cgccaccgag aacaaagacc tgaaggacgg tggctttgcc      300
ttcccgccga ccgagccgct gatgtcgccg atgaccctgg acgatatgcg tcgtttctac      360
aaagacaatg aatatgtgaa gaatctggat gagctcaccc tgtgttcccg ccacgccggt      420
aacatgaatc cggacaatga caaaaacagc aactataagt acccggcagt ttacgattac      480
aacgataaga agtgtcacat cctttacatc gcagcgcagg aaaacaatgg tccgcgctac      540
tgcaacaaag atcagagcaa gcgtaatagc atgttctgtt tccgtccggc aaaagataag      600
ctgttcgaga attacacgta tctgtcgaag aatgtggttg acaactggga agaagtctgc     660
ccgcgtaaga acctcgagaa cgcaaagttc ggtctgtggg tcgacggcaa ctgcgaggac     720
attccgcatg ttaatgagtt tagcgcgaat gacctgttcg aatgcaacaa actggtgttt     780
gagctgagcg cttccgatca accgaagcag tacgaacagc atctgaccga ctacgagaaa     840
```

```
atcaaagaag gtttcaaaaa caaaaacgcg tctatgatta agagcgcgtt tctgccaacc    900
ggtgccttta aggcggaccg ttacaagagc cacggcaaag gttacaactg gggtaactac    960
aatcgcgaaa cccagaaatg cgagatcttc aatgtcaaac cgacgtgtct gatcaataac   1020
tctagctaca tcgcgacgac cgcgctgagc cacccgaacg aagttgaaca caatttcccg   1080
tgtagcctgt acaaagatga gatcaagaaa gaaatcgaga gagaaagcaa acgcatcaag   1140
ctgaacgaca acgatgatga gggcaacaag aagatcatcg caccgcgcat ctttatcagc   1200
gatgacattg actccctgaa atgcccttgc gatccagaga tcgtttccaa cagcacttgc   1260
aatttcttcg tctgcaagtg cgtggagaag cgtgcggagg tgacgtctaa caatgaggtt   1320
gtggttaaag aagagtacaa agacgag                                       1347
```

<210> SEQ ID NO 13
<211> LENGTH: 1347
<212> TYPE: DNA
<213> ORGANISM: Artificial Sequence
<220> FEATURE:
<223> OTHER INFORMATION: FVO AMA-1 nucleic acid sequence

<400> SEQUENCE: 13

```
ggcgcggaac cggcgccgca ggaacagaac ctgtttccga gcattgaaat tgtggaacgc     60
agcaactata tgggcaaccc gtggaccgaa tatatggcga aatatgatat tgaagaagtg    120
catggcagcg gcattcgcgt ggatctgggc gaagatgcgg aagtggcggg cacccagtat    180
cgcctgccga gcggcaaatg cccggtgttt ggcaaaggca ttattattga aaacagcaac    240 accaccttc tgaaaccggt ggcgaccggc aaccaggatc tgaaagatgg cggctttgcg    300
tttccgccga ccaacccgct gattagcccg atgaccctga acggcatgcg cgatttttat    360
aaaaacaacg aatatgtgaa aaacctggat gaactgaccc tgtgcagccg ccatgcgggc    420
aacatgaacc cggataacga taaaaacagc aactataaat atccggcggt gtatgattat    480
aacgataaaa aatgccatat tctgtatatt gcggcgcagg aaaacaacgg cccgcgctat    540
tgcaacaaag atcagagcaa acgcaacagc atgttttgct ttcgcccggc gaaagataaa    600
ctgtttgaaa actataccta tctgagcaaa aacgtggtgg ataactggga agaagtgtgc    660
ccgcgcaaaa acctggaaaa cgcgaaattt ggcctgtggg tggatggcaa ctgcgaagat    720
attccgcatg tgaacgaatt tagcgcgaac gatctgtttg aatgcaacaa actggtgttt    780
gaactgagcg cgagcgatca gccgaaacag tatgaacagc atctgaccga ttatgaaaaa    840
attaaagaag cttttaaaaa caaaaacgcg agcatgatta aaagcgcgtt tctgccgacc    900 ggcgcgtttta aagcggatcg ctataaaagc catggcaaag gctataactg gggcaactat    960
aaccgcgaaa cccagaaatg cgaaattttt aacgtgaaac cgacctgcct gattaacaac    1020
agcagctata ttgcgaccac cgcgctgagc catccgattg aagtggaaca taactttccg    1080
tgcagcctgt ataaagatga aattaaaaaa gaaattgaac gcgaaagcaa acgcattaaa    1140
ctgaacgata acgatgatga aggcaacaaa aaaattattg cgccgcgcat ttttattagc    1200
gatgataaag atagcctgaa atgcccgtgc gatccggaaa tggtgagcaa cagcacctgc    1260
cgctttttgt gtgcaaatg cgtggaacgc cgcgcggaag tgaccagcaa caacgaagtg    1320
gtggtgaaag aagaatataa agatgaa                                        1347
```

<210> SEQ ID NO 14
<211> LENGTH: 449
<212> TYPE: PRT
<213> ORGANISM: Artificial Sequence
<220> FEATURE:
<223> OTHER INFORMATION: chimeric protein AMA-1: FVO(D1)+ 3D7 (D2+3)

<400> SEQUENCE: 14

```
Gly Ala Glu Pro Ala Pro Gln Glu Gln Asn Leu Phe Pro Ser Ile Glu
1               5                   10                  15

Ile Val Glu Arg Ser Asn Tyr Met Gly Asn Pro Trp Thr Glu Tyr Met
            20                  25                  30

Ala Lys Tyr Asp Ile Glu Val His Gly Ser Gly Ile Arg Val Asp
        35                  40                  45

Leu Gly Glu Asp Ala Glu Val Ala Gly Thr Gln Tyr Arg Leu Pro Ser
    50                  55                  60

Gly Lys Cys Pro Val Phe Gly Lys Gly Ile Ile Ile Glu Asn Ser Asn
65                  70                  75                  80

Thr Thr Phe Leu Lys Pro Val Ala Thr Gly Asn Gln Asp Leu Lys Asp
            85                  90                  95

Gly Gly Phe Ala Phe Pro Pro Thr Asn Pro Leu Ile Ser Pro Met Thr
        100                 105                 110

Leu Asn Gly Met Arg Asp Phe Tyr Lys Asn Asn Glu Tyr Val Lys Asn
    115                 120                 125

Leu Asp Glu Leu Thr Leu Cys Ser Arg His Ala Gly Asn Met Asn Pro
130                 135                 140

Asp Asn Asp Lys Asn Ser Asn Tyr Lys Tyr Pro Ala Val Tyr Asp Tyr
145                 150                 155                 160

Asn Asp Lys Lys Cys His Ile Leu Tyr Ile Ala Ala Gln Glu Asn Asn
            165                 170                 175

Gly Pro Arg Tyr Cys Asn Lys Asp Gln Ser Lys Arg Asn Ser Met Phe
        180                 185                 190

Cys Phe Arg Pro Ala Lys Asp Lys Leu Phe Glu Asn Tyr Thr Tyr Leu
    195                 200                 205

Ser Lys Asn Val Val Asp Asn Trp Glu Glu Val Cys Pro Arg Lys Asn
210                 215                 220

Leu Gln Asn Ala Lys Phe Gly Leu Trp Val Asp Gly Asn Cys Glu Asp
225                 230                 235                 240

Ile Pro His Val Asn Glu Phe Pro Ala Ile Asp Leu Phe Glu Cys Asn
            245                 250                 255

Lys Leu Val Phe Glu Leu Ser Ala Ser Asp Gln Pro Lys Gln Tyr Glu
        260                 265                 270

Gln His Leu Thr Asp Tyr Glu Lys Ile Lys Glu Gly Phe Lys Asn Lys
    275                 280                 285

Asn Ala Ser Met Ile Lys Ser Ala Phe Leu Pro Thr Gly Ala Phe Lys
290                 295                 300

Ala Asp Arg Tyr Lys Ser His Gly Lys Gly Tyr Asn Trp Gly Asn Tyr
305                 310                 315                 320

Asn Thr Glu Thr Gln Lys Cys Glu Ile Phe Asn Val Lys Pro Thr Cys
            325                 330                 335

Leu Ile Asn Asn Ser Ser Tyr Ile Ala Thr Thr Ala Leu Ser His Pro
        340                 345                 350

Ile Glu Val Glu Asn Asn Phe Pro Cys Ser Leu Tyr Lys Asp Glu Ile
    355                 360                 365

Met Lys Glu Ile Glu Arg Glu Ser Lys Arg Ile Lys Leu Asn Asp Asn
370                 375                 380

Asp Asp Glu Gly Asn Lys Lys Ile Ile Ala Pro Arg Ile Phe Ile Ser
385                 390                 395                 400
```

Asp Asp Lys Asp Ser Leu Lys Cys Pro Cys Asp Pro Glu Met Val Ser
            405                 410                 415

Asn Ser Thr Cys Arg Phe Phe Val Cys Lys Cys Val Glu Arg Arg Ala
            420                 425                 430

Glu Val Thr Ser Asn Asn Glu Val Val Val Lys Glu Glu Tyr Lys Asp
            435                 440                 445

Glu

<210> SEQ ID NO 15
<211> LENGTH: 1343
<212> TYPE: DNA
<213> ORGANISM: Artificial Sequence
<220> FEATURE:
<223> OTHER INFORMATION: nucleic acid sequence of chimeric protein
      AMA-1: FVO(D1)+ 3D7 (D2+3)

<400> SEQUENCE: 15

| | | |
|---|---|---|
| ggcgcggaac cggcgccgca ggaacagaac ctgtttccga gcattgaaat tgtggaacgc | 60 |
| agcaactata tgggcaaccc gtggaccgaa tatatggcga aatatgatat tgaagaagtg | 120 |
| catggcagcg gcattcgcgt ggatctgggc gaagatgcgg aagtggcggg cacccagtat | 180 |
| cgcctgccga gcggcaaatg cccggtgttt ggcaaaggca ttattattga aacagcaac | 240 |
| accacctttc tgaaaccggt ggcgaccggc aaccaggatc tgaaagatgg cggctttgcg | 300 |
| tttccgccga ccaacccgct gattagcccg atgaccctga cggcatgcg cgatttttat | 360 |
| aaaaacaacg aatatgtgaa aaacctggat gaactgaccc tgtgcagccg ccatgcgggc | 420 |
| aacatgaacc cggataacga taaaaacagc aactataaat atccggcggt gtatgattat | 480 |
| aacgataaaa aatgccatat tctgtatatt gcggcgcagg aaaacaacgg cccgcgctat | 540 |
| tgcaacaaag atcagagcat acgcaacagc atgtttttgct ttcgcccggc gaaagataaa | 600 |
| ctgtttgaaa actataccta tctgagcaaa acgtggtgg ataactggga agaagtgtgc | 660 |
| ccgcgtaaaa acctggaaaa cgcgaaattt ggcctgtggg tggatggcaa ctgcgaagat | 720 |
| attccgcatg tgaacgaatt tagcgcgaac gatctgtttg aatgcaacaa actggtgttt | 780 |
| gaactgagcg cgagcgatca gccgaaacag tatgaacagc atctgaccga ttatgaaaaa | 840 |
| attaagaag ctttaaaaa caaaaacgcg agcatgatta aagcgcgtt tctgccgacc | 900 |
| ggcgcgttta agcggatcg ttataaagc cacggcaaag ctataactg ggcaactat | 960 |
| aacaccgaaa cccagaaatg cgaaattttt aacgtgaaac cgacctgcct gattaacaac | 1020 |
| agcagctata ttgcgaccac cgcgctgagc catccgattg aagtggaaaa caactttccg | 1080 |
| tgcagcctgt ataaagatga aattatgaaa gaaattgaac gtgaaagcaa acgtattaaa | 1140 |
| ctgaacgata cgatgatga aggcaacaaa aaaattattg cgccgcgtat ttttattagc | 1200 |
| gatgataaag atagcctgaa atgcccgtgc gatccggaaa tggtgagcaa cagcacctgc | 1260 |
| cgttttttg tgtgcaaatg cgtggaacgt cgtgcggaag tgaccagcaa caacgaagtg | 1320 |
| gtggtgaaag aagaatataa aga | 1343 |

<210> SEQ ID NO 16
<211> LENGTH: 449
<212> TYPE: PRT
<213> ORGANISM: Artificial Sequence
<220> FEATURE:
<223> OTHER INFORMATION: chimeric protein of AMA-1: HB3(D1) + W2(D2+3)

<400> SEQUENCE: 16

```
Gly Ala Glu Pro Ala Pro Gln Glu Gln Asn Leu Phe Ser Ser Ile Glu
1               5                   10                  15

Ile Val Glu Arg Ser Asn Tyr Met Gly Asn Pro Trp Thr Glu Tyr Met
            20                  25                  30

Ala Lys Tyr Asp Ile Glu Lys Val His Gly Ser Gly Ile Arg Val Asp
        35                  40                  45

Leu Gly Glu Asp Ala Glu Val Ala Gly Thr Gln Tyr Arg Leu Pro Ser
    50                  55                  60

Gly Lys Cys Pro Val Phe Gly Lys Gly Ile Ile Glu Asn Ser Lys
65                  70                  75                  80

Thr Thr Phe Leu Thr Pro Val Ala Thr Glu Asn Gln Asp Leu Lys Asp
                85                  90                  95

Gly Gly Phe Ala Phe Pro Pro Thr Glu Pro Leu Ile Ser Pro Met Thr
            100                 105                 110

Leu Asp Gln Met Arg His Leu Tyr Lys Asp Asn Glu Tyr Val Lys Asn
        115                 120                 125

Leu Asp Glu Leu Thr Leu Cys Ser Arg His Ala Gly Asn Met Asn Pro
    130                 135                 140

Asp Asn Asp Lys Asn Ser Asn Tyr Lys Tyr Pro Ala Val Tyr Asp Tyr
145                 150                 155                 160

Glu Asp Lys Lys Cys His Ile Leu Tyr Ile Ala Ala Gln Glu Asn Asn
                165                 170                 175

Gly Pro Arg Tyr Cys Asn Lys Asp Glu Ser Lys Arg Asn Ser Met Phe
            180                 185                 190

Cys Phe Arg Pro Ala Lys Asp Lys Leu Phe Glu Asn Tyr Thr Tyr Leu
        195                 200                 205

Ser Lys Asn Val Val Asp Asn Trp Glu Glu Val Cys Pro Arg Lys Asn
    210                 215                 220

Leu Glu Asn Ala Lys Phe Gly Leu Trp Val Asp Gly Asn Cys Glu Asp
225                 230                 235                 240

Ile Pro His Val Asn Glu Phe Ser Ala Asn Asp Leu Phe Glu Cys Asn
                245                 250                 255

Lys Leu Val Phe Glu Leu Ser Ala Ser Asp Gln Pro Lys Gln Tyr Glu
            260                 265                 270

Gln His Leu Thr Asp Tyr Glu Lys Ile Lys Glu Gly Phe Lys Asn Lys
        275                 280                 285

Asn Ala Ser Met Ile Lys Ser Ala Phe Leu Pro Thr Gly Ala Phe Lys
    290                 295                 300

Ala Asp Arg Tyr Lys Ser His Gly Lys Gly Tyr Asn Trp Gly Asn Tyr
305                 310                 315                 320

Asn Arg Lys Thr Gln Lys Cys Glu Ile Phe Asn Val Lys Pro Thr Cys
                325                 330                 335

Leu Ile Asn Asn Ser Ser Tyr Ile Ala Thr Thr Ala Leu Ser His Pro
            340                 345                 350

Ile Glu Val Glu His Asn Phe Pro Cys Ser Leu Tyr Lys Asp Glu Ile
        355                 360                 365

Lys Lys Glu Ile Glu Arg Glu Ser Lys Arg Ile Lys Leu Asn Asp Asn
    370                 375                 380

Asp Asp Glu Gly Asn Lys Lys Ile Ile Ala Pro Arg Ile Phe Ile Ser
385                 390                 395                 400

Asp Asp Ile Asp Ser Leu Lys Cys Pro Cys Asp Pro Glu Ile Val Ser
                405                 410                 415

Asn Ser Thr Cys Asn Phe Phe Val Cys Lys Cys Val Glu Lys Arg Ala
```

Glu Val Thr Ser Asn Asn Glu Val Val Lys Glu Glu Tyr Lys Asp
    420             425             430
Glu
    435             440             445

<210> SEQ ID NO 17
<211> LENGTH: 1347
<212> TYPE: DNA
<213> ORGANISM: Artificial Sequence
<220> FEATURE:
<223> OTHER INFORMATION: nucleotide sequence of chimeric protein of
      AMA-1: HB3(D1) + W2(D2+3)

<400> SEQUENCE: 17

```
ggcgcagaac cagcacctca agagcaaaac ctgtttagca gcattgagat cgtggagcgt      60
tctaactaca tgggtaatcc ttggacggag tatatggcca agtatgacat cgaaaaggtg     120
catggtagcg gtattcgtgt tgacctgggt gaggacgcgg aggttgccgg cactcaatac     180
cgtctgccga gcggtaaatg tccggttttt ggcaagggta tcattatcga gaattcgaaa     240
accacctttt tgaccccggt ggctacggaa atcaggatc tgaaagacgg cggtttcgca     300
ttcccgccga ctgaacctct gatcagcccg atgacgctgg accagatgcg tcatttgtat     360
aaggataacg aatacgtgaa aaacttggac gaactgaccc tgtgcagccg tcacgccggt     420
aacatgaacc cggataatga caaaaacagc aactacaagt atccggcggt ttatgactac     480
gaggacaaaa agtgtcacat tctgtacatc gctgcgcagg aaaacaatgg ccctcgctac     540
tgcaataagg acgagtccaa gcgcaatagc atgttttgtt ccgtccggc caaggacaag     600
ctgttcgaga actatacca cctgtcgaaa acgtggttg acaactggga agaagtttgt     660
ccgcgtaaga acctggaaaa cgcgaagttc ggcctgtggg ttgatggtaa ctgtgaggac     720
atcccgcacg tcaacgagtt ctcggcaaac gatctgtttg agtgcaacaa actggttttt     780
gaactgagcg cgagcgacca gccgaaacag tatgagcagc acctgacgga ttacgaaaag     840
atcaaagaag gttttcaagaa caagaacgcc tccatgatca gtctgcatt cttgccgact     900
ggcgcgttta aggcggaccg ctacaagtct catggtaaag ctacaactg ggcaattac     960
aaccgcaaaa cccagaaatg cgagattttc aacgttaagc cgacgtgtct gatcaataac    1020
agctcgtaca tcgcgaccac ggcgctgagc catccgatcg aggttgaaca caactttccg    1080
tgtagcctgt acaaagatga gatcaagaaa gagatcgaac gtgaaagcaa gcgcattaag    1140
ctgaacgata cgacgacga gggcaataag aagattatcg cccctcgtat cttcattagc    1200
gatgacatcg actccctgaa atgcccgtgc gatccggaaa ttgtcagcaa tagcacgtgc    1260
aacttcttg tgtgtaagtg cgtcgagaaa cgtgcggaag ttacctccaa caatgaggtc    1320
gtggtgaaag aagagtataa ggatgag                                        1347
```

<210> SEQ ID NO 18
<211> LENGTH: 449
<212> TYPE: PRT
<213> ORGANISM: Artificial Sequence
<220> FEATURE:
<223> OTHER INFORMATION: Amino acid sequence chimeric protein of AMA-1
      W2(D1) + HB3 (D2+3)

<400> SEQUENCE: 18

Gly Ala Glu Pro Ala Pro Gln Glu Gln Asn Leu Phe Ser Ser Ile Glu
1               5                   10                  15

Ile Val Glu Arg Ser Asn Tyr Met Gly Asn Pro Trp Thr Glu Tyr Met

```
            20                  25                  30
Ala Lys Tyr Asp Ile Glu Glu Val His Gly Ser Gly Ile Arg Val Asp
            35                  40                  45
Leu Gly Glu Asp Ala Glu Val Ala Gly Thr Gln Tyr Arg Leu Pro Ser
            50                  55                  60
Gly Lys Cys Pro Val Phe Gly Lys Gly Ile Ile Glu Asn Ser Asn
 65                  70                  75                  80
Thr Thr Phe Leu Thr Pro Val Ala Thr Gly Asn Gln Tyr Leu Lys Asp
                85                  90                  95
Gly Gly Phe Ala Phe Pro Pro Thr Lys Pro Leu Met Ser Pro Met Thr
            100                 105                 110
Leu Asp Asp Met Arg Leu Leu Tyr Lys Asp Asn Glu Asp Val Lys Asn
            115                 120                 125
Leu Asp Glu Leu Thr Leu Cys Ser Arg His Ala Gly Asn Met Asn Pro
            130                 135                 140
Asp Asn Asp Lys Asn Ser Asn Tyr Lys Tyr Pro Ala Val Tyr Asp Tyr
145                 150                 155                 160
Asn Asp Lys Lys Cys His Ile Leu Tyr Ile Ala Ala Gln Glu Asn Asn
                165                 170                 175
Gly Pro Arg Tyr Cys Asn Lys Asp Glu Ser Lys Arg Asn Ser Met Phe
            180                 185                 190
Cys Phe Arg Pro Ala Lys Asp Lys Ser Phe Gln Asn Tyr Thr Tyr Leu
            195                 200                 205
Ser Lys Asn Val Val Asp Asn Trp Glu Glu Val Cys Pro Arg Lys Asn
            210                 215                 220
Leu Glu Asn Ala Lys Phe Gly Leu Trp Val Asp Gly Asn Cys Glu Asp
225                 230                 235                 240
Ile Pro His Val Asn Glu Phe Ser Ala Asn Asp Leu Phe Glu Cys Asn
                245                 250                 255
Lys Leu Val Phe Glu Leu Ser Ala Ser Asp Gln Pro Lys Gln Tyr Glu
            260                 265                 270
Gln His Leu Thr Asp Tyr Glu Lys Ile Lys Glu Gly Phe Lys Asn Lys
            275                 280                 285
Asn Ala Ser Met Ile Lys Ser Ala Phe Leu Pro Thr Gly Ala Phe Lys
            290                 295                 300
Ala Asp Arg Tyr Lys Ser Arg Gly Lys Gly Tyr Asn Trp Gly Asn Tyr
305                 310                 315                 320
Asn Thr Glu Thr Gln Lys Cys Glu Ile Phe Asn Val Lys Pro Thr Cys
                325                 330                 335
Leu Ile Asn Asn Ser Ser Tyr Ile Ala Thr Thr Ala Leu Ser His Pro
            340                 345                 350
Asn Glu Val Glu Asn Asn Phe Pro Cys Ser Leu Tyr Lys Asp Glu Ile
            355                 360                 365
Lys Lys Glu Ile Glu Arg Glu Ser Lys Arg Ile Lys Leu Asn Asp Asn
            370                 375                 380
Asp Asp Glu Gly Asn Lys Lys Ile Ile Ala Pro Arg Ile Phe Ile Ser
385                 390                 395                 400
Asp Asp Lys Asp Ser Leu Lys Cys Pro Cys Asp Pro Glu Ile Val Ser
                405                 410                 415
Asn Ser Thr Cys Asn Phe Phe Val Cys Lys Cys Val Glu Lys Arg Ala
                420                 425                 430
Glu Val Thr Ser Asn Asn Glu Val Val Lys Glu Glu Tyr Lys Asp
            435                 440                 445
```

Glu

<210> SEQ ID NO 19
<211> LENGTH: 1350
<212> TYPE: DNA
<213> ORGANISM: Artificial Sequence
<220> FEATURE:
<223> OTHER INFORMATION: Nucleotide sequence chimeric protein of AMA-1
W2(D1) + HB3 (D2+3)

<400> SEQUENCE: 19

```
ggcgcagaac cagcacctca agagcaaaac ctgtttagca gcattgagat cgtggagcgt     60
tctaactaca tgggtaatcc ttggacggag tatatggcca agtatgacat cgaagaggtg    120
catggtagcg gtattcgtgt tgacctgggt gaggacgcgg aggttgccgg cactcaatac    180
cgtctgccga gcggtaaatg tccggttttt ggcaagggta tcattattga aaatagcaac    240
accacctttt tgaccccggt ggctacgggt aatcagtatc tcaaagacgg cggtttcgca    300
ttcccgccga ctaaacctct gatgagcccg atgacgctgg acgacatgcg tttgctgtat    360
aaagataacg aagatgtgaa aaacttagac gaactgaccc tgtgcagccg tcacgccggt    420
aatatgaacc cggataatga caaaaacagc aactacaagt atccggcggt ttatgactac    480
aacgacaaaa agtgtcacat tctgtacatc gctgcgcagg aaaacaatgg ccctcgctac    540
tgcaataaag acgagtccaa gcgcaatagc atgttttgtt tccgtccggc caaggacaag    600
agcttccaga actataccta cctgtcgaaa aatgtggttg acaactggga ggaagtttgt    660
ccgcgtaaaa acctggaaaa cgcgaagttc ggcctgtggg ttgatggtaa ctgtgaggac    720
atcccgcacg tcaacgagtt ctcggcaaac gatctgtttg agtgcaacaa actggttttt    780
gaactgagcg cgagcgacca gccgaaacag tatgagcagc acctgacgga ttacgaaaag    840
atcaaggaag gtttcaagaa caagaacgcc tccatgatca agtctgcatt tttgccgact    900
ggcgcgttta aggcggaccg ctacaagtct cgcggtaaag gctacaactg gggcaattac    960
aacaccgaaa cgcagaaatg cgagattttc aacgtaaagc cgacgtgtct gatcaataac   1020
agctcgtaca tcgcgaccac ggcgctgagc catccgaacg aggttgaaaa caattttcct   1080
tgtagcctgt acaaagatga gatcaagaaa gagatcgaac gtgaaagcaa gcgtattaag   1140
ctgaacgata acgacgacga gggcaataag aagattatcg cccctcgtat cttcattagc   1200
gatgacaaag actccctgaa atgcccgtgc gatccggaaa ttgtcagcaa tagcacgtgc   1260
aacttctttg tgtgtaagtg cgtcgagaaa cgtgcggaag ttacctccaa taatgaggtc   1320
gtggtgaagg aagagtataa ggatgagtga                                    1350
```

<210> SEQ ID NO 20
<211> LENGTH: 116
<212> TYPE: PRT
<213> ORGANISM: Artificial Sequence
<220> FEATURE:
<223> OTHER INFORMATION: Domain 2 region (from 3D7 sequence)

<400> SEQUENCE: 20

```
Pro Arg Lys Asn Leu Gln Asn Ala Lys Phe Gly Leu Trp Val Asp Gly
1               5                   10                  15

Asn Cys Glu Asp Ile Pro His Val Asn Glu Phe Pro Ala Ile Asp Leu
            20                  25                  30

Phe Glu Cys Asn Lys Leu Val Phe Glu Leu Ser Ala Ser Asp Gln Pro
        35                  40                  45
```

Lys Gln Tyr Glu Gln His Leu Thr Asp Tyr Glu Lys Ile Lys Glu Gly
    50                  55                  60

Phe Lys Asn Lys Asn Ala Ser Met Ile Lys Ser Ala Phe Leu Pro Thr
 65                 70                  75                  80

Gly Ala Phe Lys Ala Asp Arg Tyr Lys Ser His Gly Lys Gly Tyr Asn
                85                  90                  95

Trp Gly Asn Tyr Asn Thr Glu Thr Gln Lys Cys Glu Ile Phe Asn Val
                100                 105                 110

Lys Pro Thr Cys
        115

<210> SEQ ID NO 21
<211> LENGTH: 220
<212> TYPE: PRT
<213> ORGANISM: Artificial Sequence
<220> FEATURE:
<223> OTHER INFORMATION: Domain 1 region (from 3D7 sequence)

<400> SEQUENCE: 21

Gly Ala Glu Pro Ala Pro Gln Glu Gln Asn Leu Phe Ser Ser Ile Glu
 1               5                  10                  15

Ile Val Glu Arg Ser Asn Tyr Met Gly Asn Pro Trp Thr Glu Tyr Met
                20                  25                  30

Ala Lys Tyr Asp Ile Glu Glu Val His Gly Ser Gly Ile Arg Val Asp
            35                  40                  45

Leu Gly Glu Asp Ala Glu Val Ala Gly Thr Gln Tyr Arg Leu Pro Ser
    50                  55                  60

Gly Lys Cys Pro Val Phe Gly Lys Gly Ile Ile Glu Asn Ser Asn
 65                 70                  75                  80

Thr Thr Phe Leu Thr Pro Val Ala Thr Gly Asn Gln Tyr Leu Lys Asp
                85                  90                  95

Gly Gly Phe Ala Phe Pro Pro Thr Glu Pro Leu Met Ser Pro Met Thr
                100                 105                 110

Leu Asp Glu Met Arg His Phe Tyr Lys Asp Asn Lys Tyr Val Lys Asn
            115                 120                 125

Leu Asp Glu Leu Thr Leu Cys Ser Arg His Ala Gly Asn Met Ile Pro
    130                 135                 140

Asp Asn Asp Lys Asn Ser Asn Tyr Lys Tyr Pro Ala Val Tyr Asp Asp
145                 150                 155                 160

Lys Asp Lys Lys Cys His Ile Leu Tyr Ile Ala Ala Gln Glu Asn Asn
                165                 170                 175

Gly Pro Arg Tyr Cys Asn Lys Asp Glu Ser Lys Arg Asn Ser Met Phe
                180                 185                 190

Cys Phe Arg Pro Ala Lys Asp Ile Ser Phe Gln Asn Tyr Thr Tyr Leu
            195                 200                 205

Ser Lys Asn Val Val Asp Asn Trp Glu Lys Val Cys
    210                 215                 220

<210> SEQ ID NO 22
<211> LENGTH: 449
<212> TYPE: PRT
<213> ORGANISM: Artificial Sequence
<220> FEATURE:
<223> OTHER INFORMATION: Amino acid sequence of M24 AMA1

<400> SEQUENCE: 22

Gly Ala Glu Pro Ala Pro Gln Glu Gln Asn Leu Phe Ser Ser Ile Glu
 1               5                  10                  15

-continued

```
Ile Val Glu Arg Ser Asn Tyr Met Gly Asn Pro Trp Thr Glu Tyr Met
                 20                  25                  30
Ala Lys Tyr Asp Ile Glu Val His Gly Ser Gly Ile Arg Val Asp
             35                  40                  45
Leu Gly Glu Asp Ala Val Ala Gly Thr Gln Tyr Arg Leu Pro Ser
     50                  55                  60
Gly Lys Cys Pro Val Phe Gly Lys Gly Ile Ile Ile Glu Asn Ser Asn
65                  70                  75                  80
Thr Thr Phe Leu Thr Pro Val Ala Thr Glu Asn Gln Asp Leu Lys Asp
                 85                  90                  95
Gly Gly Phe Ala Phe Pro Pro Thr Lys Pro Leu Met Ser Pro Met Thr
             100                 105                 110
Leu Asp Gln Met Arg Asp Phe Tyr Lys Asn Asn Glu Tyr Val Lys Asn
             115                 120                 125
Leu Asp Glu Leu Thr Leu Cys Ser Arg His Ala Gly Asn Met Asn Pro
     130                 135                 140
Asp Asn Asp Glu Asn Ser Asn Tyr Lys Tyr Pro Ala Val Tyr Asp Tyr
145                 150                 155                 160
Lys Asp Lys Lys Cys His Ile Leu Tyr Ile Ala Ala Gln Glu Asn Asn
                 165                 170                 175
Gly Pro Arg Tyr Cys Asn Lys Asp Gln Ser Lys Arg Asn Ser Met Phe
             180                 185                 190
Cys Phe Arg Pro Ala Lys Asp Lys Leu Phe Glu Asn Tyr Thr Tyr Leu
         195                 200                 205
Ser Lys Asn Val Val His Asn Trp Glu Lys Val Cys Pro Arg Lys Asn
     210                 215                 220
Leu Gln Asn Ala Lys Phe Gly Leu Trp Val Asp Gly Asn Cys Glu Asp
225                 230                 235                 240
Ile Pro His Val Asn Glu Phe Ser Ala Asn Asp Leu Phe Glu Cys Asn
                 245                 250                 255
Lys Leu Val Phe Glu Leu Ser Ala Ser Asp Gln Pro Lys Gln Tyr Glu
             260                 265                 270
Gln His Leu Thr Asp Tyr Glu Lys Ile Lys Glu Gly Phe Lys Asn Lys
         275                 280                 285
Asn Ala Ser Met Ile Lys Ser Ala Phe Leu Pro Thr Gly Ala Phe Lys
     290                 295                 300
Ala Asp Arg Tyr Lys Ser Arg Gly Lys Gly Tyr Asn Trp Gly Asn Tyr
305                 310                 315                 320
Asn Thr Lys Thr Gln Lys Cys Glu Ile Phe Asn Val Lys Pro Thr Cys
                 325                 330                 335
Leu Ile Asn Asn Ser Ser Tyr Ile Ala Thr Thr Ala Leu Ser His Pro
             340                 345                 350
Ile Glu Val Glu His Asn Phe Pro Cys Ser Leu Tyr Lys Asp Glu Ile
         355                 360                 365
Lys Lys Glu Ile Glu Arg Glu Ser Lys Arg Ile Lys Leu Asn Asp Asn
     370                 375                 380
Asp Asp Glu Gly Asn Lys Lys Ile Ile Ala Pro Arg Ile Phe Ile Ser
385                 390                 395                 400
Asp Asp Ile Asp Ser Leu Lys Cys Pro Cys Asp Pro Glu Met Val Ser
                 405                 410                 415
Asn Ser Thr Cys Arg Phe Tyr Val Cys Lys Cys Val Glu Arg Arg Ala
             420                 425                 430
```

```
Glu Val Thr Ser Asn Asn Glu Val Val Lys Glu Tyr Lys Asp
        435                 440                 445

Glu

<210> SEQ ID NO 23
<211> LENGTH: 449
<212> TYPE: PRT
<213> ORGANISM: Artificial Sequence
<220> FEATURE:
<223> OTHER INFORMATION: Amino acid sequence of 102-1 AMA1

<400> SEQUENCE: 23

Gly Ala Glu Pro Ala Pro Gln Glu Gln Asn Leu Phe Ser Ser Ile Glu
1               5                   10                  15

Ile Val Glu Arg Ser Asn Tyr Met Gly Asn Pro Trp Thr Glu Tyr Met
            20                  25                  30

Ala Lys Tyr Asp Ile Glu Glu Val His Gly Ser Gly Ile Arg Val Asp
        35                  40                  45

Leu Gly Glu Asp Ala Glu Val Ala Gly Thr Gln Tyr Arg Leu Pro Ser
    50                  55                  60

Gly Lys Cys Pro Val Phe Gly Lys Gly Ile Ile Ile Glu Asn Ser Asn
65                  70                  75                  80

Thr Thr Phe Leu Thr Pro Val Ala Thr Glu Asn Lys Asp Leu Lys Asp
                85                  90                  95

Gly Gly Phe Ala Phe Pro Pro Thr Glu Pro Leu Met Ser Pro Met Thr
            100                 105                 110

Leu Asp Asp Met Arg Arg Phe Tyr Lys Asp Asn Glu Tyr Val Lys Asn
        115                 120                 125

Leu Asp Glu Leu Thr Leu Cys Ser Arg His Ala Gly Asn Met Asn Pro
    130                 135                 140

Asp Asn Asp Lys Asn Ser Asn Tyr Lys Tyr Pro Ala Val Tyr Asp Tyr
145                 150                 155                 160

Asn Asp Lys Lys Cys His Ile Leu Tyr Ile Ala Ala Gln Glu Asn Asn
                165                 170                 175

Gly Pro Arg Tyr Cys Asn Lys Asp Gln Ser Lys Arg Asn Ser Met Phe
            180                 185                 190

Cys Phe Arg Pro Ala Lys Asp Lys Leu Phe Glu Asn Tyr Thr Tyr Leu
        195                 200                 205

Ser Lys Asn Val Val Asp Asn Trp Glu Glu Val Cys Pro Arg Lys Asn
    210                 215                 220

Leu Glu Asn Ala Lys Phe Gly Leu Trp Val Asp Gly Asn Cys Glu Asp
225                 230                 235                 240

Ile Pro His Val Asn Glu Phe Ser Ala Asn Asp Leu Phe Glu Cys Asn
                245                 250                 255

Lys Leu Val Phe Glu Leu Ser Ala Ser Asp Gln Pro Lys Gln Tyr Glu
            260                 265                 270

Gln His Leu Thr Asp Tyr Glu Lys Ile Lys Glu Gly Phe Lys Asn Lys
        275                 280                 285

Asn Ala Ser Met Ile Lys Ser Ala Phe Leu Pro Thr Gly Ala Phe Lys
    290                 295                 300

Ala Asp Arg Tyr Lys Ser His Gly Lys Gly Tyr Asn Trp Gly Asn Tyr
305                 310                 315                 320

Asn Arg Glu Thr Gln Lys Cys Glu Ile Phe Asn Val Lys Pro Thr Cys
                325                 330                 335

Leu Ile Asn Asn Ser Ser Tyr Ile Ala Thr Thr Ala Leu Ser His Pro
```

```
                     340               345               350
Asn Glu Val Glu His Asn Phe Pro Cys Ser Leu Tyr Lys Asp Glu Ile
            355               360               365
Lys Lys Glu Ile Glu Arg Glu Ser Lys Arg Ile Lys Leu Asn Asp Asn
        370               375               380
Asp Asp Glu Gly Asn Lys Lys Ile Ile Ala Pro Arg Ile Phe Ile Ser
385               390               395               400
Asp Asp Ile Asp Ser Leu Lys Cys Pro Cys Asp Pro Glu Ile Val Ser
                405               410               415
Asn Ser Thr Cys Asn Phe Phe Val Cys Lys Cys Val Glu Lys Arg Ala
            420               425               430
Glu Val Thr Ser Asn Asn Glu Val Val Lys Glu Glu Tyr Lys Asp
        435               440               445
Glu

<210> SEQ ID NO 24
<211> LENGTH: 1347
<212> TYPE: DNA
<213> ORGANISM: Artificial Sequence
<220> FEATURE:
<223> OTHER INFORMATION: Nucleic acid sequence of 3D7 AMA-1 protein

<400> SEQUENCE: 24
ggggcggaac cggcgccgca ggaacagaac ctgtttagca gcattgaaat tgtggaacgt      60
agcaactata tgggcaaccc gtggaccgaa tatatggcga aatatgatat tgaagaagtg     120
catggcagcg gcattcgtgt ggatctgggc gaagatgcgg aagtggcggg cacccagtat     180
cgtctgccga gcggcaaatg cccggtgttt ggcaaaggca ttattattga aaacagcaac     240
accacctttc tgaccccggt ggcgaccggc aaccagtatc tgaaagatgg cggctttgcg     300
tttccgccga ccgaaccgct gatgagcccg atgaccctgg atgaaatgcg tcattttat     360
aaagataaca aatatgtgaa aaacctggat gaactgaccc tgtgcagccg tcatgcgggc     420
aacatgattc cggataacga taaaaacagc aactataaat atccggcggt gtatgatgat     480
aaagataaaa aatgccatat tctgtatatt gcggcgcagg aaaacaacgg cccgcgttat     540
tgcaacaaag atgaaagcaa acgtaacagc atgttttgct ttcgtccggc gaaagatatt     600
agctttcaga actatacca tctgagcaaa acgtggtgg ataactggga aaaagtgtgc     660
ccgcgtaaaa acctgcagaa cgcgaaattt ggcctgtggg tggatggcaa ctgcgaagat     720
attccgcatg tgaacgaatt ccggcgatt gatctgtttg aatgcaacaa actggtgttt     780
gaactgagcg cgagcgatca gccgaaacag tatgaacagc atctgaccga ttatgaaaaa     840
attaaagaag ctttaaaaa caaaaacgcg agcatgatta aagcgcgtt tctgccgacc     900
ggcgcgttta agcggatcg ttataaaagc cacggcaaag ctataactg gggcaactat     960
aacaccgaaa cccagaaatg cgaaatttt aacgtgaaac cgacctgcct gattaacaac    1020
agcagctata ttgcgaccac cgcgctgagc catccgattg aagtggaaaa caactttccg    1080
tgcagcctgt ataaagatga aatcatgaaa gaaattgaac gtgaaagcaa acgtattaaa    1140
ctgaacgata cgatgatga aggcaacaaa aaaattattg cgccgcgtat ttttattagc    1200
gatgataaag atagcctgaa atgcccgtgc gatccggaaa tggtgagcaa cagcacctgc    1260
cgttttttg tgtgcaaatg cgtggaacgt cgtgcggaag tgaccagcaa caacgaagtg    1320
gtggtgaaag aagaatataa agatgaa                                       1347
```

```
<210> SEQ ID NO 25
<211> LENGTH: 371
<212> TYPE: DNA
<213> ORGANISM: Artificial Sequence
<220> FEATURE:
<223> OTHER INFORMATION: Monoclonal 1B10 Heavy Chain DNA Sequence

<400> SEQUENCE: 25
gaggtgcagc tgcaggagtc tggacctggc ctagtgcggc cctcacagag cctgtccatc      60
acctgcacag tctctggttt ctcattacct ctctatggtg ttcactgggt tcgccagtct     120
ccaggaaagg gtctggagtg gctgggagtc atatggagtg ggggaagcac agactataat     180
gcagctttcg tctccagact gagcatcagc aaggacaatt ccaagagcca agttttcttt     240
gaaatgaaca gtctgcaagc tgatgacaca gccacatatt actgtgccag aaataatggt     300
tactacgttg atgctatgga ctattggggt caaggaacct cagtcaccgt ctcctcagcc     360
aaaacaacac c                                                          371

<210> SEQ ID NO 26
<211> LENGTH: 121
<212> TYPE: PRT
<213> ORGANISM: Artificial Sequence
<220> FEATURE:
<223> OTHER INFORMATION: Monoclonal 1B10 Heavy Chain Protein Sequence

<400> SEQUENCE: 26

Glu Val Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Asn Met Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Thr Asp Tyr Asn Ala Ala Phe Ile
    50                  55                  60

Ser Arg Leu Ser Ile Asn Arg Asp Asn Ser Lys Ser Gln Val Phe Phe
65                  70                  75                  80

Lys Met Asn Ser Leu Gln Thr Asp Asp Thr Ala Ile Tyr Tyr Cys Val
                85                  90                  95

Arg Asn Asn Gly Tyr Tyr Val Asp Ala Met Asp Tyr Trp Gly Gln Gly
            100                 105                 110

Thr Ser Val Ala Val Ser Ser Ala Lys
        115                 120

<210> SEQ ID NO 27
<211> LENGTH: 8
<212> TYPE: PRT
<213> ORGANISM: Artificial Sequence
<220> FEATURE:
<223> OTHER INFORMATION: Monoclonal 1B10 VH CDR1

<400> SEQUENCE: 27

Gly Phe Ser Leu Asn Met Tyr Gly
1               5

<210> SEQ ID NO 28
<211> LENGTH: 7
<212> TYPE: PRT
<213> ORGANISM: Artificial Sequence
<220> FEATURE:
<223> OTHER INFORMATION: Monoclonal 1B10 VH CDR2

<400> SEQUENCE: 28
```

```
Ile Trp Ser Gly Gly Thr Thr
1               5
```

<210> SEQ ID NO 29
<211> LENGTH: 13
<212> TYPE: PRT
<213> ORGANISM: Artificial Sequence
<220> FEATURE:
<223> OTHER INFORMATION: Monoclonal 1B10 VH CDR3

<400> SEQUENCE: 29

```
Val Arg Asn Asn Gly Tyr Tyr Val Asp Ala Met Asp Tyr
1               5                   10
```

<210> SEQ ID NO 30
<211> LENGTH: 343
<212> TYPE: DNA
<213> ORGANISM: Artificial Sequence
<220> FEATURE:
<223> OTHER INFORMATION: Monoclonal 1B10 Light Chain DNA Sequence

<400> SEQUENCE: 30

```
gatgttgtga tgacccagac tccactctcc ctgcctgtca gtcttggaga tcaagcctcc      60
atctcttgca gatctagtca gagccttgta cacagtaatg gcaacaccta tttacattgg    120
tacctgcaga ggccaggcca gtctccaaag ctcctgatct acaaagtttc caaccgattt    180
tctggggtcc cagacaggtt cagtggcagt ggatcgggga cagatttcac actcaagatc    240
agcagagtgg aggctgagga tctgggagtt tatttctgct ctcagagtac acttggtccc    300
acgttcggag gggggaccaa gctggaaatg caacgggctg atg                      343
```

<210> SEQ ID NO 31
<211> LENGTH: 114
<212> TYPE: PRT
<213> ORGANISM: Artificial Sequence
<220> FEATURE:
<223> OTHER INFORMATION: Monoclonal 1B10 Light Chain Protein Sequence

<400> SEQUENCE: 31

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Leu Gly Pro Thr Phe Gly Gly Gly Thr Lys Leu Glu Met Gln Arg
            100                 105                 110

Ala Asp
```

<210> SEQ ID NO 32
<211> LENGTH: 11
<212> TYPE: PRT
<213> ORGANISM: Artificial Sequence
<220> FEATURE:
<223> OTHER INFORMATION: Monoclonal 1B10 VL CDR1

<400> SEQUENCE: 32

Gln Ser Leu Val His Ser Asn Gly Asn Thr Tyr
1               5                   10

<210> SEQ ID NO 33
<211> LENGTH: 3
<212> TYPE: PRT
<213> ORGANISM: Artificial Sequence
<220> FEATURE:
<223> OTHER INFORMATION: Monoclonal 1B10 VL CDR2

<400> SEQUENCE: 33

Lys Val Ser
1

<210> SEQ ID NO 34
<211> LENGTH: 8
<212> TYPE: PRT
<213> ORGANISM: Artificial Sequence
<220> FEATURE:
<223> OTHER INFORMATION: Monoclonal 1B10 VL CDR3

<400> SEQUENCE: 34

Ser Gln Ser Thr Leu Gly Pro Thr
1               5

<210> SEQ ID NO 35
<211> LENGTH: 371
<212> TYPE: DNA
<213> ORGANISM: Artificial Sequence
<220> FEATURE:
<223> OTHER INFORMATION: Monoclonal 4E11 Heavy Chain DNA sequence

<400> SEQUENCE: 35
gaggtgcagc tgcaggagtc tggacctggc ctagtgcggc cctcacagag cctgtccatc      60
acctgcacag tctctggttt ctcattacct ctctatggtg ttcactgggt tcgccagtct     120
ccaggaaagg gtctggagtg gctgggagtc atatggagtg ggggaagcac agactataat     180
gcagctttcg tctccagact gagcatcagc aaggacaatt ccaagagcca agttttcttt     240
gaaatgaaca gtctgcaagc tgatgacaca gccacatatt actgtgccag aaataatggt     300
tactacgttg atgctatgga ctattggggt caaggaacct cagtcaccgt ctcctcagcc     360
aaaacaacac c                                                          371

<210> SEQ ID NO 36
<211> LENGTH: 123
<212> TYPE: PRT
<213> ORGANISM: Artificial Sequence
<220> FEATURE:
<223> OTHER INFORMATION: Monoclonal 4E11 Heavy Chain Protein Sequence

<400> SEQUENCE: 36

Glu Val Gln Leu Gln Glu Ser Gly Pro Gly Leu Val Arg Pro Ser Gln
1               5                   10                  15

Ser Leu Ser Ile Thr Cys Thr Val Ser Gly Phe Ser Leu Pro Leu Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Val
    50                  55                  60

Ser Arg Leu Ser Ile Ser Lys Asp Asn Ser Lys Ser Gln Val Phe Phe

```
            65                  70                  75                  80
Glu Met Asn Ser Leu Gln Ala Asp Asp Thr Ala Thr Tyr Tyr Cys Ala
                    85                  90                  95
Arg Asn Asn Gly Tyr Tyr Val Asp Ala Met Asp Tyr Trp Gly Gln Gly
                100                 105                 110
Thr Ser Val Thr Val Ser Ser Ala Lys Thr Thr
        115                 120
```

<210> SEQ ID NO 37
<211> LENGTH: 8
<212> TYPE: PRT
<213> ORGANISM: Artificial Sequence
<220> FEATURE:
<223> OTHER INFORMATION: Monoclonal 4E11 VH CDR1

<400> SEQUENCE: 37

```
Gly Phe Ser Leu Pro Leu Tyr Gly
1               5
```

<210> SEQ ID NO 38
<211> LENGTH: 7
<212> TYPE: PRT
<213> ORGANISM: Artificial Sequence
<220> FEATURE:
<223> OTHER INFORMATION: Monoclonal 4E11 VH CDR2

<400> SEQUENCE: 38

```
Ile Trp Ser Gly Gly Ser Thr
1               5
```

<210> SEQ ID NO 39
<211> LENGTH: 13
<212> TYPE: PRT
<213> ORGANISM: Artificial Sequence
<220> FEATURE:
<223> OTHER INFORMATION: Monoclonal 4E11 VH CDR3

<400> SEQUENCE: 39

```
Ala Arg Asn Asn Gly Tyr Tyr Val Asp Ala Met Asp Tyr
1               5                   10
```

<210> SEQ ID NO 40
<211> LENGTH: 339
<212> TYPE: DNA
<213> ORGANISM: Artificial Sequence
<220> FEATURE:
<223> OTHER INFORMATION: Monoclonal 4E11 Light Chain DNA Sequence

<400> SEQUENCE: 40

```
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct tcaaagtttc caaccgattt     180
tctggggtcc cagacaggtt cagtggcagt ggatcaggga cagatttcac actccagatc     240
agcagagtgg aggctgagga tctgggattt tatttctgct cgcaaagtac acatgttccc     300
acgttcggag gggggaccaa actggaaata aaacgggct                            339
```

<210> SEQ ID NO 41
<211> LENGTH: 113
<212> TYPE: PRT
<213> ORGANISM: Artificial Sequence
<220> FEATURE:
<223> OTHER INFORMATION: Monoclonal 4E11 Light Chain Protein Sequence

<400> SEQUENCE: 41

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Gln Ile
65                  70                  75                  80

Ser Arg Val Glu Ala Glu Asp Leu Gly Phe Tyr Phe Cys Ser Gln Ser
                85                  90                  95

Thr His Val Pro Thr Phe Gly Gly Gly Thr Lys Leu Glu Ile Lys Arg
                100                 105                 110

Ala

<210> SEQ ID NO 42
<211> LENGTH: 11
<212> TYPE: PRT
<213> ORGANISM: Artificial Sequence
<220> FEATURE:
<223> OTHER INFORMATION: Monoclonal 4E11 VL CDR1

<400> SEQUENCE: 42

Gln Ser Leu Val His Ser Asn Gly Asn Thr Tyr
1               5                   10

<210> SEQ ID NO 43
<211> LENGTH: 3
<212> TYPE: PRT
<213> ORGANISM: Artificial Sequence
<220> FEATURE:
<223> OTHER INFORMATION: Monoclonal 4E11 VL CDR2

<400> SEQUENCE: 43

Lys Val Ser
1

<210> SEQ ID NO 44
<211> LENGTH: 8
<212> TYPE: PRT
<213> ORGANISM: Artificial Sequence
<220> FEATURE:
<223> OTHER INFORMATION: Monoclonal 4E11 VL CDR3

<400> SEQUENCE: 44

Ser Gln Ser Thr His Val Pro Thr
1               5

<210> SEQ ID NO 45
<211> LENGTH: 364
<212> TYPE: DNA
<213> ORGANISM: Artificial Sequence
<220> FEATURE:
<223> OTHER INFORMATION: Monoclonal 4E8 Heavy Chain DNA Sequence

<400> SEQUENCE: 45
gaggtgcagc tgcaggagtc tggacctggc ctggtgcagc cctcacagag cctgtccatc        60
acctgcacag tctctgattt ctcattaatt atgtatggtg tacattgggt tcgccagtct       120

```
ccgggaaagg gtctggagtg gctgggagtg atatggagtg gtggaagcac agactataat    180
gcagctttca tatccagact gagcatcagc aaggacaatt ccaagagcca agttttcttt    240
aaaatgaaca gtctgcaagc tgatgacaca gccatatatt actgtgccag aaataatggt    300
tactacgttg atgctatgga ctactggggt caaggaacct cagtcaccgt ctcctcagcc    360
aaaa                                                                  364
```

<210> SEQ ID NO 46
<211> LENGTH: 121
<212> TYPE: PRT
<213> ORGANISM: Artificial Sequence
<220> FEATURE:
<223> OTHER INFORMATION: Monoclonal 4E8 Heavy Chain Protein Sequence

<400> SEQUENCE: 46

```
Glu Val Gln Leu Gln Glu Ser Gly Pro Gly Leu Val Gln Pro Ser Gln
1               5                   10                  15

Ser Leu Ser Ile Thr Cys Thr Val Ser Asp Phe Ser Leu Ile Met Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Asn Gly Tyr Tyr Val Asp Ala Met Asp Tyr Trp Gly Gln Gly
            100                 105                 110

Thr Ser Val Thr Val Ser Ser Ala Lys
        115                 120
```

<210> SEQ ID NO 47
<211> LENGTH: 8
<212> TYPE: PRT
<213> ORGANISM: Artificial Sequence
<220> FEATURE:
<223> OTHER INFORMATION: Monoclonal 4E8 VH CDR1

<400> SEQUENCE: 47

```
Asp Phe Ser Leu Ile Met Tyr Gly
1               5
```

<210> SEQ ID NO 48
<211> LENGTH: 7
<212> TYPE: PRT
<213> ORGANISM: Artificial Sequence
<220> FEATURE:
<223> OTHER INFORMATION: Monoclonal 4E8 VH CDR2

<400> SEQUENCE: 48

```
Ile Trp Ser Gly Gly Ser Thr
1               5
```

<210> SEQ ID NO 49
<211> LENGTH: 13
<212> TYPE: PRT
<213> ORGANISM: Artificial Sequence
<220> FEATURE:
<223> OTHER INFORMATION: Monoclonal 4E8 VH CDR3

<400> SEQUENCE: 49

Ala Arg Asn Asn Gly Tyr Tyr Val Asp Ala Met Asp Tyr
1               5                   10

<210> SEQ ID NO 50
<211> LENGTH: 342
<212> TYPE: DNA
<213> ORGANISM: Artificial Sequence
<220> FEATURE:
<223> OTHER INFORMATION: Monoclonal 4E8 Light Chain DNA Sequence

<400> SEQUENCE: 50
gatgttgtga tgacccaaac tccactctcc ctgcctgtca gtcttggaga tcaagcctcc        60
atctcttgca gatctagtca gagccttgta cacaataatg gaaacaccta tttacattgg      120
tacctgcaga agccaggcca gtctccaaag ctcctgatct acaaagtttc caaccgattt      180
tttggggtcc cagacaggtt cagtggcagt ggatcaggga cagatttcac actcaagatc      240
agcagagtgg aggctgagga tctgggagtt tatttctgct ctcaaagtac acatgttccc      300
acgttcggag gggggaccaa gctggaaatc aaacgtaagt cg                          342

<210> SEQ ID NO 51
<211> LENGTH: 114
<212> TYPE: PRT
<213> ORGANISM: Artificial Sequence
<220> FEATURE:
<223> OTHER INFORMATION: Monoclonal 4E8 Light Chain Protein Sequence

<400> SEQUENCE: 51

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Gly Gly Thr Lys Leu Glu Ile Lys Arg
            100                 105                 110

Lys Ser

<210> SEQ ID NO 52
<211> LENGTH: 11
<212> TYPE: PRT
<213> ORGANISM: Artificial Sequence
<220> FEATURE:
<223> OTHER INFORMATION: Monoclonal 4E8 VL CDR1

<400> SEQUENCE: 52

Gln Ser Leu Val His Asn Asn Gly Asn Thr Tyr
1               5                   10

<210> SEQ ID NO 53
<211> LENGTH: 3
<212> TYPE: PRT
<213> ORGANISM: Artificial Sequence
<220> FEATURE:
<223> OTHER INFORMATION: Monoclonal 4E8 VL CDR2

<400> SEQUENCE: 53

Lys Val Ser
1

<210> SEQ ID NO 54
<211> LENGTH: 8
<212> TYPE: PRT
<213> ORGANISM: Artificial Sequence
<220> FEATURE:
<223> OTHER INFORMATION: Monoclonal 4E8 VL CDR3

<400> SEQUENCE: 54

Ser Gln Ser Thr His Val Pro Thr
1               5

<210> SEQ ID NO 55
<211> LENGTH: 375
<212> TYPE: DNA
<213> ORGANISM: Artificial Sequence
<220> FEATURE:
<223> OTHER INFORMATION: Monoclonal 1E10 Heavy Chain DNA sequence

<400> SEQUENCE: 55
gaggtgcagc tgcaggagtc tgggctgaa ttggcaaaac ctggggcctc agtgaagctg        60
tcctgcaagg cttctggcta cacctttact aactacttga tgcactggat aaaacaaagg      120
cctggacggt ctggaatgga ttggatacat taatcatggc agtggttata ctaactacaa      180
tcagaagttc attgacaggg ccacattgac tgcagacaaa tcctccagca cagcctacat      240
gcagctgcgc agctacatat gaggactctg cagtctatta ctgtgtccac gggtacttcg      300
atgtctgggg cacagggacc acggtcaccg tctcctcagc caaaacgaca cccccatctg      360
tctatccact ggccc                                                      375

<210> SEQ ID NO 56
<211> LENGTH: 126
<212> TYPE: PRT
<213> ORGANISM: Artificial Sequence
<220> FEATURE:
<223> OTHER INFORMATION: Monoclonal 1E10 Heavy Chain Protein Sequence

<400> SEQUENCE: 56

Glu Val Gln Leu Gln Glu Ser Gly Ala Glu Leu Ala Lys Pro Gly Ala
1               5                   10                  15

Ser Val Lys Leu Ser Cys Lys Ala Ser Gly Tyr Thr Phe Thr Asn Tyr
            20                  25                  30

Leu Met His Trp Ile Lys Gln Arg Pro Gly Gln Gly Leu Glu Trp Ile
        35                  40                  45

Gly Tyr Ile Asn His Gly Ser Gly Tyr Thr Asn Tyr Asn Gln Lys Phe
    50                  55                  60

Ile Asp Arg Ala Thr Leu Thr Ala Asp Lys Ser Ser Ser Thr Ala Tyr
65                  70                  75                  80

Met Gln Leu Arg Ser Leu Thr Tyr Glu Asp Ser Ala Val Tyr Tyr Cys
                85                  90                  95

Val His Gly Tyr Phe Asp Val Trp Gly Thr Gly Thr Thr Val Thr Val
            100                 105                 110

Ser Ser Ala Lys Thr Thr Pro Pro Ser Val Tyr Pro Leu Ala
        115                 120                 125

<210> SEQ ID NO 57

```
<211> LENGTH: 8
<212> TYPE: PRT
<213> ORGANISM: Artificial Sequence
<220> FEATURE:
<223> OTHER INFORMATION: Monoclonal 1E10 VH CDR1

<400> SEQUENCE: 57

Gly Tyr Thr Phe Thr Asn Tyr Leu
1               5

<210> SEQ ID NO 58
<211> LENGTH: 8
<212> TYPE: PRT
<213> ORGANISM: Artificial Sequence
<220> FEATURE:
<223> OTHER INFORMATION: Monoclonal 1E10 VH CDR2

<400> SEQUENCE: 58

Ile Asn His Gly Ser Gly Tyr Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Monoclonal 1E10 VH CDR3

<400> SEQUENCE: 59

Val His Gly Tyr Phe Asp Val
1               5

<210> SEQ ID NO 60
<211> LENGTH: 390
<212> TYPE: DNA
<213> ORGANISM: Artificial Sequence
<220> FEATURE:
<223> OTHER INFORMATION: Monoclonal 1E10 Light Chain DNA sequence

<400> SEQUENCE: 60
caagtgcaga ttttcagctt cctgctaatc agtgcctcag tcatactgtc cagaggacaa      60
attgttctca cccagtctcc aacaatcatg tctgcatctc caggggagaa ggtcaccatg     120
acctgcagtg ccagctcaag tgtaacttac atgcactggt accagcagaa gccaggcacc     180
tcccccaaaa gatggattta tgacacatcc aaactggcct ctggagtccc tgctcgcttc     240
agtggcagtg gtctgggac ctcttattct ctcacaatca gcagcatgga ggctgaagat     300
gctgccactt attactgcca tcagcggagt agttacccca cgttcggagg ggggaccaag     360
ctggaaatca aacgtaagtc gactgcacca                                      390

<210> SEQ ID NO 61
<211> LENGTH: 130
<212> TYPE: PRT
<213> ORGANISM: Artificial Sequence
<220> FEATURE:
<223> OTHER INFORMATION: Monoclonal 1E10 Light Chain Protein sequence

<400> SEQUENCE: 61

Gln Val Gln Ile Phe Ser Phe Leu Leu Ile Ser Ala Ser Val Ile Leu
1               5                   10                  15

Ser Arg Gly Gln Ile Val Leu Thr Gln Ser Pro Thr Ile Met Ser Ala
            20                  25                  30

Ser Pro Gly Glu Lys Val Thr Met Thr Cys Ser Ala Ser Ser Ser Val
        35                  40                  45
```

```
Thr Tyr Met His Trp Tyr Gln Gln Lys Pro Gly Thr Ser Pro Lys Arg
        50                  55                  60

Trp Ile Tyr Asp Thr Ser Lys Leu Ala Ser Gly Val Pro Ala Arg Phe
 65                  70                  75                  80

Ser Gly Ser Gly Ser Gly Thr Ser Tyr Ser Leu Thr Ile Ser Ser Met
                 85                  90                  95

Glu Ala Glu Asp Ala Ala Thr Tyr Tyr Cys His Gln Arg Ser Ser Tyr
            100                 105                 110

Pro Thr Phe Gly Gly Gly Thr Lys Leu Glu Ile Lys Arg Lys Ser Thr
        115                 120                 125

Ala Pro
    130

<210> SEQ ID NO 62
<211> LENGTH: 6
<212> TYPE: PRT
<213> ORGANISM: Artificial Sequence
<220> FEATURE:
<223> OTHER INFORMATION: Monoclonal 1E10 VL CDR1

<400> SEQUENCE: 62

Ser Ser Ser Val Thr Tyr
1               5

<210> SEQ ID NO 63
<211> LENGTH: 3
<212> TYPE: PRT
<213> ORGANISM: Artificial Sequence
<220> FEATURE:
<223> OTHER INFORMATION: Monoclonal 1E10 VL CDR2

<400> SEQUENCE: 63

Asp Thr Ser
1

<210> SEQ ID NO 64
<211> LENGTH: 8
<212> TYPE: PRT
<213> ORGANISM: Artificial Sequence
<220> FEATURE:
<223> OTHER INFORMATION: Monoclonal 1E10 VL CDR3

<400> SEQUENCE: 64

His Gln Arg Ser Ser Tyr Pro Thr
1               5

<210> SEQ ID NO 65
<211> LENGTH: 502
<212> TYPE: PRT
<213> ORGANISM: Plasmodium berghei

<400> SEQUENCE: 65

Met Lys Glu Ile Tyr Tyr Ile Leu Ile Leu Cys Ser Ile Tyr Leu Ile
1               5                   10                  15

Asn Leu Ser Asn Cys Ser Glu Gly Pro Asn Asn Val Ile Ser Glu Asn
            20                  25                  30

Gly His Ile Asn Tyr Asp Met Ile Gln Lys Glu Asn Thr Glu Arg Ser
        35                  40                  45

Thr Lys Leu Ile Asn Pro Trp Glu Lys Tyr Met Glu Lys Tyr Asp Ile
    50                  55                  60

Glu Lys Met His Gly Ser Gly Ile Arg Val Asp Leu Gly Glu Asp Ala
```

```
                65                  70                  75                  80
Arg Val Glu Asn Arg Asp Tyr Arg Ile Pro Ser Gly Lys Cys Pro Val
                    85                  90                  95
Ile Gly Lys Gly Ile Thr Ile Gln Asn Ser Glu Val Ser Phe Leu Thr
                100                 105                 110
Pro Val Ala Thr Gly Asp Gln Ser Val Arg Ser Gly Leu Ala Leu
                115                 120                 125
Pro Lys Thr Asp Val His Leu Ser Pro Ile Thr Ile Asp Asn Leu Lys
                130                 135                 140
Thr Met Tyr Lys Glu His Pro Glu Ile Val Lys Leu Asn Asn Met Ser
145                 150                 155                 160
Leu Cys Ala Lys His Thr Ser Phe Tyr Val Pro Gly Asn Asn Ala Asn
                165                 170                 175
Ser Ala Tyr Arg His Pro Ala Val Tyr Asp Lys Ser Asn Ser Thr Cys
                180                 185                 190
Tyr Met Leu Tyr Val Ala Ala Gln Glu Asn Met Gly Pro Arg Tyr Cys
                195                 200                 205
Ser Asn Asn Ala Asn Asn Asp Asn Gln Pro Phe Cys Phe Thr Pro Glu
                210                 215                 220
Lys Ile Glu Lys Tyr Lys Asn Leu Ser Tyr Leu Thr Lys Asn Leu Arg
225                 230                 235                 240
Asp Asp Trp Glu Thr Ser Cys Pro Asn Lys Ser Ile Lys Asn Ala Lys
                245                 250                 255
Phe Gly Ile Trp Val Asp Gly Tyr Cys Lys Asp Tyr Gln Lys His Thr
                260                 265                 270
Val His Asp Ser Asp Ser Leu Leu Lys Cys Asn Gln Ile Ile Phe Asn
                275                 280                 285
Glu Ser Ala Ser Asp Gln Pro Lys Gln Tyr Glu Lys His Leu Glu Asp
                290                 295                 300
Thr Thr Lys Phe Arg Gln Gly Val Ala Glu Arg Asn Gly Lys Leu Ile
305                 310                 315                 320
Gly Glu Ala Leu Leu Pro Ile Gly Ser Tyr Lys Ser Asp Gln Ile Lys
                325                 330                 335
Ser His Gly Arg Gly Tyr Asn Trp Gly Asn Tyr Asp Ser Gln Asn Lys
                340                 345                 350
Lys Cys Tyr Ile Phe Glu Thr Lys Pro Thr Cys Leu Ile Asn Asp Arg
                355                 360                 365
Asn Phe Ile Ala Thr Thr Ala Leu Ser Ser Thr Glu Glu Phe Glu Glu
                370                 375                 380
Gln Phe Pro Cys Asp Ile Tyr Lys Asn Lys Ile Asn Glu Glu Ile Lys
385                 390                 395                 400
Val Leu Asn Lys Asn Ile Ser Asn Gly Asn Asn Ser Ile Glu Phe Pro
                405                 410                 415
Arg Ile Phe Ile Ser Thr Asp Lys Asn Ser Leu Asn Cys Pro Cys Glu
                420                 425                 430
Pro Thr Gln Leu Thr Glu Ser Ser Cys Asn Phe Tyr Val Cys Asn Cys
                435                 440                 445
Val Glu Lys Arg Gln Tyr Ile Ala Glu Asn Asn Asp Val Glu Ile Lys
                450                 455                 460
Glu Glu Phe Arg Ser Glu Tyr Glu Ser Pro Ser Asn Gln Arg Val Ile
465                 470                 475                 480
Val Ile Ile Ile Phe Ile Cys Val Gly Ile Ile Leu Val Ile Leu Leu
                485                 490                 495
```

Val Gly Tyr Phe Phe Lys
            500

<210> SEQ ID NO 66
<211> LENGTH: 568
<212> TYPE: PRT
<213> ORGANISM: Plasmodium falciparum

<400> SEQUENCE: 66

Met Arg Lys Leu Tyr Cys Val Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
            35                  40                  45

Lys Glu Tyr Glu Tyr Pro Leu His Gln Glu His Thr Tyr Gln Gln Glu
        50                  55                  60

Asp Ser Gly Glu Asp Asn Thr Leu Gln His Ala Tyr Pro Ile Asp
65                  70                  75                  80

His Glu Gly Ala Glu Pro Ala Pro Gln Glu Gln Asn Leu Phe Ser Ser
                85                  90                  95

Ile Glu Ile Val Glu Arg Ser Asn Tyr Met Gly Asn Pro Trp Thr Glu
            100                 105                 110

Tyr Met Ala Lys Tyr Asp Ile Glu Glu Val His Gly Ser Gly Ile Arg
            115                 120                 125

Val Asp Leu Gly Glu Asp Ala Glu Val Ala Gly Thr Gln Tyr Arg Leu
130                 135                 140

Pro Ser Gly Lys Cys Pro Val Phe Gly Lys Gly Ile Ile Ile Glu Asn
145                 150                 155                 160

Ser Asn Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
            195                 200                 205

Lys Asn Leu Asp Glu Leu Thr Leu Cys Ser Arg His Ala Gly Asn Met
        210                 215                 220

Ile Pro Asp Asn Asp Lys Asn Ser Asn Tyr Lys Tyr Pro Ala Val Tyr
225                 230                 235                 240

Asp Asp Lys Asp Lys Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Asn Tyr Thr
            275                 280                 285

Tyr Leu Ser Lys Asn Val Val Asp Asn Trp Glu Lys Val Cys Pro Arg
        290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys

```
                355                 360                 365
Asn Lys Asn Ala Ser Met Ile Lys Ser Ala Phe Leu Pro Thr Gly Ala
    370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415

Thr Cys Leu Ile Asn Asn Ser Ser Tyr Ile Ala Thr Thr Ala Leu Ser
            420                 425                 430

His Pro Ile Glu Val Glu Asn Asn Phe Pro Cys Ser Leu Tyr Lys Asp
        435                 440                 445

Glu Ile Met Lys Glu Ile Glu Arg Glu Ser Lys Arg Ile Lys Leu Asn
    450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495

Val Ser Asn Ser Thr Cys Arg Phe Phe Val Cys Lys Cys Val Glu Arg
            500                 505                 510

Arg Ala Glu Val Thr Ser Asn Asn Glu Val Val Lys Glu Glu Tyr
        515                 520                 525

Lys Asp Glu Tyr Ala Asp Ile Pro Glu His Lys Pro Thr Tyr Asp Lys
    530                 535                 540

Met Lys Ile Ile Ile Ala Ser Ser Ala Ala Val Ala Val Leu Ala Thr
545                 550                 555                 560

Ile Leu Met Val Tyr Leu Tyr Lys
                565

<210> SEQ ID NO 67
<211> LENGTH: 454
<212> TYPE: PRT
<213> ORGANISM: Artificial Sequence
<220> FEATURE:
<223> OTHER INFORMATION: chimeric protein

<400> SEQUENCE: 67

Glu Gly Pro Asn Asn Val Ile Ser Glu Asn Gly His Ile Asn Tyr Asp
1               5                   10                  15

Met Ile Gln Lys Glu Asn Thr Glu Arg Ser Thr Lys Leu Ile Asn Pro
                20                  25                  30

Trp Glu Lys Tyr Met Glu Lys Tyr Asp Ile Glu Lys Met His Gly Ser
            35                  40                  45

Gly Ile Arg Val Asp Leu Gly Glu Asp Ala Arg Val Glu Asn Arg Asp
        50                  55                  60

Tyr Arg Ile Pro Ser Gly Lys Cys Pro Val Phe Gly Lys Gly Ile Thr
65                  70                  75                  80

Ile Gln Asn Ser Asn Thr Thr Phe Leu Thr Pro Val Ala Thr Gly Asn
                85                  90                  95

Gln Tyr Val Lys Asp Gly Gly Leu Ala Leu Pro Pro Thr Glu Pro Leu
            100                 105                 110

Leu Ser Pro Met Thr Leu Asp Glu Leu Arg His Phe Tyr Lys Asp Asn
        115                 120                 125

Lys Tyr Ile Lys Asn Leu Asp Glu Leu Ser Leu Cys Ala Lys His Thr
    130                 135                 140

Ser Phe Tyr Val Pro Gly Asn Asn Ala Asn Ser Ala Tyr Arg His Pro
```

```
                145                 150                 155                 160
Ala Val Tyr Asp Asp Lys Asp Lys Cys His Met Leu Tyr Val Ala
                165                 170                 175

Ala Gln Glu Asn Met Gly Pro Arg Tyr Cys Ser Asn Asn Glu Ser Lys
                180                 185                 190

Arg Asn Gln Pro Phe Cys Phe Thr Pro Glu Lys Ile Ile Ser Phe Gln
                195                 200                 205

Asn Tyr Thr Tyr Leu Thr Lys Asn Leu Arg Asp Asp Trp Glu Thr Ser
210                 215                 220

Cys Pro Arg Lys Asn Ile Gln Asn Ala Lys Phe Gly Ile Trp Val Asp
225                 230                 235                 240

Gly Tyr Cys Lys Asp Tyr Gln Lys His Thr Val His Asp Ser Ile Asp
                245                 250                 255

Leu Phe Lys Cys Asn Gln Ile Ile Phe Asn Glu Ser Ala Ser Asp Gln
                260                 265                 270

Pro Lys Gln Tyr Glu Lys His Leu Glu Asp Thr Thr Lys Phe Arg Gln
                275                 280                 285

Gly Val Ala Glu Arg Asn Gly Lys Leu Ile Gly Glu Ala Leu Leu Pro
                290                 295                 300

Ile Gly Ser Tyr Lys Ser Asp Gln Ile Lys Ser His Gly Arg Gly Tyr
305                 310                 315                 320

Asn Trp Gly Asn Tyr Asp Thr Glu Asn Gln Lys Cys Tyr Ile Phe Glu
                325                 330                 335

Thr Lys Pro Thr Cys Leu Ile Asn Asp Ser Ser Phe Ile Ala Thr Thr
                340                 345                 350

Ala Leu Ser His Pro Ile Glu Val Glu Asn Asn Phe Pro Cys Ser Ile
                355                 360                 365

Tyr Lys Asp Lys Ile Met Glu Glu Ile Lys Val Leu Asn Lys Asn Ile
                370                 375                 380

Ser Asn Gly Asn Asn Ser Ile Glu Phe Pro Arg Ile Phe Ile Ser Asp
385                 390                 395                 400

Asp Lys Asp Ser Leu Lys Cys Pro Cys Asp Pro Glu Met Leu Ser Asn
                405                 410                 415

Ser Thr Cys Arg Phe Phe Val Cys Asn Cys Val Glu Lys Arg Gln Tyr
                420                 425                 430

Ile Ala Glu Asn Asp Val Glu Ile Lys Glu Glu Phe Arg Ser Glu
                435                 440                 445

Tyr Glu Ser Pro Ser Asn
    450

<210> SEQ ID NO 68
<211> LENGTH: 459
<212> TYPE: PRT
<213> ORGANISM: Artificial Sequence
<220> FEATURE:
<223> OTHER INFORMATION: chimeric protein

<400> SEQUENCE: 68

Glu Gly Pro Asn Asn Val Ile Ser Glu Asn Gly His Ile Asn Tyr Asp
1               5                   10                  15

Met Ile Ser Ile Glu Ile Val Glu Arg Ser Asn Tyr Met Gly Asn Pro
                20                  25                  30

Trp Thr Glu Tyr Met Ala Lys Tyr Asp Ile Glu Glu Val His Gly Ser
            35                  40                  45

Gly Ile Arg Val Asp Leu Gly Glu Asp Ala Glu Val Ala Gly Thr Gln
```

```
                50                  55                  60
Tyr Arg Leu Pro Ser Gly Lys Cys Pro Val Ile Gly Lys Gly Ile Ile
 65                  70                  75                  80

Ile Glu Asn Ser Glu Val Ser Phe Leu Thr Pro Val Ala Thr Gly Asp
                     85                  90                  95

Gln Ser Leu Arg Ser Gly Gly Phe Ala Phe Pro Lys Thr Asp Val His
                100                 105                 110

Met Ser Pro Ile Thr Ile Asp Asn Met Lys Thr Met Tyr Lys Glu His
                115                 120                 125

Pro Glu Val Val Lys Leu Asn Asn Met Thr Leu Cys Ser Arg His Ala
130                 135                 140

Gly Asn Met Ile Pro Asp Asn Asp Lys Asn Ser Asn Tyr Lys Tyr Pro
145                 150                 155                 160

Ala Val Tyr Asp Lys Ser Asn Ser Thr Cys Tyr Ile Leu Tyr Ile Ala
                165                 170                 175

Ala Gln Glu Asn Asn Gly Pro Arg Tyr Cys Asn Lys Asp Ala Asn Asn
                180                 185                 190

Asp Asn Ser Met Phe Cys Phe Arg Pro Glu Lys Asp Glu Lys Tyr Lys
                195                 200                 205

Asn Leu Ser Tyr Leu Ser Lys Asn Val Val Asp Asn Trp Glu Lys Val
                210                 215                 220

Cys Pro Asn Lys Ser Leu Lys Asn Ala Lys Phe Gly Leu Trp Val Asp
225                 230                 235                 240

Gly Asn Cys Glu Asp Ile Pro His Val Asn Glu Phe Pro Ala Asp Ser
                245                 250                 255

Leu Leu Glu Cys Asn Lys Leu Val Phe Glu Leu Ser Ala Ser Asp Gln
                260                 265                 270

Pro Lys Gln Tyr Glu Gln His Leu Thr Asp Tyr Glu Lys Ile Lys Glu
                275                 280                 285

Gly Phe Lys Asn Lys Asn Ala Ser Met Ile Lys Ser Ala Phe Leu Pro
                290                 295                 300

Thr Gly Ala Phe Lys Ala Asp Arg Tyr Lys Ser His Gly Lys Gly Tyr
305                 310                 315                 320

Asn Trp Gly Asn Tyr Asn Ser Gln Thr Lys Lys Cys Glu Ile Phe Asn
                325                 330                 335

Val Lys Pro Thr Cys Leu Ile Asn Asn Arg Asn Tyr Ile Ala Thr Thr
                340                 345                 350

Ala Leu Ser Ser Thr Glu Glu Phe Glu Glu Gln Phe Pro Cys Asp Leu
                355                 360                 365

Tyr Lys Asn Ile Asn Lys Glu Ile Glu Arg Glu Ser Lys Arg Ile Lys
                370                 375                 380

Leu Asn Asp Asn Asp Glu Gly Asn Lys Lys Ile Ile Ala Pro Arg
385                 390                 395                 400

Ile Phe Ile Ser Thr Asp Lys Asn Ser Leu Asn Cys Pro Cys Glu Pro
                405                 410                 415

Thr Gln Val Thr Glu Ser Ser Cys Asn Phe Tyr Val Cys Lys Cys Val
                420                 425                 430

Glu Arg Arg Ala Glu Val Thr Ser Asn Asn Glu Val Val Val Lys Glu
                435                 440                 445

Glu Tyr Lys Asp Glu Tyr Ala Asp Ile Pro Glu
450                 455

<210> SEQ ID NO 69
```

```
<211> LENGTH: 454
<212> TYPE: PRT
<213> ORGANISM: Artificial Sequence
<220> FEATURE:
<223> OTHER INFORMATION: chimeric protein

<400> SEQUENCE: 69
```

Glu Gly Pro Asn Asn Val Ile Ser Glu Asn Gly His Ile Asn Tyr Asp
1               5                   10                  15

Met Ile Gln Lys Glu Asn Thr Glu Arg Ser Thr Lys Leu Ile Asn Pro
            20                  25                  30

Trp Glu Lys Tyr Met Glu Lys Tyr Asp Ile Glu Lys Met His Gly Ser
        35                  40                  45

Gly Ile Arg Val Asp Leu Gly Glu Asp Ala Glu Val Ala Gly Thr Gln
    50                  55                  60

Tyr Arg Leu Pro Ser Gly Lys Cys Pro Val Phe Gly Lys Gly Ile Ile
65                  70                  75                  80

Ile Glu Asn Ser Asn Thr Thr Phe Leu Thr Pro Val Ala Thr Gly Asn
                85                  90                  95

Gln Tyr Leu Lys Asp Gly Gly Phe Ala Phe Pro Pro Thr Glu Pro Leu
            100                 105                 110

Met Ser Pro Met Thr Leu Asp Glu Met Arg His Phe Tyr Lys Asp Asn
        115                 120                 125

Lys Tyr Val Lys Asn Leu Asp Glu Leu Thr Leu Cys Ser Arg His Ala
    130                 135                 140

Gly Asn Met Ile Pro Asp Asn Asp Lys Asn Ser Asn Tyr Lys Tyr Pro
145                 150                 155                 160

Ala Val Tyr Asp Asp Lys Asp Lys Lys Cys His Ile Leu Tyr Ile Ala
                165                 170                 175

Ala Gln Glu Asn Asn Gly Pro Arg Tyr Cys Asn Lys Asp Glu Ser Lys
            180                 185                 190

Arg Asn Ser Met Phe Cys Phe Arg Pro Ala Lys Asp Ile Ser Phe Gln
        195                 200                 205

Asn Tyr Thr Tyr Leu Ser Lys Asn Val Val Asp Asn Trp Glu Lys Val
    210                 215                 220

Cys Pro Arg Lys Ser Ile Lys Asn Ala Lys Phe Gly Ile Trp Val Asp
225                 230                 235                 240

Gly Tyr Cys Lys Asp Tyr Gln Lys His Thr Val His Asp Ser Asp Ser
                245                 250                 255

Leu Phe Glu Cys Asn Gln Ile Ile Phe Glu Glu Ser Ala Ser Asp Gln
            260                 265                 270

Pro Lys Gln Tyr Glu Gln His Leu Thr Asp Tyr Glu Lys Ile Lys Glu
        275                 280                 285

Gly Phe Lys Asn Lys Asn Ala Ser Met Ile Lys Ser Ala Phe Leu Pro
    290                 295                 300

Thr Gly Ala Phe Lys Ala Asp Arg Tyr Lys Ser His Gly Arg Gly Tyr
305                 310                 315                 320

Asn Trp Gly Asn Tyr Asp Ser Gln Asn Lys Lys Cys Tyr Ile Phe Glu
                325                 330                 335

Thr Lys Pro Thr Cys Leu Ile Asn Asp Arg Asn Phe Ile Ala Thr Thr
            340                 345                 350

Ala Leu Ser His Thr Ile Glu Phe Glu Glu Gln Phe Pro Cys Asp Ile
        355                 360                 365

Tyr Lys Asn Lys Ile Asn Glu Glu Ile Lys Val Leu Asn Lys Asn Ile
    370                 375                 380

-continued

```
Ser Asn Gly Asn Asn Ser Ile Glu Phe Pro Arg Ile Phe Ile Ser Thr
385                 390                 395                 400

Asp Lys Asn Ser Leu Asn Cys Pro Cys Glu Pro Thr Gln Leu Thr Glu
                405                 410                 415

Ser Ser Cys Asn Phe Tyr Val Cys Asn Cys Val Glu Lys Arg Gln Tyr
            420                 425                 430

Ile Ala Glu Asn Asn Asp Val Glu Ile Lys Glu Glu Phe Arg Ser Glu
        435                 440                 445

Tyr Glu Ser Pro Ser Asn
        450

<210> SEQ ID NO 70
<211> LENGTH: 454
<212> TYPE: PRT
<213> ORGANISM: Artificial Sequence
<220> FEATURE:
<223> OTHER INFORMATION: chimeric protein

<400> SEQUENCE: 70

Glu Gly Pro Asn Asn Val Ile Ser Glu Asn Gly His Ile Asn Tyr Asp
1               5                   10                  15

Met Ile Gln Lys Glu Asn Thr Glu Arg Ser Thr Lys Leu Ile Asn Pro
            20                  25                  30

Trp Thr Glu Tyr Met Ala Lys Tyr Asp Ile Glu Val His Gly Ser
        35                  40                  45

Gly Ile Arg Val Asp Leu Gly Glu Asp Ala Arg Val Glu Asn Arg Asp
    50                  55                  60

Tyr Arg Ile Pro Ser Gly Lys Cys Pro Val Phe Gly Lys Gly Ile Thr
65                  70                  75                  80

Ile Gln Asn Ser Glu Val Ser Phe Leu Thr Pro Val Ala Thr Gly Asp
                85                  90                  95

Gln Ser Val Arg Ser Gly Gly Leu Ala Leu Pro Lys Thr Asp Val His
            100                 105                 110

Leu Ser Pro Ile Thr Ile Asp Asn Leu Lys Thr Met Tyr Lys Glu His
        115                 120                 125

Pro Glu Ile Val Lys Leu Asn Glu Leu Ser Leu Cys Ala Lys His Thr
    130                 135                 140

Ser Phe Tyr Val Pro Gly Asn Asn Ala Asn Ser Ala Tyr Arg His Pro
145                 150                 155                 160

Ala Val Tyr Asp Asp Ser Asn Lys Thr Cys Tyr Met Leu Tyr Val Ala
                165                 170                 175

Ala Gln Glu Asn Met Gly Pro Arg Tyr Cys Ser Asn Asn Ala Asn Asn
            180                 185                 190

Asp Asn Gln Pro Phe Cys Phe Arg Pro Ala Lys Asp Ile Lys Tyr Gln
        195                 200                 205

Asn Leu Thr Tyr Leu Thr Lys Asn Leu Val Asp Asn Trp Glu Lys Val
    210                 215                 220

Cys Pro Arg Lys Asn Leu Gln Asn Ala Lys Phe Gly Leu Trp Val Asp
225                 230                 235                 240

Gly Tyr Cys Lys Asp Ile Pro His Val Asn Glu Phe Pro Ala Ile Asp
                245                 250                 255

Leu Phe Glu Cys Asn Lys Leu Val Phe Glu Leu Ser Ala Ser Asp Gln
            260                 265                 270

Pro Lys Gln Tyr Glu Lys His Leu Glu Asp Thr Thr Lys Phe Arg Gln
        275                 280                 285
```

```
Gly Val Ala Glu Arg Asn Gly Lys Leu Ile Gly Glu Ala Leu Leu Pro
            290                 295                 300
Ile Gly Ser Tyr Lys Ser Asp Gln Ile Lys Ser His Gly Lys Gly Tyr
305                 310                 315                 320
Asn Trp Gly Asn Tyr Asn Thr Glu Thr Gln Lys Cys Glu Ile Phe Asn
                325                 330                 335
Val Lys Pro Thr Cys Leu Ile Asn Asn Ser Ser Tyr Ile Ala Thr Thr
            340                 345                 350
Ala Leu Ser His Pro Ile Glu Val Glu Asn Asn Phe Pro Cys Asp Ile
            355                 360                 365
Tyr Lys Asn Lys Ile Asn Glu Ile Lys Val Leu Asn Lys Asn Ile
            370                 375                 380
Ser Asn Gly Asn Asn Ser Ile Glu Phe Pro Arg Ile Phe Ile Ser Thr
385                 390                 395                 400
Asp Lys Asn Ser Leu Asn Cys Pro Cys Glu Pro Thr Gln Leu Thr Asn
                405                 410                 415
Ser Thr Cys Asn Phe Tyr Val Cys Asn Cys Val Glu Lys Arg Gln Tyr
                420                 425                 430
Val Ala Glu Asn Asn Asp Val Gly Ile Lys Glu Glu Phe Arg Ser Glu
            435                 440                 445
Tyr Glu Ser Pro Ser Asn
    450

<210> SEQ ID NO 71
<211> LENGTH: 460
<212> TYPE: PRT
<213> ORGANISM: Artificial Sequence
<220> FEATURE:
<223> OTHER INFORMATION: chimeric protein

<400> SEQUENCE: 71

Glu Gly Pro Asn Asn Val Ile Ser Glu Asn Gly His Ile Asn Tyr Asp
1               5                   10                  15
Met Ile Ser Ile Glu Ile Val Glu Arg Ser Asn Tyr Met Gly Asn Pro
            20                  25                  30
Trp Thr Glu Tyr Met Ala Lys Tyr Asp Ile Glu Lys Met His Gly Ser
        35                  40                  45
Gly Ile Arg Val Asp Leu Gly Asp Ala Arg Val Glu Asn Arg Asp
    50                  55                  60
Tyr Arg Ile Pro Ser Gly Lys Cys Pro Val Ile Gly Lys Gly Ile Thr
65                  70                  75                  80
Ile Gln Asn Ser Glu Val Ser Phe Leu Thr Pro Val Ala Thr Gly Asp
                85                  90                  95
Gln Ser Val Arg Ser Gly Gly Leu Ala Leu Pro Lys Thr Asp Val His
            100                 105                 110
Leu Ser Pro Ile Thr Ile Asp Asn Leu Lys Thr Met Tyr Lys Glu His
            115                 120                 125
Pro Glu Ile Val Lys Leu Asn Asn Met Ser Leu Cys Ala Lys His Thr
        130                 135                 140
Ser Phe Tyr Val Pro Gly Asn Asn Ala Asn Ser Ala Tyr Arg His Pro
145                 150                 155                 160
Ala Val Tyr Asp Lys Ser Asn Ser Thr Cys Tyr Met Leu Tyr Val Ala
                165                 170                 175
Ala Gln Glu Asn Met Gly Pro Arg Tyr Cys Ser Asn Asn Ala Asn Asn
            180                 185                 190
```

```
Asp Asn Gln Pro Phe Cys Phe Thr Pro Glu Lys Ile Glu Lys Tyr Lys
            195                 200                 205

Asn Leu Ser Tyr Leu Thr Lys Asn Leu Arg Asp Asp Trp Glu Thr Ser
    210                 215                 220

Cys Pro Asn Lys Ser Ile Gln Asn Ala Lys Phe Gly Leu Trp Val Asp
225                 230                 235                 240

Gly Asn Cys Glu Asp Ile Pro His His Thr Val His Asp Ser Asp Ser
                245                 250                 255

Leu Leu Lys Cys Asn Gln Ile Ile Phe Asn Glu Ser Ala Ser Asp Gln
            260                 265                 270

Pro Lys Gln Tyr Glu Lys His Leu Glu Asp Thr Thr Lys Phe Arg Gln
        275                 280                 285

Gly Val Ala Glu Arg Asn Gly Lys Leu Ile Gly Glu Ala Leu Leu Pro
    290                 295                 300

Ile Gly Ser Tyr Lys Ser Asp Gln Ile Lys Ser His Gly Arg Gly Tyr
305                 310                 315                 320

Asn Trp Gly Asn Tyr Asp Ser Glu Asn Lys Lys Cys Tyr Ile Phe Glu
                325                 330                 335

Thr Lys Pro Thr Cys Leu Ile Asn Asn Ser Ser Phe Ile Ala Thr Thr
            340                 345                 350

Ala Leu Ser Ser Thr Glu Glu Phe Glu Asn Asn Phe Pro Cys Ser Leu
        355                 360                 365

Tyr Lys Asp Glu Ile Met Lys Glu Ile Glu Arg Glu Ser Lys Arg Ile
    370                 375                 380

Lys Leu Asn Asp Asn Asp Glu Gly Asn Lys Lys Ile Ile Ala Pro
385                 390                 395                 400

Arg Ile Phe Ile Ser Asp Asp Lys Asp Ser Leu Lys Cys Pro Cys Asp
                405                 410                 415

Pro Glu Met Val Ser Asn Ser Thr Cys Arg Phe Phe Val Cys Lys Cys
            420                 425                 430

Val Glu Arg Arg Ala Glu Val Thr Ser Asn Asn Glu Val Val Val Lys
        435                 440                 445

Glu Glu Tyr Lys Asp Glu Tyr Ala Asp Ile Pro Glu
    450                 455                 460

<210> SEQ ID NO 72
<211> LENGTH: 454
<212> TYPE: PRT
<213> ORGANISM: Artificial Sequence
<220> FEATURE:
<223> OTHER INFORMATION: chimeric protein

<400> SEQUENCE: 72

Glu Gly Pro Asn Asn Val Ile Ser Glu Asn Gly His Ile Asn Tyr Asp
1               5                   10                  15

Met Ile Gln Lys Glu Asn Thr Glu Arg Ser Thr Lys Leu Ile Asn Pro
            20                  25                  30

Trp Glu Lys Tyr Met Glu Lys Tyr Asp Ile Glu Lys Met His Gly Ser
        35                  40                  45

Gly Ile Arg Val Asp Leu Gly Asp Ala Glu Val Ala Gly Thr Gln
    50                  55                  60

Tyr Arg Leu Pro Ser Gly Lys Cys Pro Val Phe Gly Lys Gly Ile Ile
65                  70                  75                  80

Ile Glu Asn Ser Asn Thr Thr Phe Leu Thr Pro Val Ala Thr Gly Asn
                85                  90                  95
```

```
Gln Tyr Leu Lys Asp Gly Gly Phe Ala Phe Pro Pro Thr Glu Pro Leu
                100                 105                 110

Met Ser Pro Met Thr Leu Asp Glu Met Arg His Phe Tyr Lys Asp Asn
            115                 120                 125

Lys Tyr Val Lys Asn Leu Asp Asn Met Thr Leu Cys Ser Arg His Ala
        130                 135                 140

Gly Asn Met Ile Pro Asp Asn Asp Lys Asn Ser Asn Tyr Lys Tyr Pro
145                 150                 155                 160

Ala Val Tyr Asp Lys Ser Asn Ser Lys Cys His Ile Leu Tyr Ile Ala
                165                 170                 175

Ala Gln Glu Asn Asn Gly Pro Arg Tyr Cys Asn Lys Asp Ser Lys
            180                 185                 190

Arg Asn Ser Met Phe Cys Phe Arg Pro Glu Lys Ile Glu Lys Tyr Lys
        195                 200                 205

Asn Leu Ser Tyr Leu Ser Lys Asn Val Arg Asp Asp Trp Glu Thr Ser
    210                 215                 220

Cys Pro Asn Lys Ser Ile Lys Asn Ala Lys Phe Gly Ile Trp Val Asp
225                 230                 235                 240

Gly Tyr Cys Lys Asp Tyr Gln Lys His Thr Val His Asp Ser Asp Ser
                245                 250                 255

Leu Leu Lys Cys Asn Gln Ile Ile Phe Asn Glu Ser Ala Ser Asp Gln
            260                 265                 270

Pro Lys Gln Tyr Glu Gln His Leu Thr Asp Tyr Glu Lys Ile Lys Glu
        275                 280                 285

Gly Phe Lys Asn Lys Asn Ala Ser Met Ile Lys Ser Ala Phe Leu Pro
    290                 295                 300

Thr Gly Ala Phe Lys Ala Asp Arg Tyr Lys Ser His Gly Arg Gly Tyr
305                 310                 315                 320

Asn Trp Gly Asn Tyr Asp Ser Gln Asn Lys Lys Cys Tyr Ile Phe Glu
                325                 330                 335

Thr Lys Pro Thr Cys Leu Ile Asn Asp Arg Asn Phe Ile Ala Thr Thr
            340                 345                 350

Ala Leu Ser Ser Thr Glu Glu Phe Glu Glu Gln Phe Pro Cys Asp Ile
        355                 360                 365

Tyr Lys Asn Lys Ile Asn Glu Glu Ile Lys Val Leu Asn Lys Asn Ile
    370                 375                 380

Ser Asn Gly Asn Asn Ser Ile Glu Phe Pro Arg Ile Phe Ile Ser Thr
385                 390                 395                 400

Asp Lys Asn Ser Leu Asn Cys Pro Cys Glu Pro Thr Gln Leu Thr Glu
                405                 410                 415

Ser Ser Cys Asn Phe Tyr Val Cys Asn Cys Val Glu Lys Arg Gln Tyr
            420                 425                 430

Ile Ala Glu Asn Asn Asp Val Glu Ile Lys Glu Glu Phe Arg Ser Glu
        435                 440                 445

Tyr Glu Ser Pro Ser Asn
    450

<210> SEQ ID NO 73
<211> LENGTH: 454
<212> TYPE: PRT
<213> ORGANISM: Artificial Sequence
<220> FEATURE:
<223> OTHER INFORMATION: chimeric protein

<400> SEQUENCE: 73
```

```
Glu Gly Pro Asn Asn Val Ile Ser Glu Asn Gly His Ile Asn Tyr Asp
1               5                   10                  15

Met Ile Gln Lys Glu Asn Thr Glu Arg Ser Thr Lys Met Ile Asn Pro
            20                  25                  30

Trp Glu Lys Tyr Met Glu Lys Tyr Asp Ile Glu Lys Met His Gly Ser
        35                  40                  45

Gly Ile Arg Val Asp Leu Gly Glu Asp Ala Arg Val Glu Asn Arg Asp
    50                  55                  60

Tyr Arg Ile Pro Ser Gly Lys Cys Pro Val Ile Gly Lys Gly Ile Thr
65                  70                  75                  80

Ile Gln Asn Ser Glu Val Ser Phe Leu Thr Pro Val Ala Thr Gly Asp
                85                  90                  95

Gln Ser Val Arg Ser Gly Gly Leu Ala Leu Pro Lys Thr Asp Val His
                100                 105                 110

Leu Ser Pro Ile Thr Ile Asp Asn Leu Lys Thr Met Tyr Lys Glu His
            115                 120                 125

Pro Glu Ile Val Lys Leu Asn Asn Met Ser Leu Cys Ala Lys His Thr
    130                 135                 140

Ser Phe Tyr Val Pro Gly Asn Asn Ala Asn Ser Ala Tyr Arg His Pro
145                 150                 155                 160

Ala Val Tyr Asp Lys Ser Asn Ser Thr Cys Tyr Met Leu Tyr Val Ala
                165                 170                 175

Ala Gln Glu Asn Met Gly Pro Arg Tyr Cys Ser Asn Asn Ala Asn Asn
                180                 185                 190

Asp Asn Gln Pro Phe Cys Phe Thr Pro Glu Lys Ile Glu Lys Tyr Lys
            195                 200                 205

Asn Leu Ser Tyr Leu Thr Lys Asn Leu Arg Asp Asp Trp Glu Thr Ser
    210                 215                 220

Cys Pro Asn Lys Ser Ile Lys Asn Ala Lys Phe Gly Leu Trp Val Asp
225                 230                 235                 240

Gly Asn Cys Glu Asp Ile Pro His Val Asn Val His Asp Ser Asp Ser
                245                 250                 255

Leu Leu Lys Cys Asn Gln Ile Ile Phe Asn Glu Ser Ala Ser Asp Gln
                260                 265                 270

Pro Lys Gln Tyr Glu Lys His Leu Glu Asp Thr Thr Lys Phe Arg Gln
            275                 280                 285

Gly Val Ala Glu Arg Asn Gly Lys Leu Ile Gly Glu Ala Leu Leu Pro
    290                 295                 300

Ile Gly Ser Tyr Lys Ser Asp Gln Ile Lys Ser His Gly Arg Gly Tyr
305                 310                 315                 320

Asn Trp Gly Asn Tyr Asp Ser Gln Asn Lys Lys Cys Glu Ile Phe Asn
                325                 330                 335

Val Lys Pro Thr Cys Leu Ile Asn Asp Arg Asn Phe Ile Ala Thr Thr
                340                 345                 350

Ala Leu Ser Ser Thr Glu Glu Phe Glu Glu Gln Phe Pro Cys Asp Ile
            355                 360                 365

Tyr Lys Asn Lys Ile Asn Glu Glu Ile Lys Val Leu Asn Lys Asn Ile
    370                 375                 380

Ser Asn Gly Asn Asn Ser Ile Glu Phe Pro Arg Ile Phe Ile Ser Thr
385                 390                 395                 400

Asp Lys Asn Ser Leu Asn Cys Pro Cys Glu Pro Thr Gln Leu Thr Glu
                405                 410                 415
```

-continued

```
Ser Ser Cys Asn Phe Tyr Val Cys Asn Cys Val Glu Arg Arg Ala Glu
            420                 425                 430

Val Thr Ser Asn Asn Glu Val Val Val Lys Glu Glu Phe Lys Ser Glu
        435                 440                 445

Tyr Glu Ser Pro Ser Asn
    450
```

AMA-1 EPITOPES, ANTIBODIES, COMPOSITIONS, AND METHODS OF MAKING AND USING THE SAME

CROSS-REFERENCE TO RELATED APPLICATIONS

This application is a U.S. National Stage application filed under 35 U.S.C. § 371 of International Patent Application number PCT/US2014/064972, filed Nov. 11, 2014, which claims priority to U.S. Provisional Applications Nos. 61/902,521 filed on Nov. 11, 2013 and 61/921,031 filed on Dec. 26, 2013 entitled "AMA-1 EPITOPES, ANTIBODIES, COMPOSITIONS, AND METHODS OF MAKING AND USING THE SAME." The contents of each of the preceding applications are hereby incorporated herein by reference in their entireties.

RIGHTS IN THE INVENTION

The invention was made with support from the United States Government and, specifically, the Walter Reed Army Institute of Research. Accordingly, the United States government has certain rights in the invention.

SEQUENCE LISTING

The application includes a sequence listing file which is submitted in computer readable form only "27533US03_ST25_RV" created on Mar. 8, 2018 and which is 120,118 bytes in size. In lieu of a hardcopy, the electronic version of the sequence listing is incorporated into the application by reference.

TECHNICAL FIELD

The disclosure generally relates to compositions, including vaccines, that contain immunogenic peptide or epitopes that provide protection against a broad range of malarial strains, as well as to antibodies directed to the epitopes, methods of treating malaria in a subject, and methods of inducing a broad-based immune response against multiple strains of malaria in a subject.

BACKGROUND

According to recent World Health Organization estimates, over 200 million annual cases of malaria are reported worldwide, resulting in over 600,000 deaths (World Health Organization, 2012 World Malaria Report for the year 2010). Malaria is caused by mosquito-borne parasites, usually of the *Plasmodium* genus. At least four species of malaria parasites can infect humans under natural conditions: *Plasmodium falciparum, Plasmodium vivax, Plasmodium ovale* and *Plasmodium malariae*. The species *P. falciparum* and *P. vivax* are responsible for the majority of worldwide infections. In nature, malaria parasites spread by infecting successively two types of hosts, humans and female *Anopheles* mosquitoes. In humans, the cycle begins with a bite from a mosquito harboring a malaria parasite. The bite can inject hundreds of sporozoites under the human skin during a blood meal. These sporozoites travel from the site of the bite to the liver. They multiply in liver cells as well as in red blood cells. In the blood, successive broods of parasites grow inside the red blood cells and destroy them, releasing daughter parasites (merozoites) that continue the cycle by invading other red blood cells. The blood stage parasites cause the symptoms of malaria. When certain forms of blood stage parasites ('gametocytes") are picked up by a female *Anopheles* mosquito during a blood meal, they start another, different cycle of growth and multiplication in the mosquito. After 10-18 days, the parasites are found (as "sporozoites") in the mosquito's salivary glands. When the mosquito takes a blood meal on another human, the infection cycle is repeated [D. Wyler, "*Plasmodium* and *Babesia*", Chapter 287, p. 2407, in Gorbach, Bartlett & Blacklow, "Infectious Diseases, 2.sup.nd Edition, Sunders Press, 1992].

Efforts have been made to develop effective controls against the mosquito vector through the use of pesticides, but these have led to the development of pesticide-resistant mosquitoes. Similarly, the use of antiparasitic drugs (e.g., to control the *Plasmodium* microbe) has led to drug-resistance parasites. As the pesticidal and parasiticidal approaches have failed, focus has moved to vaccine development as an alternative. However, the complex parasitic life cycle has confounded efforts to develop efficacious vaccines, and consequently the FDA has not approved any malaria vaccine.

Apical Membrane Antigen-1 (AMA-1) is a protein that has an essential role in malaria merozoite invasion in host red blood cells. Initial vaccines containing AMA-1 from a single strain showed some protection; however, this protection was only observed against a strain that was homologous to the vaccine strain. The lack of protection against non-vaccine (divergent) strains, has made it difficult to produce a globally effective AMA-1 vaccine, given that hundreds if not thousands of strains are found in nature. Typically, vaccines against pathogens that exhibit antigenic diversity need to include multiple components directed to the different pathogenic strains. However, the extreme diversity in AMA-1 (with over 200 prevailing haplotypes) has precluded its successful implementation in a multivalent vaccine strategy. [See Takala S. L., et al., (2009) Extreme Polymorphism in a Vaccine antigen and risk of clinical malaria: Implications for vaccine development. *Science Translational Med* 1: 10; Polley S. D., and Conway D. J., (2001) Strong diversifying selection on domains of the *Plasmodium falciparum* apical membrane antigen 1 gene. *Genetics* 158: 1505-1512.]. Prior attempts to generate monovalent or divalent vaccines have resulted in no protection against diverse strains circulating in the field (Ref: Thera and Dicko). Accordingly, there is a need for a vaccine that protects against multiple strains of the malaria parasite and provides strain-transcending immunity against the rapidly growing blood stage of the parasite. Such vaccines can reduce global mortality and morbidity associated with malaria in humans.

SUMMARY

In some aspects the disclosure relates to methods of treating malaria in a subject in need of treatment comprising administering to the subject an effective amount of a composition comprising from about 5 to about 11 contiguous amino acids of SEQ ID NO: 1 (1e loop); from about 5 to about 30 contiguous amino acids of SEQ ID NO: 2 (polymorphic face of domain III); and a pharmaceutically acceptable carrier, vehicle, or adjuvant.

In other aspects, the disclosure related to methods of inducing an immune response in a subject suffering from malaria by administering an effective amount of a composition comprising: an immunogenic peptide comprising about 5 to about 11 contiguous amino acids of SEQ ID NO: 1; an immunogenic peptide comprising of about 5 to about 30 contiguous amino acids of SEQ ID NO: 2, and a pharmaceutically acceptable carrier, vehicle, or adjuvant.

In other aspects, the disclosure provides an isolated antibody that specifically binds to the 1e-loop region of Apical Membrane Antigen-1 (AMA-1) and recognizes an epitope of about 5 to about 11 amino acids of SEQ ID NO: 1. In some aspects, the isolated antibody specifically binds to an epitope consisting of SEQ ID NO: 1. In other aspects, the antibody inhibits the binding of AMA-1 to RON2. In some aspects, the disclosure provides the hybridoma cell lines that produce the antibody.

In yet another aspect, the disclosure provides an isolated antibody that specifically binds to the polymorphic face of domain III of AMA-1 and recognizes an epitope of about 5 to about 17 amino acids of SEQ ID NO:2. In some aspects, the isolated antibody specifically binds to an epitope consisting of 8-17, alternatively 8-11 amino acids of SEQ ID NO:2. In other aspects, the antibody inhibits the proteolytic processing of AMA-1 within a cell infected with *P. falciparum*. In yet another aspect, the present disclosure provides a composition comprising at least one antibody that specifically binds to an epitope of AMA-1 within the amino acid sequence of SEQ ID NO:2, and at least one antibody that specifically binds to an epitope of AMA-1 within the amino acid sequence of SEQ ID NO:1.

In other aspects, the disclosure provides a vaccine composition comprising at least four alleles of AMA-1, wherein the four alleles are contained within at least one chimeric protein, for example, at least two chimeric proteins.

In other aspects, the disclosure provides methods of inducing a targeted immune response in a patient exposed to *P. falciparum* infection comprising administering to the patient a vaccine composition comprising at least four alleles of AMA-1 protein, wherein the immune response is shifted towards two epitopes of AMA-1, wherein one epitope is within the amino acid sequence of SEQ ID NO:1, and one epitope is within the amino acid sequence of SEQ ID NO:2, and wherein the targeted immune response provides for broad inhibition of *P. falciparum* infection.

In other aspects, the present disclosure provides methods of eliciting an immune response in a subject exposed to or suffering from malaria comprising administering an immunogenic peptide or vaccine composition described herein.

In yet other aspects, a method of purifying AMA-1 proteins of multiple strains by a single process is provided.

In yet a further aspect, a method of treating malaria in a subject in need of treatment, comprising administering to the subject an immunogenic composition in an amount effective to induce an immune response against SEQ ID NO:1 and SEQ ID NO:2 is provided.

In yet a further aspect, a method of treating a refractory form of malaria in a subject who is undergoing or has undergone treatment, comprising administering to the subject an immunogenic composition in an amount effective to induce an immune response against SEQ ID NO:1 and SEQ ID NO:2 is provided.

In some aspects, an immunogenic peptide comprising about 5 to about 11 contiguous amino acids of SEQ ID NO: 1 is provided. In other aspects, an immunogenic peptide comprising about 5 to about 30 contiguous amino acids of SEQ ID NO:2 is provided.

In some aspects, an epitope comprising about 8 to about 11 contiguous amino acids of SEQ ID NO: 1 is provided. In other aspects, an epitope comprising about 8 to about 17 or about 8 to 11 contiguous amino acids of SEQ ID NO:2 is provided.

In yet another aspect, polynucleotide encoding the amino acid sequence of any one of the immunogenic peptides or epitopes described herein is provided.

In some aspects, an antibody the specifically binds the epitope or immunogenic peptide described herein is provided. In yet other aspects, a monoclonal antibody that binds to the epitope or immunogenic peptide is provided.

In yet another aspect, a method of treating malaria in a subject in need of treatment comprising administering to the subject an effective amount of the vaccine composition, immunogenic peptide or antibody is provided.

In another aspect, a method of treating malaria in a subject in need of treatment comprising administering to the subject an effective amount of an immunogenic peptide is provided.

In another aspect, a method of inducing an immune response in a subject suffering from malaria comprising administering to the subject an effective amount of the vaccine composition or immunogenic peptide is provided.

In yet another aspect, a method of treating malaria comprising administering an effective amount of one or more of the antibodies described herein is provided.

In some aspects, the an isolated antibody that specifically binds to the 1e-loop region of Apical Membrane Antigen-1 (AMA-1) and recognizes an epitope of about 5 to about 11 amino acids of SEQ ID NO: 1 is provided wherein the antibody comprises complementary determining regions (CDRs) 1, 2 and 3 of the heavy chain variable region and the light chain variable region, wherein the CDR1, CDR2, and CDR3 sequences of the heavy chain variable region comprise: SEQ ID NO. 27 (CDR1), SEQ ID NO 28 (CDR2) and SEQ ID NO 29 (CDR3); SEQ ID NO. 37 (CDR1), SEQ ID NO. 38 (CDR2) and SEQ ID NO: 39 (CDR3); and SEQ ID NO. 47 (CDR1), SEQ ID NO. 48 (CDR2) and SEQ ID NO. 49 (CDR3); and wherein the CDR1, CDR2, and CDR3 sequences of the light chain variable region comprise: SEQ ID NO. 32 (CDR1), SEQ ID NO 33 (CDR2) and SEQ ID NO 34 (CDR3); SEQ ID NO. 42 (CDR1), SEQ ID NO. 43 (CDR2) and SEQ ID NO: 44 (CDR3); and SEQ ID NO. 52 (CDR1), SEQ ID NO. 53 (CDR2) and SEQ ID NO. 54 (CDR3).

In some other aspects, the antibody comprises a heavy chain variable region ($V_H$) sequence and light chain variable region ($V_L$) sequence which are selected from the group consisting of SEQ ID NO: 26 ($V_H$) and SEQ ID NO: 31 ($V_L$); SEQ ID NO: 36 ($V_H$) and SEQ ID NO: 41 ($V_L$); and SEQ ID NO: 46 ($V_H$) and SEQ ID NO: 51 ($V_L$).

In yet a further aspect, an isolated antibody that specifically binds to domain III of AMA-1 and recognizes an epitope of about 5 to about 17 amino acids of SEQ ID NO:2. wherein the antibody comprises complementary determining regions (CDRs) 1, 2 and 3 of the heavy chain variable region and the light chain variable region, and wherein the CDR1, CDR2, and CDR3 sequences of the heavy chain variable region comprise: SEQ ID NO. 57 (CDR1), SEQ ID NO 58 (CDR2) and SEQ ID NO 59 (CDR3); and wherein the CDR1, CDR2, and CDR3 sequences of the light chain variable region comprise: SEQ ID NO. 62 (CDR1), SEQ ID NO 63 (CDR2) and SEQ ID NO 64 (CDR3) is provided.

In some further aspects, an antibody comprising a combination a heavy chain variable region ($V_H$) sequence set forth in SEQ ID NO: 56 and light chain variable region ($V_L$) sequence set forth in SEQ ID NO. 61 is provided.

In another aspect, a therapeutic agent or drug is provided. The therapeutic agent or drug comprises an isolated antibody, phage or peptide that bines an epitope comprising SEQ ID NO. 1, more preferably specifically binds to an epitope consisting of SEQ ID NO: 1. In yet another aspect, the therapeutic agent or drug comprises an isolated antibody, phage or peptide that specifically binds to an epitope comprising SEQ ID NO. 2, more preferably consisting of SEQ ID NO. 2.

Other aspects and embodiments will become apparent in view of the following description.

BRIEF DESCRIPTION OF THE FIGURES

The patent or application file contains at least one drawing executed in color. It is understood that copies of this patent or patent application publication with color drawing(s) will be provided by the Office upon request and payment of the necessary fee.

FIGS. 4A-4C show the following: (A) Molecular structure of chimeras used in GIA reversal assays and mapping of conformational mAb epitopes. Contiguous surface residues of P. falciparum 3D7 AMA-1 (color) were grafted onto a scaffold of rodent malaria parasite P. berghei AMA-1 (gray residues). P. falciparum AMA-1 structural elements representing three domains as defined by the crystal structure (chimeras Cry D1, Cry D2, Cry D3), the polymorphic and conserved face (chimeras POLY and CONS), residues at the rim of the hydrophobic trough (HT) and the domain-2 loop together with the neighboring 1e-loop (chimera D2+1e) were displayed. Three linear domains as defined by the disulphide bonded pattern were also displayed (chimeras Lin D1, Lin D2, Lin D3, Lin D1+2 and Lin D2+3). (B) The genes for the chimeras were expressed and proteins were purified as shown on the non-reduced coomasie blue gel. The *P. falciparum* 3D7 AMA-1 and *P. berghei* AMA-1 proteins (3D7 and PbAMA) were also run. (C) A GIA reversal assay against 3D7 strain using pooled anti-3D7 AMA-1. The reversal assay shows that while the three crystal domain chimeras CryD1, CryD2 and CryD3 by themselves show limited reversal of GIA, when added together at the same final concentration (4 μM) caused complete reversal of GIA activity of polyclonal anti-3D7 (~100% reversal). The same was true for the mixture of POLY and CONS chimeras. These data suggest that a combination of chimeras collectively displayed most of the inhibitory epitopes of 3D7 AMA-1 vaccine.

FIGS. 5A-5E show the following: (A) Binding of 3D7 AMA-1 ($OD_{450}$) to immobilized RON2 peptide inhibited by serial dilutions of the mAbs. Negative control mAb 5G8 binds to the N-terminal prosequence. (B) Western blot of a 3D7 parasite processing inhibition assay using 200 μg/ml mAbs. Top panel shows the membrane bound full-length (83 kDa) 3D7 parasite AMA-1 and the product of N-terminal processing (66 kDa). Bottom panel shows trapped co-migrating products of normal shedding (48+44 kDa) and the product of anomalous AMA-1 processing (52 kDa). (C) GIA against 3D7 target strain, using $1\times IC_{30}$ dose of individual mAbs (black, bottom group of bars), $2\times IC_{30}$ dose of individual mAbs (gray, second from bottom group of bars), $1\times IC_{30}+1\times IC_{30}$ mixture of two 1e-loop mAbs (green, third from bottom group of bars) or 1e-loop+domain2-loop mAb (blue, $4^{th}$ from bottom group of bars) or 1e-loop+domain-3 mAb (orange, second from top group of bars) or domain2 loop+domain-3 mAb (red, top bar). Mean+s.e.m. of 3 experiments; (*) $p<0.05$ comparing the mean of each group to the mean of $2\times IC_{30}$ dose of individual mAbs (gray bars). (D) GIA against the 3D7 parasite strain using increasing concentrations of mAb 1E10, with (red line) or without (blue line) the addition of $1\times IC_{30}$ concentration of mAb 4G2 (1.8 mg/ml, expected 30% GIA in green). Predicted inhibition for additive interaction (black line) was calculated according to "Bliss independence" as has been applied to determine synergy by Williams et al. [20] [21]; data are mean+s.e.m. of triplicate wells. (E) Inhibition of 7 parasite strains using 1 mg/ml of the RON2 inhibitory mAb or a 1 mg/ml mixture of the RON2 inhibitory mAbs and processing inhibitory mAb 1E10; a representative of two experiments is shown.

FIG. 12 lists the 201 isolates from which AMA-1 sequences were used to create the dendrogram in FIG. 1A. The strains highlighted in yellow were tested in invasion inhibition assays and found to be susceptible to QV antibodies. AMA-1 field isolate sequences were obtained from Genbank [33,41,78,79] and lab isolates sequences were obtained from either Genbank or the source laboratory.

Figure 13:
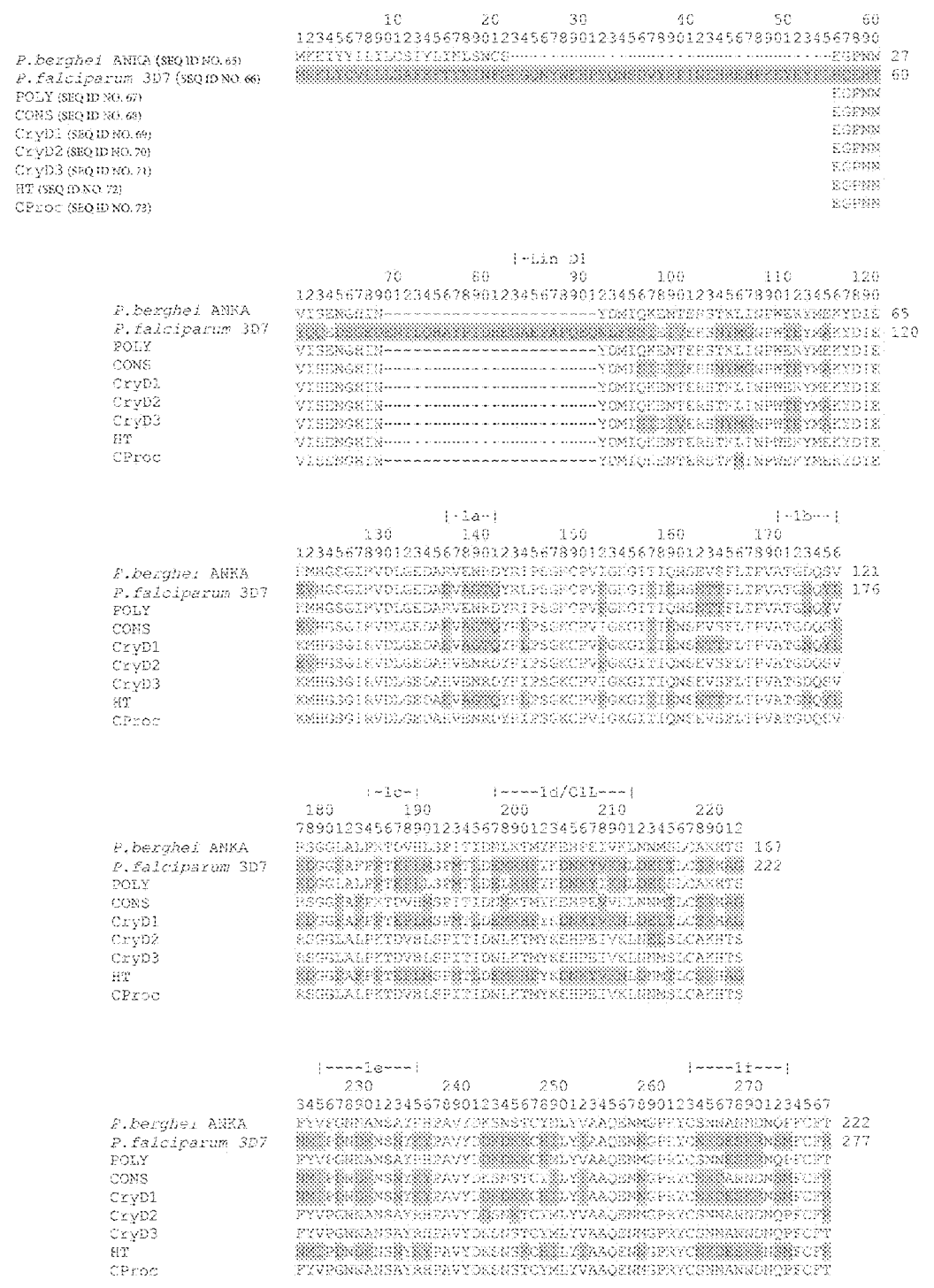
Figure 13:
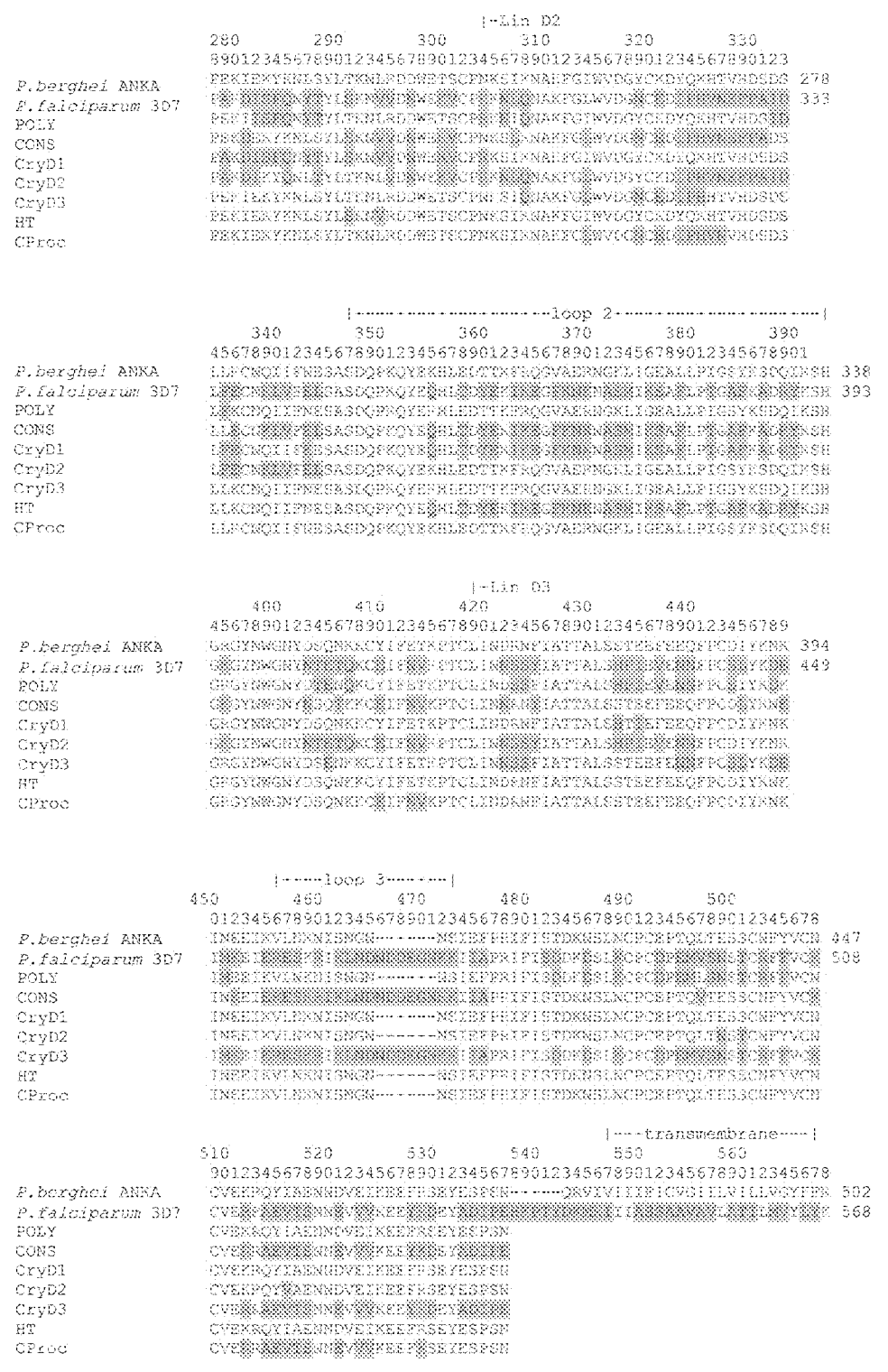

FIG. 13 shows the sequence of protein chimeras. An alignment of $P.$ $berghei$ ANKA strain AMA-1 (SEQ ID NO. 65) is shown along with the residues that were switched to $P.$ $falciparum$ 3D7 sequence (SEQ ID NO. 66) (boxed in gray). The boundaries of loops and domains are shown. The sequences include POLY (SEQ ID NO. 67); CONS (SEQ ID NO. 68); CryD1 (SEQ ID NO. 69); CryD2 (SEQ ID NO. 70); CryD3 (SEQ ID NO. 71); HT (SEQ ID NO. 72); and CProc (SEQ ID NO. 73).

DETAILED DESCRIPTION

Figure 1:
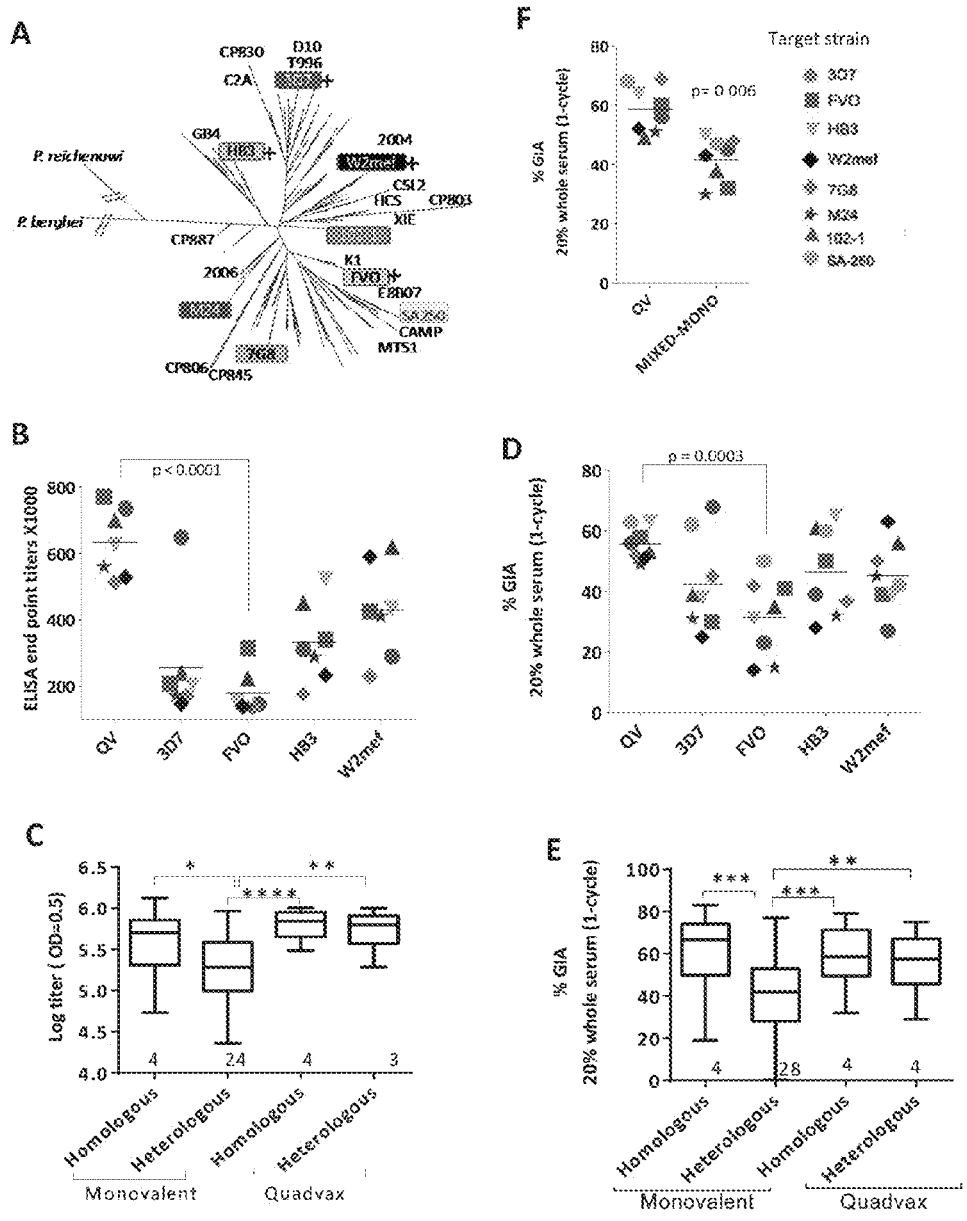
FIGS. 1A-1F show the following: (A) A dendrogram constructed with full-length AMA-1 sequences from the 26 target strains tested in GIA and 175 field strain sequences obtained from Genbank™ (FIG. 12). P. berghei (rodent) and P. reichenowi (chimpanzee) sequences were also included in the sequence analysis: (+) indicates that this allelic AMA-1 protein was included in the Quadvax (QV). Boxes indicate the 8 target strains used in the Growth Inhibition Assay (GIA) performed at WRAIR. (B) ELISA titers (×1000) for sera in the five vaccine groups (QV, 3D7, FVO, HB3 and W2mef) tested against 7 allelic proteins. Symbols are mean of three rabbits and lines are median titer across strains. (C) Box-and-whiskers plot using individual rabbit ELISA data grouped on the basis of whether the coat antigen-antisera combinations were homologous or heterologous and whether monovalent or QV rabbits were tested. The number under each box represents the total number of protein-antisera combinations included. (*) indicates, $p<0.01$, () $p<0.001$, (*) $p<0.0001$ and (****) $p<0.0001$ for ANOVA followed by Tukey's multiple comparisons test. (D) One-cycle GIA of the five vaccine groups against four non-vaccines and four vaccine strains using 1:5 whole serum dilution. Symbols in FIGS. 1B and 1D are matched, except strain SA250 that was only tested in the GIA. Each symbol is mean of three rabbits tested in two experiments and lines are median inhibition across strains. (E) GIA data from individual rabbits from three experiments grouped similar to the ELISA data, except the groups were made based on homologous and heterologous parasite-antisera combinations. (F) GIA activity of pooled QV sera was compared to a pool of the highest titer rabbit sera in the four monovalent vaccine groups 3D7+FVO+HB3+W2mef (Mixed-Mono). Lines are median inhibition across 8 target parasite strains; representative of 2 experiments is shown.

The following description provides a discussion of various aspects and embodiments of the disclosed technology. The description uses particular terms and discusses particular details that are provided for purposes of explanation and to convey a general understanding of the subject matter. One of skill in the art will appreciate that various aspects and embodiments may be practiced by incorporating modifications and equivalents to the particular details described herein. Accordingly, the particular aspects, embodiments, and terms used herein are merely descriptive of the claimed subject matter, and should not be viewed as limiting the scope of the appended claims.

In a general sense, the disclosure provides immunogenic peptides, epitopes, antibodies, vaccines, and various methods of treatment relating to Apical Membrane Antigen-1 (AMA-1) protein from $Plasmodium$ species that can infect a host and cause malaria, for example, in a human host. AMA-1 is a highly divergent and polymorphic protein that includes three domains. AMA-1 contains 16 cysteine residues that are incorporated into intramolecular disulfide bonds, which are conserved in all known sequences of AMA-1. The eight disulfide bonds fall into three non-overlapping groups that define three general subdomains within the AMA-1 ectodomain (domain 1, 2 and 3). The polymorphism sites are concentrated on one side of the protein, which has been referred to as the polymorphic face. The other side of the protein includes relatively few polymorphic sites, and has been referred to as the conserved face. At the interface of the polymorphic and conserved faces, on domain-1, there is a trough of hydrophobic residues (the hydrophobic trough, or "HT") to which rhoptry neck protein, RON2 binds. The AMA-1-RON2 protein complex localizes at the interface between the parasite and the host cell (e.g., erythrocyte) during the invasion process. [Cao J., et al., $Parasitol$ $Int$ (March 2009) 58(0:29-35].

The disclosure details an unexpected multivalent malarial vaccine that overcomes the failure and deficiencies of prior malarial vaccine strategies. The disclosure also relates to novel immunogenic peptides, epitopes, and antibodies as well as vaccines and methods of treatment that can induce very potent and broad protection against highly divergent malaria strains.

In one aspect, the disclosure relates to an isolated immunogenic peptide comprising a conserved epitope of Apical Membrane Antigen-1 (AMA-1) protein. In some embodiments of this aspect, the immunogenic peptide comprises a sequence within the ectodomain of the AMA-1 protein. In some embodiments the immunogenic peptide may comprise a sequence located in domains comprising generally conserved tertiary structure (e.g., Domain 1, Domain 2, and Domain 3) of the ectodomain. In some embodiments, Domain 1 of AMA-1 comprises amino acids 75-303 of AMA-1 (e.g., SEQ ID NO: 21). In some embodiments, Domain 2 comprises amino acid 304-418 of AMA-1 (e.g., SEQ ID NO: 20). In some embodiments, Domain 3 comprises amino acid 419-531 of AMA-1 (e.g., SEQ ID NO: 2). Non-limiting examples of alleles of AMA-1 include, for example, 3D7 (protein SEQ ID NO: 6 and nucleic acid SEQ ID NO: 24); FVO (protein SEQ ID NO: 3 and nucleic acid SEQ ID NO: 13); W2mef (protein SEQ ID NO: 5 and nucleic acid SEQ ID NO: 11) and HB3 (protein SEQ ID NO: 4 and nucleic acid SEQ ID NO: 10). Other alleles of AMA-1 known in the art may be used in connection with the compositions and methods disclosed herein including, for example, 7G8 AMA-1 (protein SEQ ID NO: 7 and nucleic acid SEQ ID NO: 8), M24 (protein SEQ ID NO: 9 and nucleic acid SEQ ID NO: 22), 102-1 AMA-1 (protein SEQ ID NO: 12 and nucleic acid SEQ ID NO:23), among others.

In embodiments the peptide comprises a sequence contained within the region identified as the 1e-loop of AMA-1. In embodiments, the 1e-loop region comprises amino acid residues 225-235 of the AMA-1 protein and is bounded by the hydrophobic trough and by a pocket that forms a contact with $Arg_{2041}$ of RON2. In some embodiments, the peptide comprises a sequence of about 5 to about 11 amino acids of SEQ ID NO: 1 (IPDNDKNSNYKY, the 1e-loop, residues 225-235 of 3D7 AMA-1 protein). In some embodiments, the peptide comprises a sequence of about 8 to about 11 amino acids of SEQ ID NO: 1. In other embodiments, the peptide comprises a sequence of about 10-11 amino acids of SEQ ID NO: 1. In some embodiments, the peptide consists of SEQ ID NO:1.

In some embodiments the isolated immunogenic peptide may comprise a sequence contained within the region identified as domain III of AMA-1. In some embodiments, the peptide comprises a sequence of about 5 to about 30 amino acids of SEQ ID NO: 2 (Domain III sequence residues 419-531). In some embodiments, the peptide comprises about 5 to about 30 amino acids of SEQ ID NO: 2. In some embodiments, the peptide comprises a sequence of about 8 to about 11 amino acids of SEQ ID NO: 2. In other embodiments, the peptide comprises a sequence of about 13 to about 17 amino acids of SEQ ID NO: 2. In some embodiments, the peptide consists of 5 to about 17, alternatively 11 to about 17 amino acids of SEQ ID NO:2.

In some embodiments an isolated immunogenic peptide may comprise a sequence contained within the region identified as domain II of AMA-1. In some embodiments, the peptide comprises a sequence of about 5 to about 30 amino acids of SEQ ID NO: 17. In some embodiments, the peptide comprises a sequence of about 5 to about 20 amino acids of SEQ ID NO: 17. In other embodiments, the peptide comprises a sequence of about 13 to about 17 amino acids of SEQ ID NO: 17. In some embodiments, the peptide comprises about 8 to about 11 amino acids of SEQ ID NO: 17

Generally, an immunogenic peptide may comprise an amino acid sequence that binds to MHC and induces a cytotoxic T lymphocyte ("CTL") response, or a B cell response (e.g. antibody production) against the antigen from which the immunogenic peptide is derived. An immunogenic peptide may contain an allele-specific motif, a consensus motif shared across alleles, or another sequence that can bind MHC. An immunogenic peptide may comprise one or more conserved residue which occurs in a significantly higher frequency than would be expected by random distribution at a particular position in a peptide. In some embodiments, a conserved residue may provide a contact point between the immunogenic peptide and the MHC structure. In particular embodiments, the immunogenic peptide comprises the amino acid sequences disclosed herein.

In non-limiting examples, an immunogenic peptide may comprise from about 5 to about 30, about 7 to about 30 or about 7 to about 20 contiguous amino acid residues of the AMA-1 protein sequence. In some embodiments, the immunogenic peptide may comprise about 8 to about 17, about 13 to about 17, or about 8 to about 11 contiguous amino acid residues of the AMA-1 sequence. In some embodiments, the immunogenic peptide may comprise 5, 6, 7, 8, 9, 10, 11, 12, 13, 14, 15, 16, 17, 18, 19, 20, 21, 22, 23, 24, 25, 26, 27, 28, 29, 30, 31, or 32 contiguous amino acid residues of the AMA-1 sequence. Suitably, the immunogenic polypeptide disclosed herein can be used to induce an immune response in a subject against AMA-1, such as a B cell response or a T cell response.

In another aspect, epitopes of AMA-1 are provided that produce broad range protection against multiple strains of malaria. An epitope, also known as antigenic determinant, is the part of an antigen that is recognized by the immune system, specifically by antibodies, B cells or T cells. In other aspects, the identification of epitopes for antibodies that compete for binding of the AMA-1 protein to the rhoptry neck protein (RON2) are provided. In other aspects, the identification of epitopes for antibodies that inhibit the proteolytic processing of AMA-1 within a cell infected with *P. falciparum* are provided.

In one aspect, the disclosure relates to a conserved epitope of Apical Membrane Antigen-1 (AMA-1) protein. In embodiments the epitope comprises a sequence contained within the region identified as the 1e-loop of AMA-1. In some embodiments, the epitope comprises a sequence of about 5 to about 11 amino acids of SEQ ID NO: 1 (IPDNDKNSNYKY, the 1e-loop, residues 225-235 of 3D7 AMA-1 protein). In some embodiments, the peptide comprises a sequence of about 8 to about 11 amino acids of SEQ ID NO: 1. In other embodiments, the peptide comprises a sequence of about 10-11 amino acids of SEQ ID NO: 1. In some embodiments, the epitope consists of SEQ ID NO:1. In other embodiments the conserved epitope of AMA-1 may comprise a sequence contained within the region identified as domain III of AMA-1. In some embodiments, the epitope comprises a sequence of about 5 to about 17 amino acids of SEQ ID NO: 2 (Domain III sequence. In some embodiments, the epitopes comprises a sequence of about 8 to about 11 amino acids of SEQ ID NO: 2. In other embodiments, the epitopes comprises a sequence of about 13 to about 17 amino acids of SEQ ID NO: 2. In some embodiments, the epitope consists of SEQ ID NO:2.

In another aspect, the disclosure relates to an isolated antibody that specifically binds to the 1e-loop region of Apical Membrane Antigen-1 (AMA-1). In some embodiments the antibody can specifically bind to a conserved epitope in the 1e-loop region of AMA-1 such as, for example, the epitopes disclosed herein. In further embodiments, the antibody can specifically bind an epitope of about 5 to about 11 amino acids of SEQ ID NO: 1 (1e-loop residues 225-235). In some embodiments, the antibody specifically binds the epitope consisting of SEQ ID NO: 1. In some embodiments, the antibody are monoclonal antibodies that specifically bind to SEQ ON NO: 1. In some embodiments, the monoclonal antibodies are mouse monoclonal antibodies. Suitable monoclonal antibodies that bind to the 1e-loop of the AMA-1 protein including monoclonal antibodies (MAb) 1B10, 4E8 and 4E11.

In some embodiments, disclosure of an antibody that bind to an epitope of Apical Membrane Antigen-1 (AMA-1) the encompass domain 3. In some embodiments, disclosure of an antibody bind to the amino acid sequence of SEQ ID NO: 2. In some embodiments, the antibody specifically binds the epitope consisting of about 5 to about 17 amino acids of SEQ ID NO: 2. In some embodiments, the present technology provides isolated monoclonal antibodies that bind to an epitope of AMA-1 within amino acid sequence SEQ ID NO: 2. In some embodiments, the monoclonal antibodies are mouse monoclonal antibodies. Suitable monoclonal antibodies that bind domain 3 of the AMA-1 protein include monoclonal antibodies (MAb) 1E10.

In some embodiments, the antibodies specifically bind AMA-1 and inhibit the formation of a protein complex comprising AMA-1 and rhoptry neck protein (RON2). Suitable antibodies include, but are not limited to monoclonal antibodies 1B10, 4E8, and 4E11.

In some embodiments, the antibodies specifically bind AMA-1 and inhibit the proteolytic processing of AMA-1 within an infected cell such as, for example, a liver cell or an erythrocyte. Suitable antibodies include, but are not limited to monoclonal antibodies Ab 2C6 and 1E10.

In some embodiments, the disclosure provides antibodies elicited by administration of the vaccine compositions described herein. For example, a vaccine composition such as QuadVax (QV) can elicit the production of anti-QV antibodies and provide broad spectrum protection against multiple strains of malaria. Anti-QV antibodies include antibodies that bind the amino acid sequence of SEQ ID NO: 1, SEQ ID NO: 2, or a combination thereof.

In another aspect the disclosure provides an isolated polynucleotide that encodes the immunogenic peptides or epitopes described herein. In another aspect the disclosure relates to an isolated polynucleotide that encodes the AMA-1 binding antibodies as disclosed herein. In further aspects the disclosure relates to vectors, expression vectors, and recombinant cells that comprise the polynucleotide. In some embodiments the polynucleotide comprises a nucleic acid sequence that encodes for amino acid sequences of SEQ ID NO: 1, SEQ ID NO: 2, or a combination thereof. In some embodiments, the nucleic acid sequence encodes a peptide comprising a sequence of about 5 to about 11 amino acids of SEQ ID NO: 1. In some embodiments, the polynucleotide contains a nucleic acid sequence that encodes a peptide comprises a sequence of about 8 to about 11 amino acids of SEQ ID NO: 1. In other embodiments, the nucleic acid sequence encodes a peptide comprises a sequence of about 10-11 amino acids of SEQ ID NO: 1. In some embodiments, the nucleic acid sequence encodes a peptide consisting of SEQ ID NO: 1. In other embodiments, the nucleic acid sequence encodes peptide comprising a sequence of about 5 to about 30 amino acids of SEQ ID NO: 2. In some embodiments, the nucleic acid sequence encodes a peptide comprising a sequence of about 8 to about 11 amino acids of SEQ ID NO: 2. In other embodiments, the nucleic acid sequence encodes a peptide comprising a sequence of about 13 to about 17 amino acids of SEQ ID NO: 2. In some embodiments, the nucleic acid sequence encodes the peptide comprising about 5 to about 20 amino acids of SEQ ID NO: 2. In some embodiments, the nucleic acid encodes the peptide consists of SEQ ID NO:2.

In some aspects, the disclosure relates to a vector comprising the polynucleotide disclosed herein. In embodiments, the polynucleotide may be cloned into an expression vector. The polynucleotide may be operably linked to a sequence within the expression vector such as, for example, any suitable promoters, enhancers, tags, or other control sequences that may provide for and/or facilitate the expression and/or the purification of the immunogenic peptide in the host cell. Generally, the term operably linked refers to a juxtaposition wherein the components described are in a relationship permitting them to function in their intended manner. For example, a regulatory sequence, such as a promoter, that is operably linked to a coding sequence is positioned in such a way that expression of the coding sequence is achieved under conditions compatible with the regulatory sequence. The polynucleotides encoding an immunogenic peptide or epitope include a recombinant DNA which is incorporated into a vector into an autonomously replicating plasmid or virus or into the genomic DNA of a prokaryote or eukaryote, or which exists as a separate molecule (such as a cDNA) independent of other sequences. The polynucleotides disclosed herein can comprise ribonucleotides, deoxyribonucleotides, modified nucleic acids, and any combinations thereof. Polynucleotides may also refer to single or double stranded forms of polynucleotides.

The nucleic acid molecule or vector may be introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in a gram negative and/or a gram positive bacterial cell. Exemplary vectors include those for expression in *E. coli* and *Salmonella*. Suitable expression vectors are known in the art and include, but are not limited to, plasmids, for example, pET plasmid (Novagen, now EMD Millipore, Billerica, Mass.). or the pQE plasmids (Qiagen, Valencia, Calif.). The vectors may contain one or more selectable marker genes, for example, ampicillin resistance gene or kanamycin resistance gene in the case of bacterial plasmid. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors.

The disclosure also provides aspects relating to host cells transformed with the vectors and polynucleotides discussed herein. In some embodiments, a bacteria cell, such as an *E. coli* cell, transformed with one of the nucleic acid sequence described above is provided. A host cell may be a transduced cell, which is generally prepared by the introduction of a nucleic acid molecule by molecular biology techniques that are generally known in the art. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration, and the like.

In some embodiments, the cells, polynucleotides, and vectors described herein may be used in the production of an immunogenic peptide, epitope, or antibody that is disclosed herein. In such embodiments, the method of production may comprise further optional purification of the expressed protein from a host cell used to produce the immunogenic peptide, epitope, or antibody.

In another aspect the disclosure relates to therapeutic composition comprising at least one antibody that inhibits growth of multiple strains of malaria. The composition may include at least one antibody that specifically binds to an epitope of AMA-1 within the 1e-loop. The antibody may bind within the sequence of SEQ ID NO: 1. In some embodiments, the composition further comprises an antibody that binds within domain III of the AMA-1 protein. In other embodiments, the compositions comprise at least one antibody of the present invention that binds to an epitope of AMA-1 within the sequence of SEQ ID NO: 2.

In further embodiments, the disclosure provides a composition comprising at least one antibody that specifically binds to an epitope of AMA-1 within the amino acid sequence of SEQ ID NO: 1 and at least one antibody that specifically binds to an epitope of AMA-1 within the amino acid sequence of SEQ ID NO: 2. In some embodiments, the combination of antibodies may provide synergistic inhibitory effects, as can be determined by any method known in the art such as, for example, a Growth Inhibition Assay (GIA) as described herein. The combination may further provide broad spectrum inhibition of malaria in a mammal such as, for example, a human. In some embodiments, broad spectrum inhibition includes inhibition of five or more stains of malaria, ten or more stains of malaria, fifteen or more strains of malaria, twenty or more strains of malaria, twenty-five or more strains of malaria, including P. falciparum, and including both field and laboratory strains. In embodiments, the combination of antibodies may provide a reduction in the $IC_{30}$ concentration that is greater than the additive effects of the individual antibody $IC_{30}$ concentrations. In some embodiments, the combination of antibodies may comprise 1B10 and 1E10; 4E8 and 1E10; or 4E11 and 1E10. In some embodiments, the composition further comprises an antibody that specifically binds AMA-1 within domain 2 (SEQ ID NO: 20). In some embodiments, the combination further include an antibody that finds use in prior vaccine compositions having limited protection such as, for example, monoclonal antibody 4G2 {Kocken, 1998}. In some embodiments, the combination of monoclonal antibodies includes 1B10, 4G2 and 1E10; 4E8, 4G2 and 1E10; or 4E11, 4G2 and 1E10.

It should be appreciated that the antibodies disclosed herein encompass the broadest sense of the term "antibody" and specifically covers, for example, single monoclonal antibodies (including agonist, antagonist, and neutralizing antibodies), antibody compositions with poly epitopic specificity, polyclonal antibodies, single chain anti-antibodies, and fragments of antibodies (see below) as long as they specifically bind a native polypeptide and/or exhibit a biological activity or immunological activity of this technology. Functional fragments or analogs of an antibody disclosed herein encompasses is a molecule having a qualitative biological activity in common with the antibody to which it is being referred. For example, a functional fragment or analog of an antibody can be one which can specifically bind to AMA-1. In one embodiment, the antibody can prevent or substantially reduce the ability of AMA-1 to bind its receptor RON2. In another embodiment, the antibody can prevent the proteolytic processing of AMA-1.

As is appreciated by those of skill in the art, the basic 4-chain IgG antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for g and isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. The structure and properties of the different classes of antibodies are generally described in the art, see, e.g., BASIC AND CLINICAL IMMUNOLOGY, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2. Antibody effector functions refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors; and B cell activation. A "native sequence Fc region" comprises an amino acid sequence identical to the amino acid sequence of an Fc region found in nature. Examples of Fc sequences are described in, for example, but not limited to, Kabat et al., supra (1991)).

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each variable in amino acid length and can span, for example, about 9-12 amino acids or fewer (e.g., from about 3 amino acids or more). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences Of Proteins Of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (Kabat et al., 1991) and/or those residues from a "hypervariable loop" (Chothia and Lesk J. Mol. Biol. 196:901-917 (1987)).

A monoclonal antibody refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic determinant. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies useful in the present invention can be prepared by the hybridoma methodology first described by Kohler et al., Nature, 256:495 (1975), or can be made using recombinant DNA methods in bacterial, eukaryotic animal or plant cells (see, e.g., U.S. Pat. No. 4,816,567). The "monoclonal antibodies" can also be isolated from phage antibody libraries using the techniques described in Clackson et al., Nature, 352:624-628 (1991), Marks et al., J. Mol. Biol., 222:581-597 (1991) or using the methods set forth in the Examples below.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., PNAS USA, 81:6851-6855 (1984)).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Antibodies that are humanized can retain the high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody fragments, discussed briefly above, typically comprise a portion of an intact antibody, such as the antigen binding or variable region of the intact antibody. Examples of antibody fragments include non-limiting examples of Fab, Fab', F(ab')2, and Fv fragments; diabodies; linear antibodies; single-chain antibody molecules; and multispecific antibodies formed from antibody fragments. The Fv is the minimum antibody fragment which contains a complete antigen-recognition and antigen-binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site. Single-chain Fv also abbreviated as "sFv" or "scFv" are antibody fragments that comprise the VH and VL antibody domains connected into a single polypeptide chain. The sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra. The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites.

In certain aspects, one or more substitutions of amino acids may be made to the sequences of the $V_H$ or $V_L$ chains of the antibodies of the present invention. In some instances, the one or more amino acid substitutions may be a conserved or non-conserved substitution. The one or more amino acid substitutions may be made as to alter or, in some cases, to increase the binding affinity of the antibody to the 1e loop (SEQ ID NO. 1) or region of domain III (SEQ ID NO. 2). In some instances, the conserved amino acids between the different monoclonal antibodies described herein are maintained within the $V_H$ or $V_L$ chains (more specifically within the CDR1, CDR2 and/or CDR3 domains of the $V_H$ or $V_L$ chains) and one or more of the non-conserved amino acids within these regions may be substituted. In certain embodiments, amino acid substitutions are made in only the VH and/or VL domain. In certain embodiments, the changes are made only in the VH domain. The same number of changes may be made in each domain or a different number of changes may be made in each domain. In certain aspects, one or more of the changes comprises a conservative amino acid substitution from the residue present in the "native" parental sequence. In other aspects, one or more of the changes is a non-conservative amino acid substitution from the residue present in the "native" parental sequence. When multiple substitutions are made, either in one or both the VH or VL domains, each substitution is independently a conservative or a non-conservative substitution. In certain aspects, all of the substitutions are conservative substitutions. In certain aspects, all the substitutions are non-conservative substitutions. In certain aspects, at least one of the substitutions is conservative. In certain aspects, at least one of the substitutions is conservative. In certain aspects, at least one of the substitutions is non-conservative. In further embodiments, and as discussed generally herein, framework region sequences may also be substituted while retaining most or all of the variable region amino acid sequences.

The ability of a particular antibody to recognize the same epitope as another antibody is typically determined by the ability of one antibody to competitively inhibit binding of the second antibody to the antigen, e.g., to AMA-1 or a fragment or fusion thereof. Any of a number of competitive binding assays can be used to measure competition between two antibodies to the same antigen.

Other conventional immunoassays known in the art can be used in the present invention. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Methods of preparing polyclonal antibodies are known to the skilled artisan. Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid or fragment thereof or a fusion protein thereof. The immunization protocol may be selected by one skilled in the art without undue experimentation.

Methods of preparing monoclonal antibodies are known in the art. Suitably, mice can be used to produce monoclonal antibodies. More specifically, a hybridoma is first prepared from a mammal immunized with said immune antigen. A B lymphocyte clone capable of producing a desired antibody is selected from the hybridoma, cultured, and collected. Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs., 130:151-188 (1992).

Suitably, the present technology provides one or more antibodies that show an $IC_{30}$ between 0.1 to 0.2 micrograms per ml.

In further aspects, the disclosure provides a vaccine composition comprising of four allelic proteins of AMA-1 from P. falciparum (sometimes referred to as QV or Quad-Vax). Suitably, the four allelic components of the vaccine composition comprise 3D7 (SEQ ID NO: 6), FVO (SEQ ID NO: 3), HB3 (SEQ ID NO: 4), and W2mef (SEQ ID NO: 5). The vaccine composition may further comprise an adjuvant, preferably an oil emulsion. Suitable oil emulsions include, but are not limited to, for example, Montanide ISA-720, AS02, AS01, GLA-SE, MF59, Alum, viruses, virus-like particles or nano-particles. As discussed herein, anti-QV antibodies were pan-reactive by ELISA and inhibited 22 non-vaccine parasite strains that included recent field isolates. Nucleic acid sequences encoding the 4 allelic strain include SEQ ID NO: 24 (3D7); SEQ ID NO: 10 (HB3), SEQ ID NO: 11 (W2mef); and SEQ ID NO: 13 (FVO). In some aspects, QV is used to treat a refractory form of malaria in a subject who is undergoing or has undergone treatment. Refractory malaria includes malaria that is not responsive to residual, prior, or a current treatment.

Immunogens and vaccines of the present technology provide one or more antibodies that inhibit in a growth or invasion inhibitory assay (GIA) against multiple strains of malaria. Methods to measure GIA are known in the art. A suitable method of measuring GIA which measures parasitemia after one invasion cycle, is a flow-cytometric method (WRAIR GIA) (See Haynes J D, Moch J K, Smoot D S (2002) Erythrocytic malaria growth or invasion inhibition assays with emphasis on suspension culture GIA. Methods Mol Med 72: 535-554, incorporated by reference in its entirety). Other methods are described within the Examples.

In one embodiment, the present technology provides a vaccine comprising an immunogenic peptide comprising the 1e-loop of the AMA-1 protein and a region of domain III of AMA-1 protein. In some embodiments, the 1e-loop is SEQ ID NO: 1 and the region of domain III is SEQ ID NO: 2.

In some embodiments, the present technology provides chimeric proteins of the AMA-1 protein of malaria that can be used in vaccine compositions to provide broad spectrum protection against multiple strains of malaria. Suitable chimeric proteins include, but are not limited to chimeric proteins that contain domain 1 of FVO, HB3, W2mef or 3D7 and domain 2 and 3 from one of the strains that is different than the stain used to provide strain 1. For example, suitable chimeric proteins include a chimeric protein containing domain 1 of FVO AMA-1 and domain 2 and 3 from 3D7 AMA-1 (FVO(D1)+3D7 (D2+3); SEQ ID NO: 14; nucleic acid SEQ ID NO: 15); domain 1 of HB3 and domains 2 and 3 from W2mef (HB3(D1)+W2(D2+3), SEQ ID NO: 16, nucleic acid sequence SEQ ID NO: 17); domain 1 of W2mef and domain 2 and 3 of HB3 (W2(D1)+HB3 (D2+D3); SEQ ID NO: 18, nucleic acid SEQ ID NO: 19).

In some embodiments of the present technology provides a vaccine composition comprising at least two chimeric proteins of AMA-1 which can elicit an immune response against multiple stains of malaria. Suitable, the vaccine composition comprises at least two chimeric proteins of the present technology. In some embodiments, the two chimeric proteins include (FVO(D1)+3D7 (D2+3); SEQ ID NO: 14) and HB3(D1)+W2(D2+3) (SEQ ID NO: 16). In other embodiments, the two proteins are FVO(D1)+3D7 (D2+3) (SEQ ID NO: 14) and W2(D1)+HB3 (D2+D3)(SEQ ID NO: 18).

Adjuvants that may be used in the vaccine compositions described herein may include, for example: Oil (mineral or organic) emulsion adjuvants such as Freund's complete (CFA) and incomplete adjuvant (IFA) (WO 95/17210; WO 98/56414; WO 99/12565; WO 99/11241; and U.S. Pat. No. 5,422,109); metal and metallic salts, such as aluminum and aluminum salts, such as aluminum phosphate or aluminum hydroxide, alum (hydrated potassium aluminum sulfate); bacterially derived compounds, such as Monophosphoryl lipid A and derivatives thereof (e.g., 3 De-O-acylated monophosphoryl lipid A, aka 3D-MPL or d3-MPL, to indicate that position 3 of the reducing end glucosamine is de-O-acylated, 3D-MPL consisting of the tri and tetra acyl congeners), and enterobacterial lipopolysaccharides (LPS); plant derived saponins and derivatives thereof, for example; surfactants such as, soya lecithin and oleic acid; sorbitan esters such as sorbitan trioleate; and polyvinylpyrrolidone; oligonucleotides such as CpG (WO 96/02555, and WO 98/16247), polyriboA and polyriboU; block copolymers; and immunostimulatory cytokines such as GM-CSF and IL-1, and Muramyl tripeptide (MTP). Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M. Suitable adjuvants include Montanide ISA-720, AS02, AS01, GLA-SE, MF59, Alum, viruses, virus-like particles or nano-particles, and the like.

As discussed herein, the vaccine compositions described herein suitably provide broader inhibition compared to a bivalent and two trivalent vaccines against a panel of laboratory and recently culture adapted isolates.

In alternative embodiments, the immunogenic peptides and epitopes can be incorporated into other therapeutically useful (e.g., non-vaccine) compositions including, for example, pharmaceutical compositions, and can further comprise a pharmaceutically acceptable carrier or excipient. Such pharmaceutical compositions may be administered to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, opthalmic, optical, intravenous (i.v.), intramuscular, intraglandular, intraorgan, or intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Additional components (e.g., preservatives, antioxidants, antimicrobial agents including biocides and biostats such as antibacterial, antiviral and antifungal agents) can also be incorporated into the compositions. For example, preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Pharmaceutical formulations and delivery systems appropriate for the compositions and methods disclosed herein are generally known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel ad Soklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

In aspects, the disclosure relates to methods of stimulating, inducing, promoting, increasing, or enhancing an immune response against malaria in a subject. In embodiments of these aspects, the method comprises administering to a subject an amount of an AMA-1 immunogenic peptide, epitope, nucleic acid, composition, antibody or combination thereof sufficient to stimulate, induce, promote, increase, or enhance an immune response against malaria in the subject. Such immune response methods can in turn be used to provide a subject with protection against a malaria infection or pathology, or one or more physiological conditions, disorders, illness, diseases or symptoms caused by or associated with malaria infection or pathology.

The methods disclosed herein may be used in therapeutic (following infection, during clinical presentation of malaria symptoms) or in prophylactic (prior to infection and development of malaria pathology) applications. As such, the methods disclosed herein include treatment of a subject having or at risk of having malaria or an infection or pathology relating to malaria, treating a subject diagnosed with malaria, preventing or protecting a subject from a malaria infection (e.g., provide the subject with protection against malaria infection), decreasing or reducing the likelihood that a subject contracts malaria, decreasing or reducing a subject's susceptibility to a malaria infection, inhibiting or preventing the progression or further development of a malaria infection in a subject, and decreasing, inhibiting, or suppressing transmission of the malaria from a host (e.g., a mosquito) to a subject.

As discussed above, the methods include administering an AMA-1 immunogenic peptide, epitope, nucleic acid, composition, antibody or combination thereof to treat a subject having or at risk of having a malaria infection or pathology. Accordingly, methods can treat the malaria infection or pathology, or provide the subject with protection from infection (e.g., prophylactic protection). Methods can also provide a subject with protection from or relief against or one or more physiological conditions, disorders, illness, diseases or symptoms caused by or associated with the malaria infection or pathology.

In particular embodiments, one or more disorders, diseases, physiological conditions, pathologies and symptoms associated with or caused by a malaria infection or pathology will respond to treatment. In some embodiments, the methods may reduce, decrease, suppress, limit, control or inhibit malaria numbers or titer; reduce, decrease, suppress, limit, control or inhibit pathogen proliferation or replication; reduce, decrease, suppress, limit, control or inhibit the amount of a pathogen protein; or reduce, decrease, suppress, limit, control or inhibit the amount of a malaria nucleic acid.

In some embodiments, the methods may result in any therapeutic or beneficial effect. Such effects may include reducing, inhibiting, limiting, delaying or preventing malaria infection, proliferation or pathogenesis. The effects may also decrease, reduce, inhibit, suppress, prevent, or control one or more adverse (e.g., physical or clinical) symptoms, disorders, illnesses, diseases or complications caused by or associated with malaria infection, proliferation or replication, or pathology (e.g., fever, chills, headache, sweats, fatigue, nausea, vomiting, muscle and/or back pain, dry cough, etc.). In further embodiments, treatment methods include improving, accelerating, facilitating, enhancing, augmenting, or hastening recovery of a subject from a malaria infection or pathogenesis, or one or more adverse symptoms, disorders, illnesses, diseases or complications caused by or associated with malaria infection, proliferation or replication, or pathology (e.g., fever, chills, headache, sweats, fatigue, nausea, vomiting, muscle and/or back pain, dry cough, etc.). In yet additional various embodiments, treatment methods include stabilizing infection, proliferation, replication, pathogenesis, or an adverse symptom, disorder, illness, disease or complication caused by or associated with malaria infection, proliferation or replication, or pathology, or decreasing, reducing, inhibiting, suppressing, limiting or controlling transmission of malaria from a host (e.g., mosquito) to an uninfected subject.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, disease or complication caused by or associated with malaria infection, proliferation or replication, or pathology (e.g., fever, chills, headache, sweats, fatigue, nausea, vomiting, muscle and/or back pain, dry cough). Thus, a satisfactory clinical endpoint is achieved when there is an incremental improvement or a partial reduction in an adverse symptom, disorder, illness, disease or complication caused by or associated with malaria infection, proliferation or replication, or pathology, or an inhibition, decrease, reduction, suppression, prevention, limit or control of worsening or progression of one or more adverse symptoms, disorders, illnesses, diseases or complications caused by or associated with malaria infection, merozoites numbers, titers, proliferation or replication, malaria protein or nucleic acid, or malaria pathology, over a short or long duration (hours, days, weeks, months, etc.).

A therapeutic or beneficial effect also includes reducing or eliminating the need, dosage frequency or amount of an active such as a drug or other agent (e.g., anti-malarial) used for treating a subject having or at risk of having a malaria infection or pathology. In addition, reducing or decreasing an amount of a malaria antigen used for vaccination or immunization of a subject to provide protection to the subject is considered a beneficial effect. A therapeutic or beneficial effect also includes a reduced need or use of therapeutic regimen, treatment protocol, subsequence vaccination or immunization process, or remedy. For example, a therapeutic benefit may be giving a subject less frequent or reduced dose or elimination of an anti-malaria treatment results.

Adverse symptoms and complications associated with malaria infection and pathology include, for example, e.g., fever, chills, headache, sweats, fatigue, nausea, vomiting, muscle and/or back pain, dry cough, etc. Other symptoms of malaria infection or pathogenesis are known to one of skill in the art and treatment thereof in accordance with the methods disclosed herein.

Methods and compositions include administration of immunogenic peptide, epitope, nucleic acid, composition, antibody or combination thereof to a subject prior to contact, exposure or infection by a malaria, administration prior to, substantially contemporaneously with or after a subject has been contacted by, exposed to or infected with a malaria, and administration prior to, substantially contemporaneously with or after malaria pathology or development of one or more adverse symptoms.

Compositions (including, e.g., immunogenic peptide, epitopes and antibodies), uses and methods in some aspects can be combined with any compound, agent, drug, treatment or other therapeutic regimen or protocol having a desired therapeutic, beneficial, additive, synergistic or complementary activity or effect. Exemplary combination compositions and treatments include multiple epitopes as set for the herein, multiple antibodies as set for herein, second actives, such as anti-malaria compounds, agents and drugs, as well as agents that assist, promote, stimulate or enhance efficacy.

Accordingly, embodiments of the methods disclosed herein encompasses combinations in which a method or use of the disclosure is used in a combination with any compound, agent, drug, therapeutic regimen, treatment protocol, process, remedy or composition, such as an anti-malarial or immune stimulating, enhancing or augmenting protocol, or pathogen vaccination or immunization (e.g., prophylaxis) set forth herein or known in the art. The compound, agent, drug, therapeutic regimen, treatment protocol, process, remedy or composition can be administered or performed prior to, substantially contemporaneously with or following administration of one or more immunogenic peptides, epitope, nucleic acid, composition, antibody or combination thereof.

Methods in which there is a desired outcome, such as a therapeutic or prophylactic method that provides a benefit from treatment, vaccination or immunization immunogenic peptide, subsequence, portion or modification thereof can be administered in a sufficient or effective amount. As used herein, a "sufficient amount" or "effective amount" or an "amount sufficient" or an "amount effective" refers to an amount that provides, in single (e.g., primary) or multiple (e.g., booster) doses. In some aspects, it can be provided alone or in combination with one or more other compounds, treatments, therapeutic regimens or agents (e.g., a drug), a long term or a short term detectable or measurable improvement in a given subject or any objective or subjective benefit to a given subject of any degree or for any time period or duration (e.g., for minutes, hours, days, months, years, or cured).

For example, to increase, enhance, improve or optimize immunization and/or vaccination, after an initial or primary administration of one or more immunogenic peptides to a subject, the subject can be administered one or more additional "boosters" of one or more immunogenic peptides. Such subsequent "booster" administrations can be of the same or a different formulation, dose or concentration, route, etc.

The term "subject" refers to an animal, typically a mammalian animal (mammal), such as a non human primate (apes, gibbons, gorillas, chimpanzees, orangutans, macaques), experimental animal (mouse, rat, rabbit, guinea pig) and humans. Subjects include animal disease models, for example, primate and other animal models of pathogen (e.g., malaria) infection known in the art.

Prophylaxis and prevention grammatical variations thereof mean a method in which contact, administration or in vivo delivery to a subject is prior to contact with or exposure to or infection. In certain situations it may not be known that a subject has been contacted with or exposed to malaria, but administration or in vivo delivery to a subject can be performed prior to infection or manifestation of pathology (or an associated adverse symptom, condition, complication, etc. caused by or associated with malaria). In other examples, the subject may have been exposed to one strain of malaria but not others.

Treatment of an infection can be at any time during the infection. Compositions, immunogenic peptides, or epitopes can be administered as a combination or separately concurrently or in sequence (sequentially) in accordance with the methods as a single or multiple dose e.g., one or more times hourly, daily, weekly, monthly or annually or between about 1 to 10 weeks, or for as long as appropriate, for example, to achieve a reduction in the onset, progression, severity, frequency, duration of one or more symptoms or complications associated with or caused by malaria infection, pathology, or an adverse symptom, condition or complication associated with or caused by a malaria. Thus, a method can be practiced one or more times (e.g., 1-10, 1-5 or 1-3 times) an hour, day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks, and any numerical value or range or value within such ranges.

In some aspects, a method of treating a refractory form of malaria in a subject who is undergoing or has undergone treatment is provided. Refractory malaria includes malaria that is not responsive to residual, prior, or a current treatment. The method comprises administering to the subject an immunogenic or vaccine composition in an amount effective to induce an immune response against SEQ ID NO:1 and SEQ ID NO:2 as herein described. In some aspects, the vaccine composition comprising at least four alleles of AMA-1. In some aspects, the four alleles comprise 3D7, FVO, HB3 and W2mef AMA-1 proteins.

Methods may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intra-spinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, or intralymphatic.

Doses can be based upon current existing protocols, empirically determined, using animal disease models or optionally in human clinical trials. Initial study doses can be based upon animal studies that is determined to be effective. Exemplary non-limiting amounts (doses) are in a range of about 0.1 mg/kg to about 100 mg/kg, and any numerical value or range or value within such ranges. Greater or lesser amounts (doses) can be administered. Doses can generally be determined by one skilled in the art in view of the age, weight, health, along with other factors generally taken into consideration for dosage formulations. Doses can vary and depend upon whether the treatment is prophylactic or therapeutic, whether a subject has been previously exposed to, infected with our suffered from malaria, the onset, progression, severity, frequency, duration probability of or susceptibility of the symptom, condition, pathology or complication, or vaccination or immunization to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a therapeutic or prophylactic benefit.

Methods of the invention also include, among other things, methods of diagnosing malaria infection in a subject, and malaria exposure of a subject. In one embodiment, a method includes contacting cells from a subject to one or more antibodies; and determining if the antibodies bind to the cells.

The vaccine compositions of the present technology preferably elicits an immune response in a subject against at least one or more conserved epitope on the AMA-1 protein, preferably at least two or more conserved epitopes, alternatively at least three or more conserved epitopes on the AMA-1 protein. In some embodiments, the one or more conserved epitopes can include one or more of the following, 1e-loop of AMA-1 or domain III of AMA-1. In some embodiments, the one or more conserved epitopes include SEQ ID NO:1 or SEQ ID NO: 2.

The immunogens and vaccines of the present technology can be used to elicit an immune response in a subject, preferably a mammal, more preferably a primate, more preferably a human. The immunogens or vaccine composition preferably elicits an immune response against at least one or more conserved epitope on the AMA-1 protein of *P. falciparum*, preferably at least two or more conserved epitopes, alternatively at least three or more conserved epitopes on the AMA-1 protein.

In another aspect, the disclosure relates to methods of inducing a targeted immune response in a patient suffering for *P. falciparum* infection comprising administering to the patient a vaccine composition comprising at least four alleles of AMA-1 protein. The immune response elicited by the vaccine composition comprising at least four alleles of AMA-1 protein target at least two epitopes of AMA-1, wherein one epitope is within the amino acids sequence of SEQ ID NO: 1 and one epitope is within the amino acid sequence of SEQ ID NO: 2; and wherein the targeted immune response provide for broad inhibition of *P. falciparum* infection. In embodiments, broad inhibition may include inhibition of at least five or more strains of *P. falciparum*, preferably more than at least ten strains of *P. falciparum*, preferably more than at least fifteen strains of *P. falciparum*, at least twenty strains of *P. falciparum*, at least twenty-five strains of *P. falciparum*.

In an aspect, the disclosure provides methods that can induce an immune response in a subject, comprising administering to the subject a vaccine composition comprising at least four alleles of AMA-1 protein. In some embodiments, the method provides a shift in immune response from generating antibodies that bind to polymorphic regions of the AMA-1 protein to generating antibodies that bind to conserved regions of the AMA-1 protein, for example, SEQ ID NO: 1 or SEQ ID NO: 2. In some embodiments of the method the subject may have undergone prior treatment, for example, with a vaccine composition having only a single allele of the AMA-1 protein, or a vaccine composition containing multiple alleles of AMA-1 which are not sufficient to induce a broad-based immune response in the subject. In some embodiments, the method comprises administering a vaccine composition comprising QV (QuadVax) as herein described.

Unlike immunization with a vaccine comprising one AMA-1 allele which produce inhibitory antibodies to only that particular vaccine strain (or closely related strains) but not broad antibody protection, the immunogens and vaccines of the present technology provides broad protection against multiple laboratory or field strains of malaria, in particular P. falciparum.

The immunogens or vaccines of the present technology can be used to elicit a broad spectrum immune response against multiple strains of malaria. Multiple strains of malaria include at least one strain of malaria, alternatively at least two strains of malaria, alternatively at least five strains of malaria, at least ten strains of malaria, at least fifteen strains of malaria, at least twenty strains of malaria, at least twenty five strains of malaria. In some embodiments, multiple strains of malaria include multiple strains of P. falciparum. Multiple strains of P. falciparum include at least one stain of P. falciparum, at least two strains of P. falciparum, at least three strains of P. falciparum, at least five strains of P. falciparum, at least ten strains of P. falciparum, at least fifteen strains of P. falciparum, at least twenty strains of P. falciparum, at least twenty five strains of P. falciparum, at least thirty strains of P. falciparum, at least thirty-five strains of P. falciparum. Suitable strains of P. falciparum are known in the art and include, but are not limited to, 7G8, M24, 102-1, CP803, CP806, CP830 CP845, CP887, HB3, GB4, MT/S1, C2A, W3mef, CSL-2, HCS-E5, 2006, 2004, X1E, E8B07, CAMP, D10, K1, T996, 3D7, FVO, among others. Suitable laboratory strains include HB3, GB4, MT/S1, C2A, W2mef, E8B07, CAMP, D10, K1, T996, 3D7, FVO, among others. Suitable field strains include, among others, CP803, CP806, CP830 CP845, CP887, CSL-2, HCS-E5, 2006, 2004, and XIE.

The disclosures of all patents, publications, including published patent applications, depository accession numbers, and database accession numbers are hereby incorporated by reference to the same extent as if each patent, publication, depository accession number, and database accession number were specifically and individually incorporated by reference.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges include integers within such ranges and fractions of the values or the integers within ranges unless the context clearly indicates otherwise. This construction applies regardless of the breadth of the range and in all contexts throughout this patent document. Thus, to illustrate, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-5 fold therefore includes 1, 2, 3, 4, 5, fold, etc., as well as 1.1, 1.2, 1.3, 1.4, 1.5, fold, etc., 2.1, 2.2, 2.3, 2.4, 2.5, fold, etc., and so forth.

It is to be understood, however, that the scope of the present invention is not to be limited to the specific embodiments described above. The invention may be practiced other than as particularly described and still be within the scope of the accompanying claims.

The Examples that follow are intended to be merely illustrative of the aspects and embodiments described above and should not be viewed as limiting to the scope of the appended claims.

EXAMPLES

Materials and Methods

Diversity Analysis.

Full-length AMA-1 sequence of 175 field isolates (FIG. 12) and 26 culture adapted strains were aligned by CLUSTAL (LASERGENE™). AMA-1 diversity (FIG. 1A) was visualized on a dendrogram created using DENDROSCOPE™ software available on the University of Tuebingen website.

Expression and Purification of Recombinant AMA-1 Proteins.

P. falciparum FVO AMA-1, HB3, AMA-1 and W2mef AMA1 genes, encoding amino acids 83-531 were codon optimized for expression in E. coli. The genes were cloned in-frame with hexa-histidine tag, into the BamHI and NotI sites of a modified pET32 plasmid (Novagen, now EMD Millipore, Billerica, Mass.) This plasmid contains a kanamycin resistance gene. The genes were sequenced on both strands. The final recombinant plasmid was transformed into Tuner DE3 cells (Novagen, now EMD Millipore, Billerica, Mass.) and expression of protein was induced by the addition to 0.5 mM IPTG in early log phase. Using small shake-flask expression cultures (e.g., 1000 mL cultures in 5000 mL flasks), it was found that majority of the FVO AMA-1 protein localized to the insoluble fraction. Glucose was added to 1% concentration during early culture fermentation in order to help inhibit gene expression until induction with IPTG. Protein expression level, plasmid retention and growth parameters were then compared using a 10 L fermentor (New Brunswick).

Master and Production Cell Bank:

120 ml APS Superbroth (Difco) supplemented with 1% glycerol, 1% glucose and 50 mg/ml Kanamycin was inoculated with a single colony of the E. coli expressing the FVO AMA-1 gene. At an $OD_{600}$ of 1.0 glycerol was added to the culture to a final concentration of 15% v/v. The culture was then aliquoted in 1 ml×100 cryovials and frozen at −80 C. This procedure was repeated using one of the Master cell bank vials as an inoculum to produce 100 Production Cell Bank (PCB) vials.

Fermentation:

APS media (above) was inoculated with 1 ml of a PCB vial and incubated in a shaking incubator at 37° C. for ~7 hrs. This was used as an inoculum for a large scale culture prepared in a 10 L New Brunswick fermentor. The fermentation was continued at 37° C. with agitation 400 rpm, air at 300 L/min, pressure at 3 psig, pH at 7.2. At OD600 of 7.0, IPTG was added to a final concentration of 0.5 mM, and was cultured for about 1 hr. The cells were harvested by centrifugation and stored at −80 C. The induction was confirmed by running un-induced and induced samples on a gel (PAGE) and staining with Coomassie blue.

Purification:

A small aliquot 10 g of the cell paste was thawed overnight at 4° C. This paste was suspended in 10 volumes (about 100 ml) of buffer A (250 mM Phosphate, 450 mM NaCl, 5 mM EDTA, pH 8.1). The suspension was homogenized and microfluidized. The cell lysate was centrifuged at 12,000 rpm on a Sorvall RC-5 centrifuge for 1 hr. The supernatant was removed from the centrifuge tube, and inclusion body pellet was washed and homogenized in 10 volumes (about 100 ml) of buffer B (20 mM Phosphate, 5 mM EDTA, pH 8.1). The suspension was centrifuged as before and the pellet was suspended by homogenization in 5 volumes (about 50 ml) buffer C (6M Guanidine Hydrochloride, 20 mM Phosphate, 500 mM NaCl, 5 mM EDTA, pH 8.1). The reconstituted inclusion body solution was centrifuged at 12,000 rpm for 90 min at 10° C. The solubilized proteins in the supernatant were refolded by rapid dilution into 50 fold excess volume of buffer D (20 mM Phosphate, 1 mM GSH, 0.25 mM GSSG, pH 8.1). After overnight refolding at 22° C., the refolding solution was cleared by continuous centrifugation at 14,000 rpm. The cleared refolding solution was then passed at 600 ml/min over a Ni-NTA SuperFlow column which was preequilibrated with 5 CV of buffer E (20 mM Phosphate, pH 8.1). The Ni column was washed with 20 CV buffer F (20 mM Phosphate, 0.25% N-lauroyl Sarcosinate, pH 8.1), followed by 10 CV buffer G (20 mM Phosphate, 5 mM imidazole, pH 8.1). Protein was eluted from the column using 5 L of buffer H (20 mM Phosphate, 250 mM Imidazole, pH 6.0). The protein eluted form Ni column was diluted 6 fold using buffer I (20 mM Phosphate, pH 6.0) and loaded on a SP Sepharose column that was preequilibrated in buffer I. Following the protein load, the column was washed with 5 CV buffer J (20 mM Phosphate, 150 mM NaCl, pH 6.0). Protein was eluted form the column using 4.5 L of buffer T (100 mM Phosphate, pH 8.1). This elution was then passed through a DEAE Sepharose column, pre-equilibrated in buffer T. The pass-through of the DEAE column was buffer exchanged in buffer R (20 mM Phosphate, 30 mM NaCl, pH 7.1 and concentrated using an A/G Ultrafiltration system.

AMA-1 Chimeras:

Crystal structures of AMA-1 (PDB references 1W81, 1Z40, 2Q8A) were used to design continuous surface chimeric proteins that displayed the various three dimensional structural elements of *P. falciparum* AMA-1 on the *P. berghei* AMA-1 scaffold. Chimeras were based on AMA-1 residues $83_{Gly}$ to $531_{Glu}$ of *P. falciparum* 3D7 sequence (accession number XP_001348015) and *P. berghei* AMA-1 ANKA strain sequence (XP_678057 or CAH96497). The chimeras displaying the domain1, domain2, domain3, the hydrophobic trough, the polymorphic face, conserved face and the domain2+1e-loop were termed as CryD1, CryD2, CryD3, HT, POLY, CONS and D2+1e respectively [9,23]. To avoid potential steric clashes CryD1, CryD2 and CryD3 were designed with overlapping (~7 Å) *P. falciparum* regions (FIG. 13,). Chimeric proteins displaying the linear domains of *Plasmodium falciparum* AMA-1 on the *P. berghei* AMA-1 scaffold were also produced. To make the linear domain chimeras (either interspecies *P. berghei*-*P. falciparum* chimeras or inter-strain *P. falciparum* domain-swapped chimeras), sequences of *P. falciparum* AMA-1 gene were PCR amplified using a synthetic gene template of *P. falciparum* AMA-1 (residues $83_{Gly}$ to $531_{Glu}$, accession number AAB36701). Scaffold sequences were amplified using primers that overlapped the *P. falciparum* DNA fragments. Full-length chimeric genes were then assembled by a PCR stitch reaction using external primers. Residue boundaries $83_{Gly}$-$303_{Cys}$ were treated as domain-1, residues $304_{Arg}$-$418_{Cys}$ as domain-2 and residues $419_{Leu}$-$531_{Glu}$ as domain-3. Five linear domain chimeras displaying the three domains: LinD1, LinD2, LinD3, LinD1+2 & LinD2+3 were produced. Similarly, three domain-swapped *P. falciparum* chimeras: FVO(D1)+3D7(D2+3) (protein sequence: SEQ ID NO: 14, nucleic acid sequence: SEQ ID NO: 15), W2(D1)+HB3(D2+3) (protein sequence: SEQ ID NO: 18; nucleic acid sequence: SEQ ID NO: 19) and HB3(D1)+W2mef(D2+3) (protein sequence: SEQ ID NO: 16; nucleic acid sequence: SEQ ID NO: 17) were produced. The genes for the chimeric proteins were cloned in pET32 based plasmid, expressed in *E. coli* Tuner strain and purified as above.

Rabbit Immunization.

Three rabbits per group each received three doses of 100 μg AMA-1 vaccine per dose emulsified in Montanide ISA720™ (Seppic Inc, Paris). The Quadrivalent vaccine (Quadvax) consisted of 25 μg each 3D7, FVO, HB3 and W2mef proteins; trivalent vaccines contained 33 μg of three allelic proteins and bi-allelic vaccine contained 50 μg of two allelic proteins. Emulsification was achieved by vigorous vortexing for 10-15 min and 1 ml vaccine was administered at multiple sites, subcutaneously, on the animal's back at four week intervals. Rabbits were bled out 2 weeks after the third vaccination. Sera were heat inactivated and stored at −70° C. until used for invasion inhibition assays.

ELISA.

ELISA protocol has been previously described [24]. End-point titer was the dilution that gave $OD_{405}$=0.5. Region-specific antibody titer was defined as: (End-point titer against a domain chimera/end-point titer against the full-length 3D7 AMA-1 protein)×100.

1-Cycle Flow-Cytometric GIA (WRAIR Method):

All inhibition assays in duplicate wells were performed by this method, unless stated otherwise [2]. Synchronized cultures at late-ring stage were diluted to 0.25-0.3% parasitemia and 2% hematocrit by using uninfected cells. The sera were heat inactivated before use and final culture volume was 60 μl. Parasites developed for 40 h at 37° C. and ring stages formed after the invasion cycle were stained with 1×SYBR green dye (BMA, Rockland, Me.) and counted by using BD FACSCalibur flow-cytometer. Controls wells were matched for the test strain and contained equivalent volume of adjuvant immunized serum control or PBS (for mAb and IgG GIA). Percent inhibition of invasion=1−(% parasitemia in test well/% parasitemia in control well).

GIA Reversal Using Allelic Proteins.

Serum pool of anti-QV or anti-3D7 AMA-1 were diluted to give ~60% inhibition of the 3D7 parasite. AMA-1 allelic proteins derived from 3D7, FVO, HB3, W2mef, 102-1, 7G8, or M24 strains (~150 μg/ml or 2.8 μM) were added to selectively deplete cross-reactive antibodies. Immunologically non-reactive *P. berghei* AMA-1 protein showed no inhibition reversal, while the homologous 3D7 AMA-1 showed complete reversal. GIA reversal=(inhibition in presence of 2.8 μM *P. berghei* AMA-1−inhibition in the presence of 2.8 μM test protein)/inhibition in presence of *P. berghei* AMA-1 at 2.8 μM.

GIA Reversal Using the Chimeras.

Region-specific inhibitory contribution of antibodies was determined using protein chimeras to reverse anti-QV or anti-3D7 AMA-1 mediated inhibition of 3D7 parasites. To ~60% inhibitory dose of serum pool, 4 μM chimeric proteins (~200 μg/ml) were added. Percent GIA reversal=(inhibition in presence of 4 μM *P. berghei* AMA-1−inhibition in the presence of 4 μM test chimera)/inhibition in presence of 4 μM *P. berghei* AMA-1.

2-Cycle, Purified IgG Invasion Inhibition Assay (Burnet Institute Method):

*P. falciparum* growth inhibition assay was performed as described previously [5,25]. Parasites were allowed to develop through two cycles of erythrocyte invasion for 72 hours at 37° C., stained with SYBR green dye (Invitrogen)

and infected cells counted using a FACSCantoII Flow-cytometer (BD). FACS counts were analyzed using FloJo™ (Ver 6.4.7) software. Percent inhibition of invasion=1−(% parasitemia in test well/% parasitemia in medium control well). All GIAs were run in a 96-well plate format, with each antibody tested in duplicate wells. Parasite growth inhibition is represented as the combined mean of two separate duplicate well assays set up on different days.

1-Cycle, Purified IgG Invasion Inhibition Assay (NIH Reference Center Method):

IgGs from rabbits were purified from pooled sera using protein G columns (Pierce Inc., Rockford, Ill.); the eluted fractions were dialyzed against RPMI 1640 (Life Technologies, Gaithersburg, Md.) and concentrated with centrifugal filter devices (Millipore, Billerica, Mass.). The purified IgGs were preadsorbed with uninfected human O+ erythrocytes, sterilized by filtration through a 0.22-μm filter and heat inactivated at 56° C. for 20 min before use in the assay. Late trophozoite and schizont stages of P. falciparum were allowed to develop and invade in the presence of either test or medium only control [4]. Cultures were maintained for 40 to 42h and relative parasitemia was determined by biochemical determination of parasite lactate dehydrogenase. Percent inhibition of the immune IgG was calculated as 100−[($A_{650}$ of test IgG−$A_{650}$ of normal RBCs)/($A_{650}$ of infected RBCs without any IgG−$A_{650}$ of normal RBCs)× 100].

Monoclonal Antibodies (mAb).

Monoclonal antibodies were developed by immunizing 3 mice multiple times with QV using the Precision Antibody's immunization technology (Columbia, Md.). Target specific antibody titers were determined by ELISA and a fusion was performed with B-cells from splenocytes and lymphocytes. The myeloma partner was derived from the cell line P3X63Ag8.653. Fused cells were selected in a HAT media and grown from a single cell. Hybridoma clone supernatants were screened by ELISA for reactivity to the four allelic proteins 3D7, FVO, HB3 and W2mef AMA1. Out of the total 38 clones obtained representative mAbs against all three domains were picked, preferably if they reacted to multiple allelic proteins. Selected mAbs were expanded in vivo using athymic nude mice and mAbs were purified from the ascetic fluid using a Protein G column (GE Healthcare). Other mAbs used in the study were: rat mAb 4G2dc1 that recognizes a cross-reactive conformational epitope [26]; rat mAb 58F8dc1 that recognizes the N-terminal region present only on unprocessed AMA-1; and mouse mAb 1F9 which binds to the residues on the CIL loop of 3D7AMA-1 [27]. Mab 4G2 and 58F8 were gifts from Dr. Clemens Kocken, Biomedical Primate Research Center, Rijswijk, The Netherlands.

Immuno-Blot.

1 μg of the AMA-1 proteins under non-reducing conditions was electrophoretically transferred to a nitrocellulose membrane immune-blots were performed essentially as described previously [24].

RON2 Peptide Competition ELISA.

Two μg/ml of RON2 peptide labeled with biotin at the N-terminus was immobilized on streptavidin plates (Thermal Fisher), followed incubation in BLOTTO Blocking Buffer (Pierce, Rockford, Ill.) for 1 hr. An equal volume of 0.0015 μg/ml of 3D7 AMA-1 and decreasing concentrations (150 μg/ml to 0.15 μg/ml) of mAbs (1E10, 1B10, 4E8, 4E11, 5A6, 1F9, 4G2 and 5G8) were added to the well. After 1 hr incubation the wells were washed and 1:5000 dilution of rabbit anti-AMA-1 polyclonal serum was used to detect bound AMA-1. ABTS substrate was added to the well after 1 hr incubation $OD_{450}$ was recorded.

Mutagenesis of $Lys_{230}$ to Ala in the 3D7 Form of AMA-1.

Mutagenesis of $Lys_{230}$ to Ala was carried out by the technique of splice overlap extension. PCR was used to amplify overlapped DNA fragments from the 3D7 AMA-1 ectodomain template in PHENH6 plasmid such that both PCR fragments contained the $K_{230}$ mutation. The splice overlapped PCR was performed using PHENH6 forward and reverse primers that incorporate the flanking region from PHENH6. Preparation of phage clones and phage ELISA against the mAbs was essentially as described previously [27].

AMA-1 Processing Inhibition Assay.

The processing inhibition assay on 3D7 strain parasites was performed essentially as described previously at 200 μg/ml final mAb concentration [28]. Merozoite pellets were harvested and analyzed for membrane-associated forms of AMA-1, while soluble forms were trapped by including a non-inhibitory concentration of anti-3D7 AMA-1 rabbit serum (1:2500 dilution) in the processing assay. Proteins were run on a non-reducing SDS-PAGE and AMA-1-specific bands were stained as described [16].

Monoclonal Competition ELISA.

MAbs were labeled using Lightning-Link® Horseradish Peroxidase kit (Innova Biosciences, Cambridge UK). AMA-1 protein of 102-1 strain was coated on ELISA plates (100 ng/well). Wells were blocked with 1% casein blocker for 2 hrs, washed with PBS-Tween and then 50 μl individual rabbit serum dilutions were added to the wells for 1 hr. To the same well, 50 μl of HRP-labeled mAbs, diluted to yield 1-1.5 $OD_{405}$, were added and incubated for 1 hr. Plates were washed and ABTS substrate was added. After 1 hr incubation, stop solution was added and plates were allowed to sit for 5 min before the $OD_{405}$ was recorded.

Statistical Analysis.

Multivariate Analysis of Variance (MANOVA) was used to compare mean GIA and ELIZA response against different strains using data from individual experimental animals. Dunnett's method is used to adjust p-values for the post hoc testing, comparing all groups to the QV group. Analysis of Variance (ANOVA) was used if the rabbit data were pooled and p values adjusted using either Dunnett's method (if all groups were compared to the QV) or Tukey's method (for all pair-wise comparisons). Two groups of data were tested unpaired using the Student t-test. ELISA data was $\log_{10}$ transformed to stabilize the variance before statistical analysis. Correlation between sequence distance and GIA was analyzed by linear regression. For synergy analysis, GIA over a range of 1E10 concentrations (0-4 mg/ml) was measured against 3D7 parasites in the presence or absence of an $IC_{30}$ concentration of mAb 4G2 (1.8 mg/ml). The observed inhibition by the mixture was compared to that predicted by an equation for Bliss independence as was applied to GIA by Williams et al. [20,21]. $GIA_{additive}$=[1−(1−% $GIA_{1E10}$)*(1−% $GIA_{4G2}$ at its $IC_{30}$)]. GIA dose response curves were used to predict the concentration of antibody that would give either 50% or 30% inhibition using non-linear curve function within Graphpad Prism® software.

Example 1

Anti-QV Inhibited Vaccine and Non-Vaccine Strains Similarly.

Groups of three rabbits were immunized with monovalent 3D7, FVO, HB3 and W2mef AMA-1 vaccines or an equivalent total antigen dose of a mixture of all four allelic proteins (QV). To determine the antigenic breadth of the induced antibodies, individual rabbit sera were analyzed by ELISA against recombinant proteins corresponding to seven diverse AMA-1 alleles (FIG. 1A). The QV antisera showed a high degree of cross-reactivity (>500,000 mean group titer against all 7 allelic proteins; FIG. 1B) whereas the monovalent vaccine antisera showed the typical strain-specificity of AMA-1 antibodies. Mean $\log_{10}$ ELISA titers of the four monovalent vaccines, tested against their respective homologous target strains, were not different from those induced by QV (MANOVA followed by Dunnett's test all p values>0.1). When the monovalent vaccine-induced titers were grouped together, the combined mean homologous strain titer was higher than the heterologous strain titer (ANOVA, followed by Tukey's test; FIG. 1C). In contrast, the QV group showed no difference in homologous and heterologous AMA-1 titers. In a GIA that measured parasitemia after one invasion cycle, using a flow-cytometric method (WRAIR GIA) [2], anti-QV showed similarly high levels of inhibition of homologous and four heterologous parasite strains (>49% inhibition at 1:5 whole serum dilution; FIG. 1D), while the GIA activity of the monovalent vaccines was dependent on the test strain. Homologous strain inhibitions of the QV group were similar to the homologous inhibitions induced by the monovalent vaccines (Dunnett's test p values>0.2). Similar to the grouped ELISA analysis, the combined mean homologous inhibition by the monovalent vaccine antisera was higher than heterologous inhibition, but no such difference for anti-QV was observed (FIG. 1E).

Using a 4-Way pool of antibodies against the monovalent vaccines, given separately to rabbits using Freund's complete adjuvant, Drew et al. have shown broad inhibitory coverage against diverse strains [3]. Hence we compared the activity of pooled QV rabbit sera to a 4-Way pool of sera from the four highest titer monovalent vaccine group rabbits (Mixed-Mono=anti-3D7+FVO+HB3+W2mef) (FIG. 1F). It is notable that GIA activity across strains for the QV pool was higher than the 4-Way pool (t-test, p=0.006). This data along with the higher heterologous coverage judged by GIA and ELISA (FIGS. 1C and 1E), indicates that anti-QV did not merely represent the sum of strain-specific antibodies and contrary to the dilution of inhibitory effect observed upon mixing polyclonal antisera, a mixed allele vaccine resulted in not only broad but also high level inhibition of parasite strains.

Example 2

A Combination of Four AMA-1 Variants (QV) May be Sufficient to Overcome Global AMA-1 Diversity.

In an independent vaccination experiment, groups of three rabbits were immunized in parallel with 100 micrograms of QV, or 100 micrograms mixtures of two (3D7+FVO) or three (3D7+FVO+HB3 and 3D7+FVO+W2mef) allelic proteins. All rabbits received three doses the vaccine per dose emulsified in Montanide ISA720™ (Seppic Inc, Paris). The Quadrivalent vaccine (Quadvax) consisted of 25 μg each 3D7, FVO, HB3 and W2mef proteins; trivalent vaccines contained 33 μg of three allelic proteins and bi-allelic vaccine contained 50 μg of two allelic proteins. Emulsification was achieved by vigorous vortexing for 10-15 min and 1 ml vaccine was administered at multiple sites, subcutaneously, on the animal's back at four week intervals.

Figure 2:
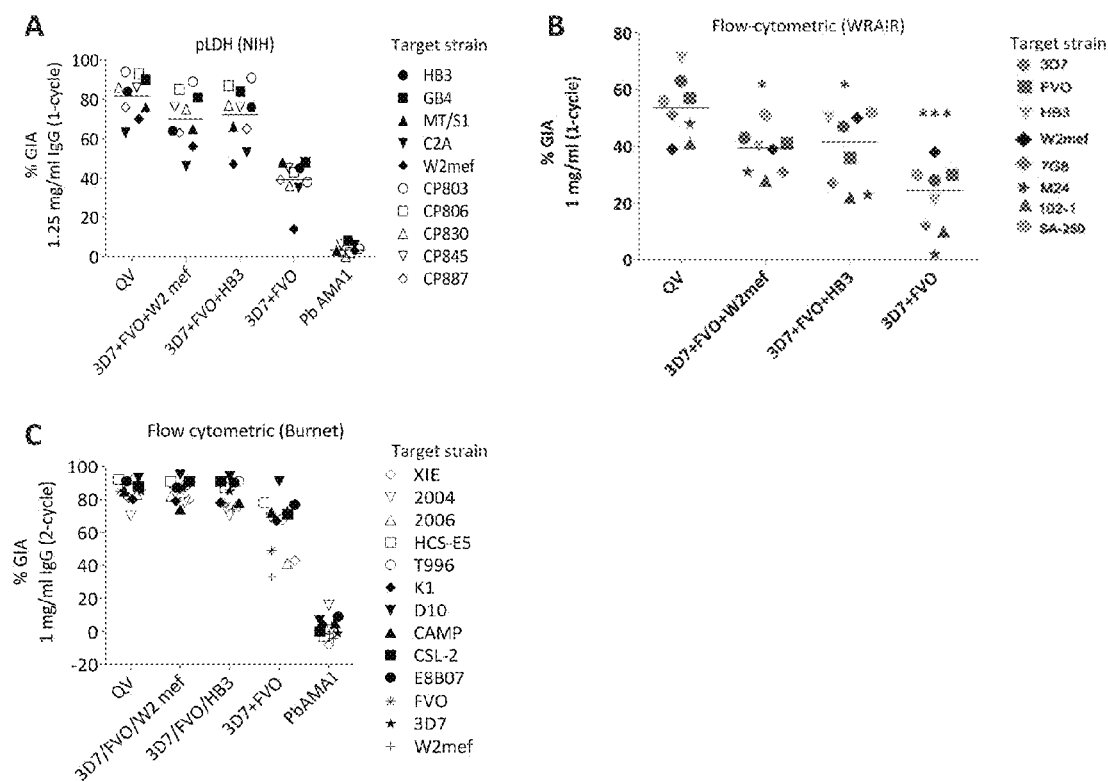
FIGS. 2A-2C show the following: (A) One-cycle GIA at 1.25 mg/ml using total IgG pool from 3 rabbits tested by the NIH pLDH assay. GIA of anti-QV was compared to trivalent and bivalent vaccine groups and antibodies against P. berghei AMA-1 (PbAMA1) were tested as the negative control. Strains CP803, CP806, CP830, CP845, and CP887 were recent culture adapted Cambodian isolates and HB3, GB4, MT/S1, C2A, W2mef were laboratory strains. Lines are median inhibition across strains. (B) One-cycle GIA at 1 mg/ml total IgG pool from 3 rabbits conducted by the WRAIR flow-cytometric method against 8 parasite strains. (*) indicates, $p<0.05$; (***) $p<0.0001$ (corrected for multiple comparisons). (C) Two-cycle GIA at 1 mg/ml pooled IgG conducted by the Burnet Institute flow-cytometric method. Strains CSL-2, HCS-E5, 2006, 2004, XIE were recently culture adapted field isolates from Africa, Asia and isolates E8B07, CAMP, D10, K1, T996 were laboratory strains [3].

Pooled IgG from each of the four vaccine groups were tested for inhibition of invasion against ten target parasite strains by the National Institutes of Health GIA reference laboratory using a parasite LDH based method following one invasion cycle [4]. The target strains included five recently culture adapted Cambodian isolates (labeled as CP in FIG. 2A). Adding a third allelic protein dramatically improved the cross-strain GIA activity of the bivalent vaccine, and a smaller increase in mean inhibition across strains was observed upon adding the fourth allelic protein to the vaccine although the mean inhibition across strains for the two trivalent vaccines was not statistically different from the QV. When tested for GIA activity against eight *P. falciparum* strains using the WRAIR flow-cytometric assay, inhibition across strains was significantly greater with the anti-QV IgG pool than with IgG induced by either of the two trivalent (p=0.033, 0.028) and the bivalent vaccine (p<0.0001) (FIG. 2B). A high level of cross-strain GIA activity with anti-QV IgG was independently verified in assays performed at the Burnet Institute (Melbourne, Australia) using a flow-cytometric assay that measured inhibition over two invasion cycles [5]. An additional ten parasite strains, five of which were recently culture adapted field isolates from south-east Asia and Africa [3], were all found to be highly inhibited by anti-QV and in this more sensitive assay the two trivalent antisera performed similar to the QV (FIG. 2C).

The full-length AMA-1 sequences, visualized on a dendrogram against 175 published AMA-1 sequences from Asian, South American and African origin (FIG. 1A), showed that the diversity of the 26 target strains, tested by GIA, was representative of the global AMA-1 diversity. Although GIA methodologies used by the three labs were different, they all suggested that a combination of three and preferably four QV allelic proteins may be all that is sufficient to provide coverage against global AMA-1 diversity.

Example 3

Generation and Mapping of Monoclonal Antibodies Against QV.

Figure 3:
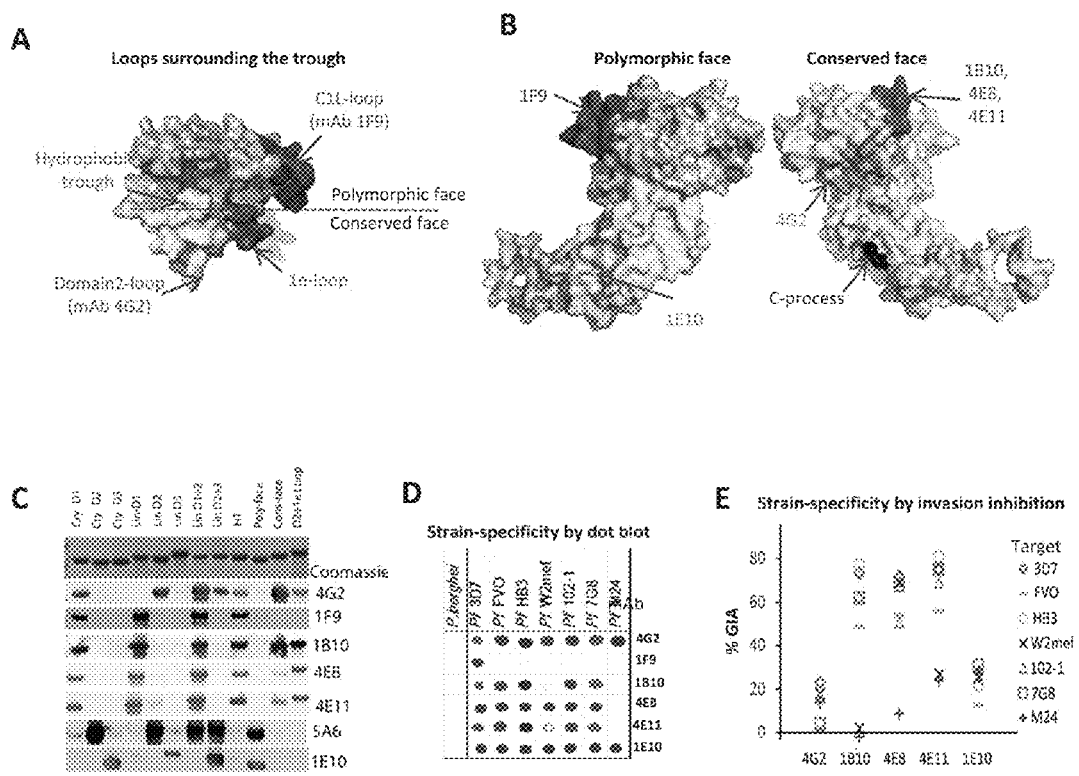
FIGS. 3A-3E show the following: (A) View of the hydrophobic trough and the surrounding loops showing approximate spatial location of mAb epitopes. (B) Polymorphic and conserved face of AMA-1. Domain-1 residues (light blue); domain-2 (yellow); domain-3 (magenta); C-terminal processing site (black); mAb 4G2 binding residues (orange); mAb 1F9 epitope centered on the C1L-loop (dark blue); and mAb 1B10, 4E8 and 4E11 epitopes on the 1e-loop (purple). (C) Coomassie blue stained and western blot panels showing chimeric proteins displaying the P. falciparum AMA-1 fragments on P. berghei AMA-1 backbone.
Figure 4:
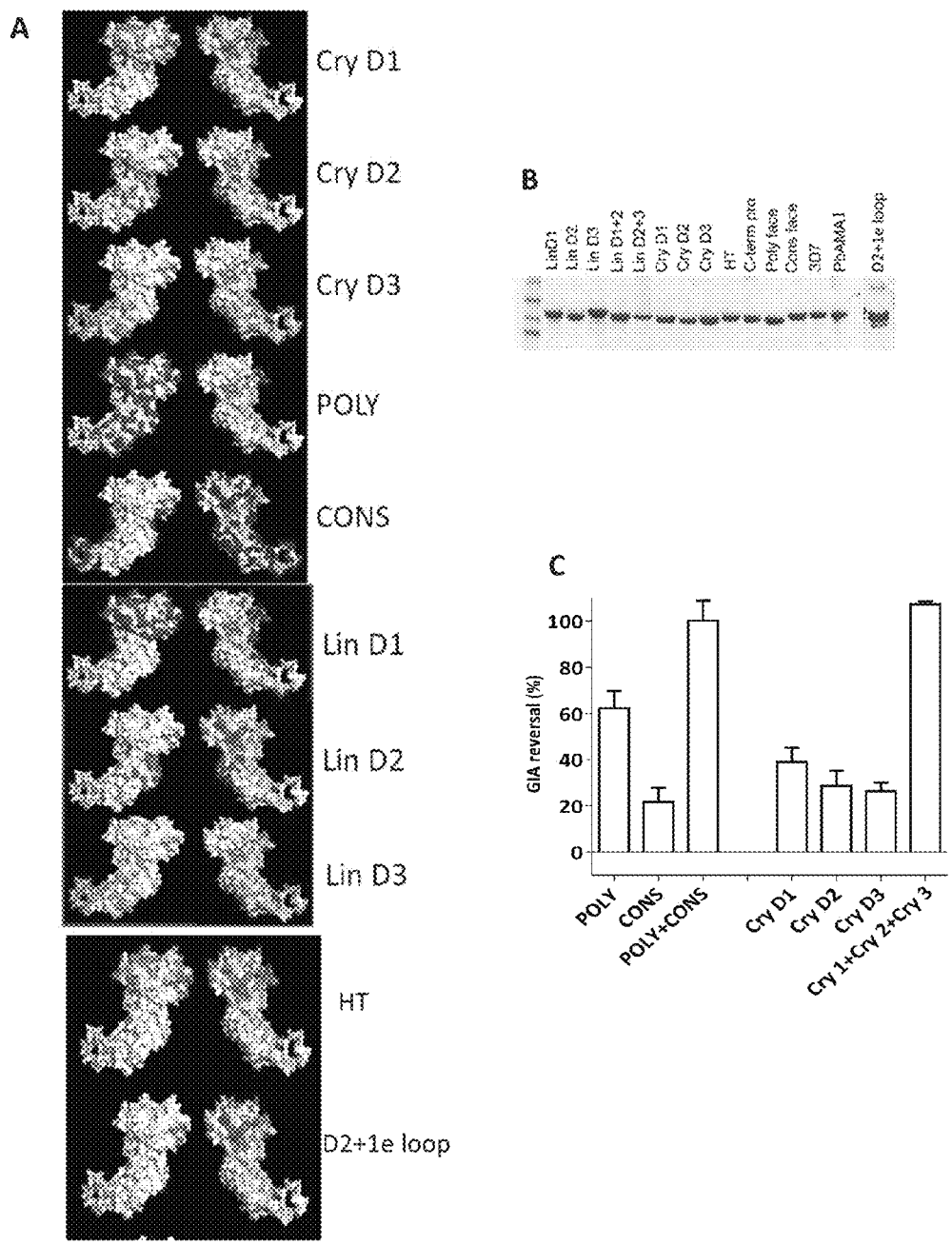
(FIG. 4). Chimeras were used to map representative mAbs. (D) Dot blot reactivity pattern of inhibitory mAbs against diverse P. falciparum AMA-1 allelic proteins and P. berghei AMA-1 control. (E) A cross-strain GIA against 7 parasite strains at 1 mg/ml mAb concentration.

To further characterize QV-induced antibodies, a panel of monoclonal antibodies (mAbs) were generated (FIG. 3). Binding domains for the mAbs were assigned by a Western blot against a panel of chimeric proteins that displayed *P. falciparum* sequences on a *P. berghei* AMA-1 scaffold (FIG. 4). There is 52% sequence identity between *P. falciparum* and *P. berghei* AMA-1. This level of identity is similar to that of *P. vivax* AMA-1 (58%) which is known to have an identical fold to *P. falciparum* AMA-1 [6], and is considerably higher than the identity to *T. gondii* AMA-1 (32% identity in domains I and II), known to have an identical fold in the core domain I+II region [7]. Hence, there is precedence for expecting that *P. berghei* and *P. falciparum* AMA-1 possess identical folds even though their surfaces are antigenically non-cross-reactive. Chimeras Cry-D1, Cry-D2, Cry-D3 displayed the contiguous surface regions of 3D7 AMA-1 domains-1, 2 and 3 based on the crystal structure (FIG. 4). Also displayed on the chimeras were combinations of the three linear domains of *P. falciparum* AMA-1 (Lin-D1, Lin-D2, Lin-D3, LinD1+2 and LinD2+3), as defined by the disulphide bond structure [8].

QV-induced hybridoma supernatants were prescreened for cross-reactivity to the four vaccine homologous allelic proteins by ELISA and domain chimeras by dot blot (not shown). Representative mAbs against each domain, preferably those that cross-reacted with three or more allelic proteins, were expanded and tested in a GIA at 1 mg/ml against the 3D7 target strain. While some domain-1 mAbs were strain-specific and others cross-reactive, mAbs against domain-2 were exclusively strain-specific for 3D7 and mAbs against domain-3 were mostly cross-reactive (Table 1). The two previously characterized AMA-1 mAbs 4G2 and 1F9 were accurately mapped by Western blotting with chimeric proteins, to regions surrounding the hydrophobic trough (domain-2 loop and domain-1 respectively). MAb 4G2 bound to chimera Lin-D2 and Cry-D1, and mAb 1F9 bound to Lin-D1 and Cry-D1 (FIG. 3A,B,C). Both of these mAbs were moderately inhibitory in a GIA against the 3D7 strain (Table 1). In contrast, three novel QV mAbs, 1B10, 4E8, 4E11, showed >60% inhibition and all three mapped to domain-1 on chimera Western blots. The domain-2 mAbs demonstrated low level inhibition (10% or less), while one of the domain-3 mAbs, 1E10, showed moderate inhibition, similar to mAb 4G2. The concentration of mAbs needed for 30% inhibition against the 3D7 target parasites ($IC_{30}$ concentration) was about 10-fold lower for the three domain-1 mAbs, 1B10, 4E8 and 4E11 (0.15, 0.15 and 0.22 mg/ml, respectively) as compared to mAbs binding to other regions of AMA-1 (mAb 4G2, 1.8 mg/ml; mAb 5A6, 3.5 mg/ml and mAb 1E10, 1.9 mg/ml).

TABLE 1

| mAb | Inhibition | Strain reactivity | Linear domain chimera reactivity | Crystal domain chimera reactivity | Domain |
|---|---|---|---|---|---|
| 1F9* | 17% | 1 | Lin-D1 | Cry-D1 | Domain-1 |
| 1B10 | 65% | 5 | | | |
| 4E8 | 67% | 6 | | | |
| 4E11 | 62% | 5 | | | |
| 4G2* | 22% | 7 | Lin-D2 | Cry-D1 | Domain-2 loop |
| 2B7 | −1% | 6 | | | |
| 5B7 | −2% | 6 | | | |
| 3D8 | −2% | 6 | | | |
| 2C10 | −2% | 3 | | | |
| 5A6 | 7% | 1 | Lin-D2 | Cry-D2 | Domain-2 |
| 91F | 9% | 1 | | | |
| 1F3 | 10% | 1 | | | |
| 1E10 | 20% | 7 | Lin-D3 | Cry-D3 | Domain-3 |
| 2C6 | 7% | 7 | | | |
| 1F4 | −3% | 7 | | | |
| 2D7 | −1% | 7 | | | |
| 6 E5 | 0% | 7 | | | |

Example 3

The Most Potent Inhibitory mAbs Map to the 1e-Loop of AMA-1 Domain-1.

To further define the mAb epitopes, additional chimeras were produced. Chimeras POLY and CONS displayed the polymorphic and conserved face of AMA-1, respectively; chimera D2+1e displayed the domain-2 loop together with the 1e-loop; and chimera HT displayed the rim of the hydrophobic trough and surrounding loops (FIG. 4) [9]. Consistent with the published location of the mAb 4G2 epitope on the domain-2 loop, this mAb reacted with chimeras displaying the conserved face (CONS) and the domain-2 loop (D2+1e chimera) [10] (FIG. 3A,B,C). Likewise, mAb 1F9 reacted with chimeras displaying the CIL or 1d loop on the rim of the hydrophobic trough (HT) [11]. The novel domain-1 mAbs 1B10, 4E8 and 4E11 all had a similar reactivity pattern, mapping to the conserved face. These mAbs also reacted to the D2+1e chimera, displaying the *P. falciparum* domain-2 and 1e-loops, but no reactivity to the Lin-D2 chimera containing the domain-2 loop was observed. This suggested that the epitope of the most potent domain-1 mAbs 1B10, 4E8 and 4E11 encompassed the 1e-loop. The moderately inhibitory domain-3 mAb 1E10 mapped to the polymorphic face (FIG. 3B,C).

Example 4

Broadly Inhibitory AMA-1 mAbs Map to the Conserved Face and Domain-3.

Breadth of mAb recognition was tested by a dot blot against 7 AMA-1 allelic proteins (FIG. 3D and Table 1). The domain-2 loop-binding mAb, 4G2, and the novel domain-3 mAb, 1E10, bound to all 7 AMA-1 alleles. In a parallel invasion assay these two mAbs weakly inhibited the corresponding parasite strains, confirming that they recognized strain-conserved, broadly inhibitory epitopes (FIG. 3E). The three most potent 1e-loop mAbs (1B10, 4E8 and 4E11) recognised most but not all protein variants. GIA confirmed these results as strain W2mef escaped inhibition by mAbs 1B10 and 4E11, and strain M24 was refractory to inhibition by all three 1e-loop mAbs. A negative control mAb, 58F8 which recognizes the N-terminal region of AMA-1, did not show significant invasion inhibition and mAb 5A6, which bound to a strain-specific domain-2 epitope, inhibited only the 3D7 strain (FIG. 3E).

Example 5

AMA-1 Antibodies Target Two Different Biological Processes.

Figure 5:
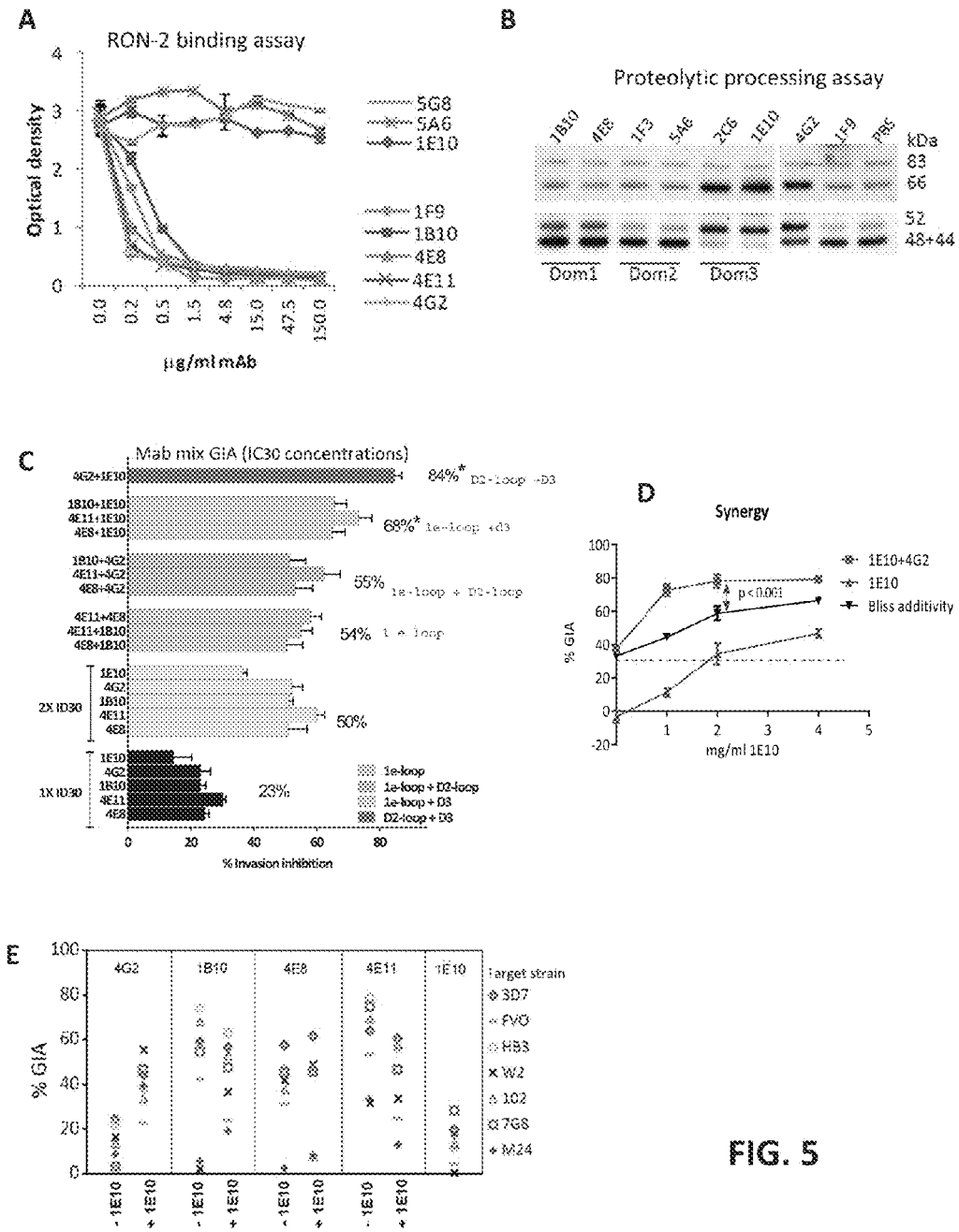

GIA activity of AMA-1 antibodies has been associated with inhibition of two biological processes: RON2 protein binding and AMA-1 proteolytic processing. Representative mAbs against all three domains were analyzed to determine if they blocked the interaction of AMA-1 with its receptor, RON2 [12-14], or if they could inhibit the proteolytic cleavage of the 66 kDa membrane bound AMA-1 to the 48+44 kDa soluble forms which are shed [15,16] [17]. The mAbs that bound to loops adjacent to the hydrophobic trough (1F9, 1B10, 4E8, 4E11, 4G2) blocked the binding of RON2 peptide to AMA-1 (FIG. 5A). RON2 binding was not altered by mAbs that bound to domain-2 (mAb 5A6), domain-3 (mAb 1E10), or the N-terminal pro-domain (mAb 5G8). Secondary proteolytic processing of AMA-1 on 3D7 strain parasites was blocked by mAbs binding to domain-3 (2C6, 1E10). Inhibition of processing was indicated by increased intensity of the merozoite surface associated 66 kDa form and the 52 kDa product of anomalous AMA-1 processing, combined with reduced intensity of the products of normal processing (co-migrating 44+48 kDa bands) [18] [16]. In contrast, mAbs binding to domain-1 (1B10, 4E8, 1F9), or domain-2 (1F3, 5A6) did not inhibit AMA-1 processing (FIG. 5B). Some alteration of processing was also detectable in presence of the mAb 4G2, probably due to the proximity of the base of the domain-2 loop to the C-terminal processing site at $Thr_{517}$ (FIG. 3B) [19].

Example 6

Domain-3 Antibodies Enhance the Inhibitory Activity of Broadly Inhibitory Conserved Face Antibodies.

To test if broadly inhibitory antibodies showed additivity or synergistic inhibitory effects, we analyzed selected mAbs in a GIA against 3D7 parasites at their respective $1 \times IC_{30}$ concentration (black bars; average inhibition, 23%) and at $2 \times IC_{30}$ concentration (gray bars; average inhibition, 50%) (FIG. 5C). When pairs of mAbs binding to spatially proximal epitopes were mixed at their respective $1 \times IC_{30}$ concentrations (1e-loop mAb mixtures in green or 1e-loop+domain-2 loop mAb mixtures in blue), the resulting inhibitions were not different from the 2×$IC_{30}$ concentration of individual mAbs. However, when mAbs binding to spatially distant epitopes were mixed at their $IC_{30}$ concentration (1e-loop+domain-3 mAbs in orange or domain-2 loop+ domain-3 mAb in red), the average inhibitions were significantly higher than that of the 2×$IC_{30}$ concentration of individual mAbs (p<0.05 corrected for multiple comparisons). The most potent inhibitory combination, mAb 1E10+ 4G2, was tested to confirm synergy using the "Bliss independence" equation recently used to discern synergistic antibody combinations by Williams et al. [20,21]. In a GIA against 3D7 parasites, a fixed $IC_{30}$ concentration of mAb 4G2 was mixed with a range of concentrations of mAb 1E10 (FIG. 5D) and synergy was assumed if the combination inhibited better than predicted by Bliss independence. The observed inhibition of the 4G2+1E10 mAb combination (red line) was higher than the predicted GIA activity (black line), thus confirming synergy (p<0.0001 for all data points, corrected for multiple comparisons). In a GIA against 7 diverse parasite strains, only the mAb 1E10+4G2 combination showed enhanced inhibition across strains (FIG. 5E, p=0.002). Thus domain-3 antibodies, which by themselves were not potent inhibitors, could synergize with antibodies binding to a strain-transcending epitope on the conserved face, domain-2 loop.

Example 7

QV Focuses the Immune Response Towards Domain-3 and the Conserved Face Epitopes.

Figure 6:
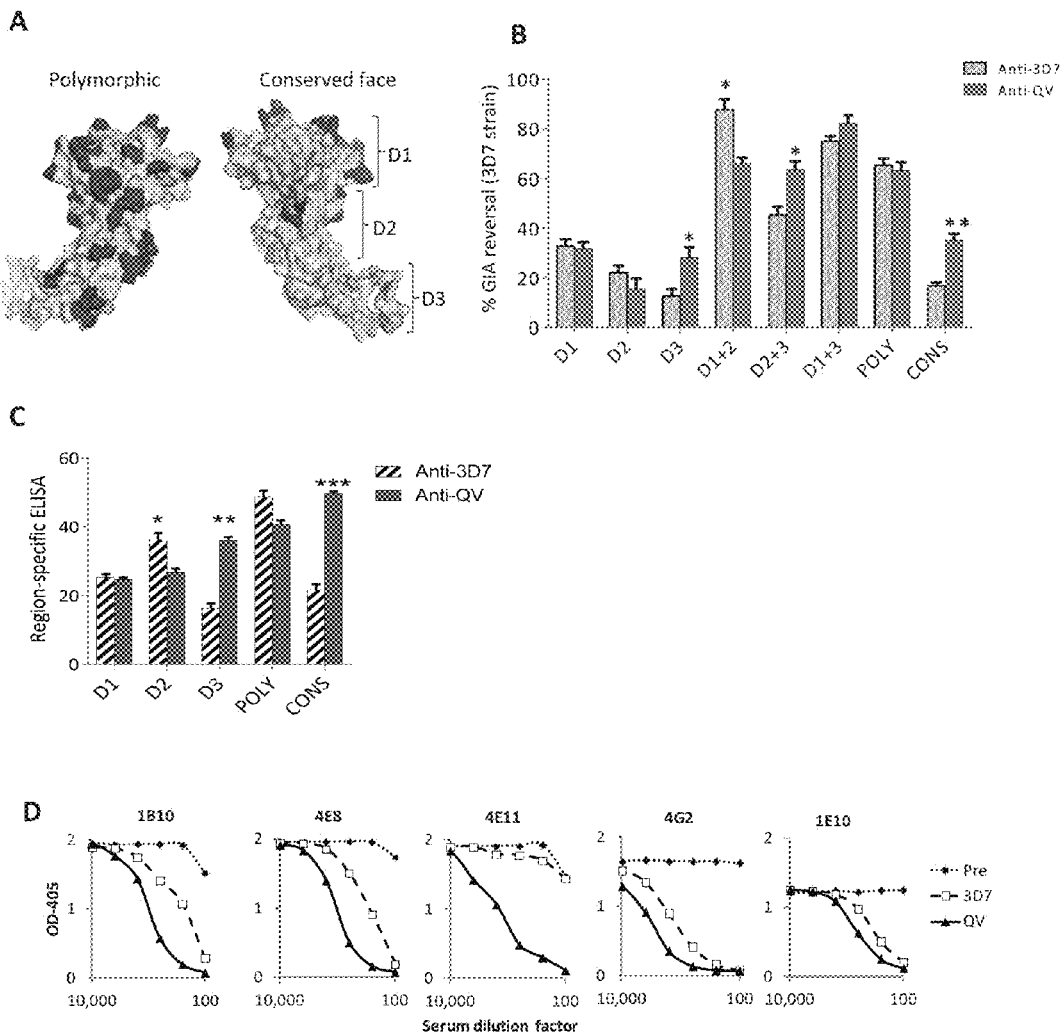
FIGS. 6A-6D show the following: (A) Distribution of high frequency polymorphisms on the three domains (D1, 2, 3), the polymorphic face and the conserved face of AMA-1. (B) Region-specific inhibitory contributions determined by adding chimeras to reverse anti-3D7 or anti-QV serum pool mediated GIA activity (approximately 60% starting GIA activity) against 3D7 parasites. Reversal using chimeric proteins CryD1, CryD2, CryD3, Cry D1+CryD2, CryD2+CryD3, CryD1+CryD3, POLY and CONS (4 µM, ~200 µg/ml final concentration) was determined with respect to $P.$ $berghei$ AMA-1 as the control. Mean+s.e.m. of 3 experiments and (*) indicates statistical significant p value of t-tests comparing anti-3D7 and anti-QV reversals. (C) Region-specific ELISA with pooled sera (% of total) values calculated as the ratios of end-point titers against a 3D7 chimera relative to the end-point titer against 3D7 AMA-1 protein (mean+s.e.m. of triplicates in a representative of three experiments). (D) Competition ELISA shows the binding of HRP labeled mAbs (mean $OD_{405}$ of 2 wells) to heterologous 102-1 AMA-1 protein. The mAb binding was competed out using serial dilutions of polyclonal anti-3D7 or anti-QV or pre-immune rabbit serum pools (x axis). Shown is a representative of two experiments.

Using the strain-specific anti-3D7 as the reference, we conducted differential mapping of the polyclonal anti-QV inhibitory response. In a GIA against 3D7 strain, equivalent final concentration of 3D7 chimeric proteins CryD1, CryD2, CryD3, CryD1+CryD2, Cry D2+CryD3, CryD1+CryD3, CONS and POLY were added to deplete region-specific antibodies against domains-1, 2, 3, 1+2, 2+3, 1+3, conserved face and polymorphic face, respectively (FIG. 6A). The extent of GIA reversal was used to dissect region-specific inhibitory contributions (FIG. 6B). For the anti-3D7 IgG, mAb mapping data would have predicted domain-1 to have the highest inhibitory contribution, however, the D1 chimera caused only 33% reversal as compared to 87% reversal by the mixture of D1 and D2 chimeras. This result was not surprising because vaccination with AMA-1 domains has previously shown that antibodies to these two domains are needed for high level GIA [22]. Between the two faces of AMA-1, the polymorphic face contributed more towards the inhibition (65% reversal) than the conserved face antibodies (16% reversal).

Comparing anti-3D7 and anti-QV GIA reversal showed increased levels of cross-reactive antibodies in anti-QV correlated with increased GIA reversal by chimera combinations that contained domain-3 (D3, p=0.0095; D2+3, p=0.0092) and the overall reversal for D1+3 chimera was the highest for anti-QV (FIG. 6B). Conversely, D2 (not statistically significant) and D1+D2 (p=0.0035) responses for anti-QV were lower than anti-3D7. Between the two faces, the response to polymorphic face was unchanged while enhanced conserved face inhibitory contribution was observed in anti-QV (p=0.0006). A region-specific ELISA using chimeric proteins as coat antigens also shown that QV induced higher levels of domain-3 (p=0.0002) and conserved face (p<0.0001) antibodies and reduced domain-2 antibodies (p=0.008) (FIG. 6C). Thus, as compared to the strain-specific monovalent 3D7 AMA-1 vaccine, QV induced an immunogenicity shift in favor of two less-polymorphic regions on AMA-1: the conserved face and domain-3 while the response to domain-2 was reduced.

A mAb competition ELISA was performed to determine the ability of anti-3D7 and anti-QV serum pool to inhibit the binding to labelled cross-reactive mAbs (1B10, 4E8, 4E11, 4G2 and 1E10) to a non-vaccine strain 102-1 AMA-1 (FIG. 6D). A lower concentration of anti-QV was required to compete out mAbs 1B10, 4E8, 4G2, 1E10 and, strikingly, antibodies competing for at least one broadly inhibitory epitope defined by mAb 4E11 epitope on the conserved face 1e-loop were present only in anti-QV, providing further proof of a structural shift of immunogenicity in favor of conserved epitopes.

Example 8

Quadvax Like Response can be Generated Using Inter-Strain Chimeric Proteins.

Figure 7:
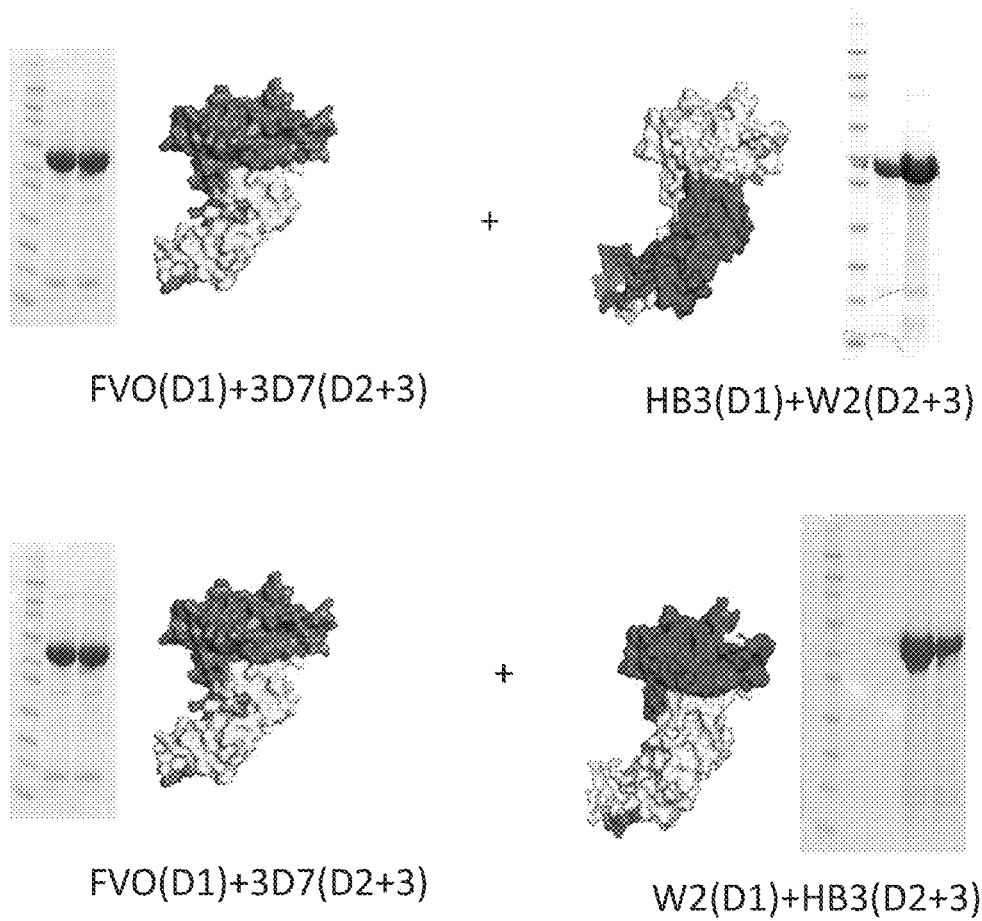
FIG. 7 depicts construction of domain-swapped chimeras: In the first domain chimera, linear domains of FVO (domain-1) and 3D7 (domains-2+3) were fused and the protein was purified to homogeneity as seen on the coomassie stained gel. Likewise, two additional chimeras where W2mef (domain-1) was fused to HB3 (domain-2+3) or HB3 (domain-1) was fused to W2mef (domains-2+3).
Figure 8:
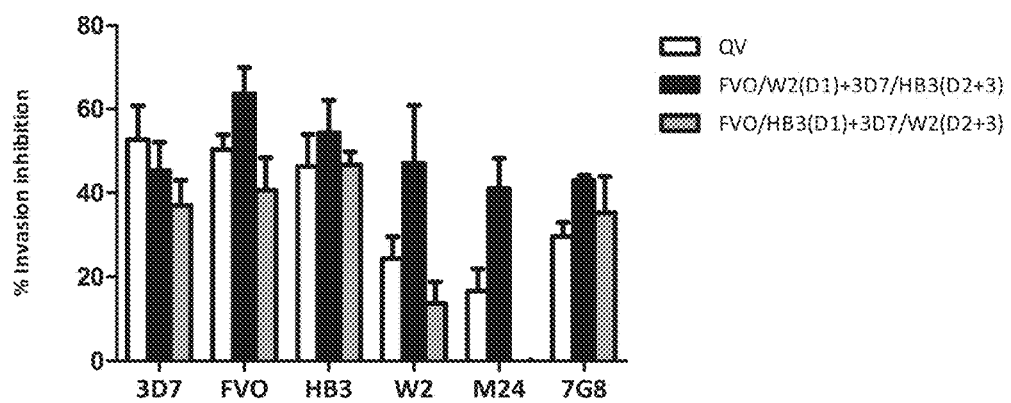
FIG. 8 shows GIA activity of whole serum on 3 individual rabbit sera at 20% concentration against six target parasite strains. The data are mean of 3 rabbits tested in a single experiment. The vaccine groups were QV (white bar); a mixture of FVO(D1)+3D7(D2+3) and W2(D1)+HB3(D2+3) (black bar) or a mixture of FVO(D1)+3D7(D2+3) and HB3(D1)+W2mef(D2+3) (gray bar).

The QV approach would require us to manufacture four individual vaccine components. We then tested if epitopes from the four AMA-1 proteins could be included in only two domain-swapped chimeric proteins (FIG. 7). The first chimeric protein produced contained the domain-1 of FVO AMA-1 and domains-2+3 of 3D7 AMA-1, this chimera was designated as FVO(D1)+3D7(D2+3). Two additional chimeric proteins were produced containing the domain-1 of HB3 and domains-2+3 of W2mef or the domain-1 of W2mef and domains-2+3 of HB3, these chimeras were termed HB3(D1)+W2(D2+3) and W2(D1)+HB3(D2+3) respectively. Fifty micrograms of purified FVO(D1)+3D7(D2+3) chimera was mixed with either 50 micrograms of HB3(D1)+ W2(D2+3) or with 50 micrograms of W2(D1)+HB3(D2+3) proteins to constitute two bi-allelic chimeric vaccine formulations. These two chimeric vaccines were compared to a 100 microgram dose of QV administered as 3 doses to groups of 3 rabbits. After three immunizations, individual antisera were tested in a GIA at 20% serum dilution. Remarkably, the bi-allelic chimeric mixture of FVO(D1)+ 3D7(D2+3) and W2(D1)+HB3(D2+3) performed as well if not better than the QV against six different target strains, two of which 7G8 and M24 were not homologous to any of the vaccine components (FIG. 8). We therefore concluded that chimeric proteins can be a way to deliver the QV as a two-component vaccine.

Example 9

Figure 9:
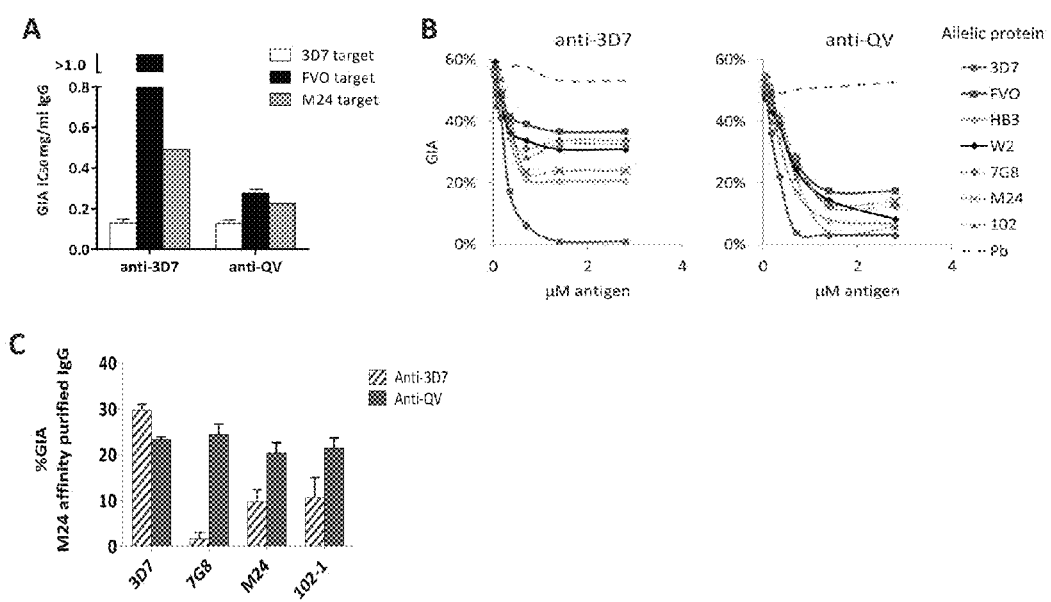
FIGS. 9A-9C show the following: (A) $IC_{50}$ values against three target strains for the monovalent anti-3D7 and anti-QV antibodies that were bound and eluted from a 3D7 AMA-1 affinity column (B) GIA reversal comparing the ability of AMA-1 allelic proteins to reverse anti-QV or anti-3D7 serum pool mediated inhibition of 3D7 parasite strain invasion. $P.$ $berghei$ AMA-1 was used as the negative control. The data is representative of 2 experiments. (C) GIA of anti-3D7 and anti-QV IgG eluted from a M24 AMA-1 affinity column and tested at 0.15 mg/ml against 3D7 or three non-vaccine parasite strains (7G8, M24 and 102-1). Mean+s.e.m from 3 experiments is shown.
Figure 10:
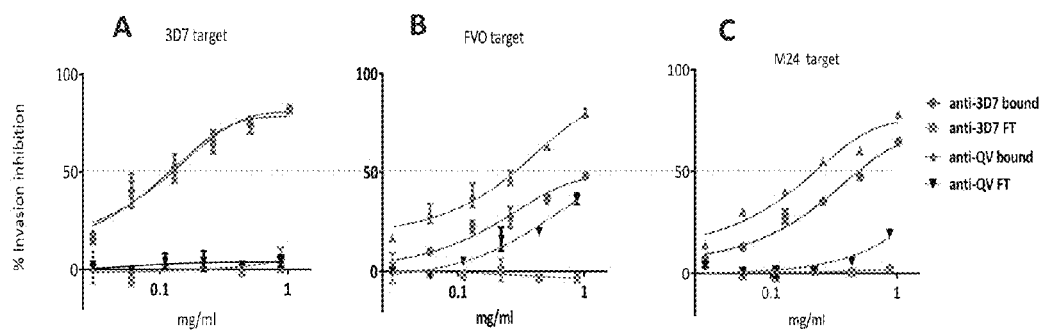
FIGS. 10A-10C show the following: GIA with affinity purified antibodies used to calculate the $IC_{50}$ (red and blue lines). Anti-3D7 and anti-Quadvax IgG were affinity purified over a 3D7 AMA-1 column. Bound/eluted (bound) or the flow-through fractions (FT; orange and green lines) were adjusted to equivalent IgG concentration and tested against 3D7 (10A), FVO (10B) and M24 (10C) parasite strains. Mean+s.e.m. of 3 independent experiments against 3D7 and FVO strains and one experiment in triplicate against the M24 strain are plotted.

Vaccination Using Four Allelic Proteins of AMA-1 (QV) Produced High Levels of Broadly Inhibitory Antibodies Against Multiple Strains of Malaria A 3D7 AMA-1 affinity column was employed to isolate antigen-specific antibodies induced by QV and the homologous monovalent 3D7 AMA-1 vaccine. More than 4 times as much anti-3D7 IgG was required for 50% inhibition ($IC_{50}$) of heterologous strains as required for 50% inhibition of 3D7 parasites (FIG. 9A and FIG. 10). In contrast, the anti-QV $IC_{50}$ against 3D7, FVO and M24 strains were similarly low. Notably, the flow-through fraction of anti-QV (unbound antibodies) still showed some level of inhibition of FVO and M24 parasites, while the flow-through of anti-3D7 did not (FIG. 10).

Figure 11:
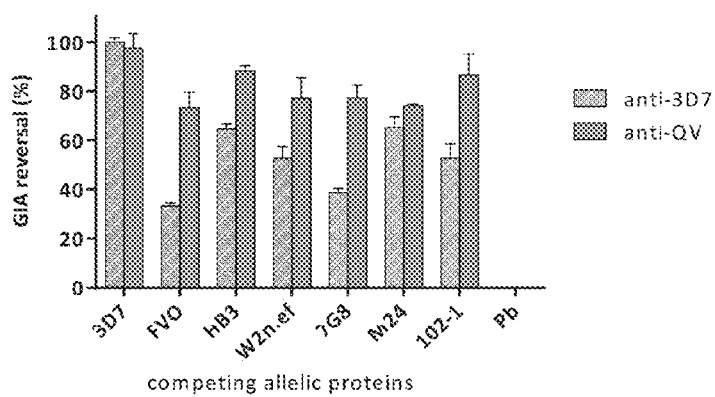
FIG. 11 illustrates reversal of GIA activity using diverse protein alleles. Anti-3D7 or anti-QV serum pools were diluted to yield ~60% inhibition of 3D7 parasite strain. Seven AMA-1 allelic proteins (3D7, FVO, HB3, W2mef, 7G8, M24 and 102-1) were added to the invasion inhibition assay (2.8 µM or ~150 µg/ml) to compete out the availability of cross-reacting antibodies. Bars are mean+s.e.m of three experiments. Percent reversal of inhibition=(inhibition in presence of $P.$ $berghei$ AMA-1–inhibition in the presence of the test antigen)/inhibition in presence of $P.$ $berghei$ AMA-1.

Since anti-3D7 and anti-QV sera showed similar inhibitory activities against the 3D7 target strain, we next determined if both antisera targeted a similar proportion of strain-specific and cross-reactive epitopes. A serial dilution of soluble antigens from seven diverse AMA-1 strains, were used to selectively deplete cross-reactive antibodies from the sera which were then tested in a GIA against 3D7 parasites (FIG. 9B). Vaccine strain (solid lines) and non-vaccine strain (dotted lines) AMA-1 proteins similarly reversed anti-QV mediated inhibition, whereas the anti-3D7 inhibition was completely reversible only by the homologous antigen. At saturating antigen concentrations, the three non-vaccine allelic proteins 7G8, M24, and 102-1 were significantly less effective at reversing the inhibition of anti-3D7 antibodies than they were at reversing the inhibition of anti-QV antibodies (average reversal 52% vs. 79%; t-test p<0.0001) (FIG. 11).

We also directly compared the relative inhibitory activities of the cross-reactive antibody fraction by affinity purifying anti-3D7 and anti-QV IgG over a non-vaccine strain M24 AMA-1 column (FIG. 9C). The net amount of anti-3D7 that bound to the M24 AMA-1 column was lower (8% by weight) than anti-QV (51%) and, despite affinity purification, the cross-reactive fraction of anti-3D7 still showed strain-specific inhibition (highest response against 3D7) which was significantly higher than its inhibition of 7G8, M24 and 102-1 (p=0.0014, 0.0074, 0.0096 respectively). There was no significant difference among the 3D7, 7G8, M24 and 102-1 strains in the level of inhibition by anti-QV IgG (FIG. 9C). These data showed that, not only did QV induce higher levels of cross-reactive antibodies than the monovalent 3D7 AMA-1 vaccine, but a higher proportion of the anti-QV antibodies targeted conserved inhibitory epitopes on the parasite AMA-1.

Example 10

Exemplary Monoclonal Antibody Sequences of the Heavy and Light Chains

Several of the exemplary monoclonal antibodies that bind to the 1-e loop of AMA-1 (SEQ ID NO: 1), and the polymorphic face of domain III of AMA-1 (SEQ ID NO: 2) were sequenced to determine their Heavy and Light Chain Sequences. Three monoclonal antibodies that bind the 1e-loop were sequenced, monoclonal antibodies 1B10, 4E11 and 4E8, the results summarized in the Table 2 below. One monoclonal antibody that binds the polymorphic face of domain III was sequenced, the results summarized in Table 2 for monoclonal antibody 1E10.

Sample Preparation:

Total RNA was isolated from the hybridoma cell line culture ($2 \times 10^6$ cells). RNA was treated to remove aberrant transcripts and reverse transcribed using oligo(dT) primers. Samples of the resulting cDNA were amplified in separate PCRs using framework land constant region primer pairs specific for either the heavy or light chain. Reaction products were separated on an agarose gel, size-evaluated and recovered. In some cases, a second, nested PCR is performed to increase yield of the desired fragment(s) Amplicons were cloned into a vector using the TA cloning strategy. 12 colonies were selected and plasmid DNA was amplified using primers specific for vector DNA sequences. PCR product size for each cloned insert was evaluated by gel electrophoresis, and 6 reactions were prepared for sequencing using a PCR clean up kit and sequenced using cycle sequencing with fluorescent dye terminators and capillary-based electrophoresis.

Sequence Analysis

DNA sequence data from all constructs are analyzed and consensus sequences for heavy and light chain are determined. The consensus sequences are compared to known variable region sequences to rule out artifacts and/or process contamination. Consensus sequences are then analyzed using an online tool to verify that the sequences could encode a productive immunoglobulin.

TABLE 2

Summary of Antibody Sequences

| Antibody Reference Sequence | Sequence |
|---|---|
| Monoclonal 1B10 Heavy Chain ($V_H$) DNA Sequence (SEQ ID NO. 25) | gaggtgcagctgcaggagtctggacctggcctagtgcggccctcacagagcctgtccatcacc tgcacagtctctggtttctcattacctctctatggtgttcactgggttcgccagtctccaggaaagg gtctggagtggctgggagtcatatggagtgggggaagcacagactataatgcagctttcgtctc cagactgagcatcagcaaggacaattccaagagccaagttttattgaaatgaacagtctgcaag ctgatgacacagccacatattactgtgccagaaataatggttactacgttgatgctatggactattg gggtcaaggaacctcagtcaccgtctcctcagccaaaacaacacc |
| Monoclonal 1B10 Heavy Chain ($V_H$) Protein Sequence (SEQ ID NO: 26) | Complementarity determining regions (CDRs) are bold. EVQLQESGPGLVQPSQSLSITCTVSGFSLNMYGVHWVRQSP GKGLEWLGVIWSGGTTDYNAAFISRLSINRDNSKSQVFFKM NSLQTDDTAIYYCVRNNGYYVDAMDYWGQGTSVAVSSAK |
| Monoclonal 1B10 $V_H$ CDR1 ((SEQ ID NO: 27) | GFSLNMYG |
| Monoclonal 1B10 $V_H$ CDR2 (SEQ ID NO: 28) | IWSGGTT |
| Monoclonal 1B10 $V_H$CDR3 (SEQ ID NO: 29) | VRNNGYYVDAMDY |
| Monoclonal 1B10 Light Chain ($V_L$) DNA Sequence (SEQ ID NO: 30) | gatgttgtgatgacccagactccactctccctgcctgtcagtcttggagatcaagcctccatctctt gcagatctagtcagagccttgtacacagtaatggcaacacctatttacattggtacctgcagagg ccaggccagtctccaaagctcctgatctacaaagtttccaaccgattttctgggtcccagacag gttcagtggcagtggatcggggacagatttcacactcaagatcagcagagtggaggctgagga tctgggagtttatttctgctctcagagtacacttggtcccacgttcggaggggggaccaagagg aaatgcaacgggctgatg |

TABLE 2-continued

Summary of Antibody Sequences

| Antibody Reference Sequence | Sequence |
| --- | --- |
| Monoclonal 1B10 Light Chain (V$_L$) Protein Sequence (SEQ ID NO: 31) | Complementarity determining regions (CDRs) are bold.<br>DVVMTQTPLSLPVSLGDQASISCRSSQSLVHSNGNTYLHWY<br>LQRPGQSPKLLIYKVSNRFSGVPDRFSGSGSGTDFTLKISRVE<br>AEDLGVYFCSQSTLGPTFGGGTKLEMQRAD |
| Monoclonal 1B10 V$_L$ CDR1 (SEQ ID NO: 32) | QSLVHSNGNTY |
| Monoclonal 1B10 V$_L$ CDR2 (SEQ ID NO: 33) | KVS |
| Monoclonal 1B10 V$_L$CDR3 (SEQ ID NO: 34) | SQSTLGPT |
| Monoclonal 4E11 Heavy Chain (V$_H$) DNA Sequence (SEQ ID NO: 35) | gaggtgcagctgcaggagtctggacctggcctagtgcggccctcacagagcctgtccatcacc<br>tgcacagtctctggtttctcattacctctctatggtgttcactgggttcgccagtctccaggaaagg<br>gtctggagtggctgggagtcatatggagtgggggaagcacagactataatgcagctttcgtctc<br>cagactgagcatcagcaaggacaattccaagagccaagtttttattgaaatgaacagtctgcaag<br>ctgatgacacagccacatattactgtgccagaaataatggttactacgttgatgctatggactattg<br>gggtcaaggaacctcagtcaccgtctcctcagccaaaacaacacc |
| Monoclonal 4E11 Heavy Chain (V$_H$) Protein Sequence (SEQ ID NO: 36) | Complementarity determining regions (CDRs) are bold.<br>EVQLQESGPGLVRPSQSLSITCTVSGFSLPLYGVHWVRQSPG<br>KGLEWLGVIWSGGSTDYNAAFVSRLSISKDNSKSQVFFEMN<br>SLQADDTATYYCARNNGYYVDAMDYWGQGTSVTVSSAKT<br>T |
| Monoclonal 4E11 V$_H$ CDR1 (SEQ ID NO: 37) | GFSLPLYG |
| Monoclonal 4E11 V$_H$ CDR2 (SEQ ID NO: 38) | IWSGGST |
| Monoclonal 4E11 V$_H$ CDR3 (SEQ ID NO: 39) | ARNNGYYVDAMDY |
| Monoclonal 4E11 Light Chain (V$_L$) DNA Sequence (SEQ ID NO: 40) | gatgttgtgatgacccaaactccactctccctgcctgtcagtatggagatcaagcctccatctat<br>gcagatctagtcagagccttgtacacagtaatggaaacacctatttacattggtacctgcagaagc<br>caggccagtctccaaagctcctgatcttcaaagttttccaaccgattttctggggtcccagacaggt<br>tcagtggcagtggatcagggacagatttcacactccagatcagcagagtggaggctgaggatct<br>gggattttatttctgatcgcaaagtacacatgttcccacgttcggaggggggaccaaactggaaa<br>taaaacgggct |
| Monoclonal 4E11 Light Chain (V$_L$) Protein Sequence (SEQ ID NO: 41) | Complementarity determining regions (CDRs) are bold<br>DVVMTQTPLSLPVSLGDQASISCRSSQSLVHSNGNTYLHWY<br>LQKPGQSPKLLIFKVSNRFSGVPDRFSGSGSGTDFTLQISRVE<br>AEDLGFYFCSQSTHVPTFGGGTKLEIKRA |
| Monoclonal 4E11 V$_L$ CDR1 (SEQ ID NO: 42) | QSLVHSNGNTY |
| Monoclonal 4E11 V$_L$ CDR2 (SEQ ID NO: 43) | KVS |
| Monoclonal 4E11 V$_L$ CDR3 (SEQ ID NO: 44) | SQSTHVPT |
| Monoclonal 4E8 Heavy Chain (V$_H$) DNA Sequence (SEQ ID NO: 45) | gaggtgcagctgcaggagtctggacctggcctggtgcagccctcacagagcctgtccatcacc<br>tgcacagtctctgatttctcattaattatgtatggtgtacattgggttcgccagtctccgggaaaggg<br>tctggagtggctgggagtgatatggagtggtggaagcacagactataatgcagctttcatatcca<br>gactgagcatcagcaaggacaattccaagagccaagttttctttaaaatgaacagtctgcaagct<br>gatgacacagccatatattactgtgccagaaataatggttactacgttgatgctatggactactgg<br>ggtcaaggaacctcagtcaccgtctcctcagccaaaa |
| Monoclonal 4E8 Heavy Chain (V$_H$) Protein Sequence (SEQ ID NO: 46) | Complementarity determining regions (CDRs) are bold<br>EVQLQESGPGLVQPSQSLSITCTVSDFSLIMYGVHWVRQSPG<br>KGLEWLGVIWSGGSTDYNAAFISRLSISKDNSKSQVFFKMN<br>SLQADDTAIYYCARNNGYYVDAMDYWGQGTSVTVSSAK |
| Monoclonal 4E8 V$_H$ CDR1 (SEQ ID NO: 47) | DFSLIMYG |
| Monoclonal 4E8 V$_H$ CDR2 (SEQ ID NO: 48) | IWSGGST |

TABLE 2-continued

Summary of Antibody Sequences

| Antibody Reference Sequence | Sequence |
|---|---|
| Monoclonal 4E8 $V_H$ CDR3 (SEQ ID NO: 49) | ARNNGYYVDAMDY |
| Monoclonal 4E8 Light Chain ($V_L$) DNA Sequence (SEQ ID NO: 50) | gatgttgtgatgacccaaactccactctccctgcctgtcagtcttggagatcaagcctccatctctt gcagatctagtcagagccttgtacacaataatggaaacacctatttacattggtacctgcagaagc caggccagtctccaaagctcctgatctacaaagtttccaaccgattttttggggtcccagacaggt tcagtggcagtggatcagggacagatttcacactcaagatcagcagagtggaggctgaggatct gggagtttattctgctctcaaagtacacatgttcccacgttcggaggggggaccaagctggaaa tcaaacgtaagtcg |
| Monoclonal 4E8 Light Chain ($V_L$) Protein Sequence (SEQ ID NO: 51) | Complementarity determining regions (CDRs) are bold. DVVMTQTPLSLPVSLGDQASISCRSSQSLVHNNGNTYLHWY LQKPGQSPKLLIYKVSNRFFGVPDRFSGSGSGTDFTLKISRVE AEDLGVYFCSQSTHVPTFGGGTKLEIKRKS |
| Monoclonal 4E8 $V_L$ CDR1 (SEQ ID NO: 52) | QSLVHNNGNTY |
| Monoclonal 4E8 $V_L$ CDR2 (SEQ ID NO: 53) | KVS |
| Monoclonal 4E8 $V_L$ CDR4 (SEQ ID NO: 54) | SQSTHVPT |
| Monoclonal 1E10 Heavy Chain ($V_H$) DNA sequence (SEQ ID NO: 55) | gaggtgcagctgcaggagtctggggctgaattggcaaaacctggggcctcagtgaagctgtcc tgcaaggatctggctcacctttactaactacttgatgcactggataaaacaaaggcctggacg gtctggaatggattggatacattaatcatgggcagtggttatactaactacaatcagaagttcattga cagggccacattgactgcagacaaatcctccagcacagcctacatgcagctgcgcagctacat atgaggactctgcagtctattactgtgtccagggtacttcgatgtctggggcacagggaccacg gtcaccgtctcctcagccaaaacgacacccccatctgtctatccactggccc |
| Monoclonal 1E10 Heavy Chain ($V_H$) Protein Sequence (SEQ ID NO: 56) | Complementarity determining regions (CDRs) are bold. EVQLQESGAELAKPGASVKLSCKASGYTFTNYLMHWIKQR PGQGLEWIGYINHGSGYTNYNQKFIDRATLTADKSSSTAYM QLRSLTYEDSAVYYCVHGYFDVWGTGTTVTVSSAKTTPPSV YPLA |
| Monoclonal 1E10 $V_H$ CDR1 (SEQ ID NO: 57) | GYTFTNYL |
| Monoclonal 1E10 $V_H$ CDR2 (SEQ ID NO: 58) | INHGSGYT |
| Monoclonal 1E10 $V_H$ CDR3 (SEQ ID NO: 59) | VHGYFDV |
| Monoclonal 1E10 Light Chain ($V_L$) DNA sequence (SEQ ID NO: 60) | caagtgcagattttcagatcctgctaatcagtgcctcagtcatactgtccagaggacaaattgttct cacccagtctccaacaatcatgtctgcatctccaggggagaaggtcaccatgacctgcagtgcc agctcaagtgtaacttacatgcactggtaccagcagaagccaggcacctcccccaaaagatgg atttatgacacatccaaactggcctctggagtccctgctcgcttcagtggcagtgggtctgggac ctcttattctctcacaatcagcagcatggaggctgaagatgctgccacttattactgccatcagcg gagtagttaccccacgttcggaggggggaccaagctggaaatcaaacgtaagtcgactgcacc a |
| Monoclonal 1E10 Light Chain ($V_L$) Protein sequence (SEQ ID NO: 61) | Complementarity determining regions (CDRs) are bold QVQIFSFLLISASVILSRGQIVLTQSPTIMSASPGEKVTMTCSA SSSVTYMHWYQQKPGTSPKRWIYDTSKLASGVPARFSGSGS GTSYSLTISSMEAEDAATYYCHQRSSYPTFGGGTKLEIKRKS TAP |
| Monoclonal 1E10 $V_L$ CDR1 (SEQ ID NO: 62) | SSSVTY |
| Monoclonal 1E10 $V_L$ CDR2 (SEQ ID NO: 63) | DTS |
| Monoclonal 1E10 $V_L$ CDR3 (SEQ ID NO: 64) | HQRSSYPT |

REFERENCES

1. Sachs J, Malaney P (2002) The economic and social burden of malaria. Nature 415: 680-685.
2. Haynes J D, Moch J K, Smoot D S (2002) Erythrocytic malaria growth or invasion inhibition assays with emphasis on suspension culture GIA. Methods Mol Med 72: 535-554.
3. Drew D R, Hodder A N, Wilson D W, Foley M, Mueller I, et al. (2012) Defining the Antigenic Diversity of *Plasmodium falciparum* Apical Membrane Antigen 1 and the Requirements for a Multi-Allele Vaccine against Malaria. PLoS One 7: e51023.
4. Malkin E M, Diemert D J, McArthur J H, Perreault J R, Miles A P, et al. (2005) Phase 1 clinical trial of apical membrane antigen 1: an asexual blood-stage vaccine for *Plasmodium falciparum* malaria. Infect Immun 73: 3677-3685.
5. Persson K E, Lee C T, Marsh K, Beeson J G (2006) Development and optimization of high-throughput methods to measure *Plasmodium falciparum*-specific growth inhibitory antibodies. J Clin Microbiol 44: 1665-1673.
6. Chesne-Seck M L, Pizarro J C, Vulliez-Le Normand B, Collins C R, Blackman M J, et al. (2005) Structural comparison of apical membrane antigen 1 orthologues and paralogues in apicomplexan parasites. Mol Biochem Parasitol 144: 55-67.
7. Crawford J, Tonkin M L, Grujic O, Boulanger M J (2010) Structural characterization of apical membrane antigen 1 (AMA1) from *Toxoplasma gondii*. J Biol Chem 285: 15644-15652.
8. Hodder A N, Crewther P E, Matthew M L, Reid G E, Moritz R L, et al. (1996) The disulfide bond structure of *Plasmodium* apical membrane antigen-1. J Biol Chem 271: 29446-29452.
9. Bai T, Becker M, Gupta A, Strike P, Murphy V J, et al. (2005) Structure of AMA1 from *Plasmodium falciparum* reveals a clustering of polymorphisms that surround a conserved hydrophobic pocket. Proc Natl Acad Sci USA 102: 12736-12741.
10. Collins C R, Withers-Martinez C, Bentley G A, Batchelor A H, Thomas A W, et al. (2007) Fine mapping of an epitope recognized by an invasion-inhibitory monoclonal antibody on the malaria vaccine candidate apical membrane antigen 1. J Biol Chem 282: 7431-7441.
11. Coley A M, Gupta A, Murphy V J, Bai T, Kim H, et al. (2007) Structure of the malaria antigen AMA1 in complex with a growth-inhibitory antibody. PLoS Pathog 3: 1308-1319.
12. Cao J, Kaneko O, Thongkukiatkul A, Tachibana M, Otsuki H, et al. (2009) Rhoptry neck protein RON2 forms a complex with microneme protein AMA1 in *Plasmodium falciparum* merozoites. Parasitol Int 58: 29-35.
13. Tonkin M L, Rogues M, Lamarque M H, Pugniere M, Douguet D, et al. (2011) Host cell invasion by apicomplexan parasites: insights from the co-structure of AMA1 with a RON2 peptide. Science 333: 463-467.
14. Collins C R, Withers-Martinez C, Hackett F, Blackman M J (2009) An inhibitory antibody blocks interactions between components of the malarial invasion machinery. PLoS Pathog 5: e1000273.
15. Howell S A, Withers-Martinez C, Kocken C H, Thomas A W, Blackman M J (2001) Proteolytic processing and primary structure of *Plasmodium falciparum* apical membrane antigen-1. J Biol Chem 276: 31311-31320.
16. Dutta S, Haynes J D, Barbosa A, Ware L A, Snavely J D, et al. (2005) Mode of action of invasion-inhibitory antibodies directed against apical membrane antigen 1 of *Plasmodium falciparum*. Infect Immun 73: 2116-2122.
17. Woehlbier U, Epp C, Hackett F, Blackman M J, Bujard H (2010) Antibodies against multiple merozoite surface antigens of the human malaria parasite *Plasmodium falciparum* inhibit parasite maturation and red blood cell invasion. Malar J 9: 77.
18. Howell S A, Hackett F, Jongco A M, Withers-Martinez C, Kim K, et al. (2005) Distinct mechanisms govern proteolytic shedding of a key invasion protein in apicomplexan pathogens. Mol Microbiol 57: 1342-1356.
19. Howell S A, Well I, Fleck S L, Kettleborough C, Collins C R, et al. (2003) A single malaria merozoite serine protease mediates shedding of multiple surface proteins by juxtamembrane cleavage. J Biol Chem 278: 23890-23898.
20. Williams A R, Douglas A D, Miura K, Illingworth J J, Choudhary P, et al. (2012) Enhancing blockade of *Plasmodium falciparum* erythrocyte invasion: assessing combinations of antibodies against PfRH5 and other merozoite antigens. PLoS Pathog 8: e1002991.
21. Bliss C I (1939) The Toxicity of Poisons Applied Jointly. Annals of Applied Biology 26: 25.
22. Lalitha P V, Ware L A, Barbosa A, Dutta S, Moch J K, et al. (2004) Production of the subdomains of the *Plasmodium falciparum* apical membrane antigen 1 ectodomain and analysis of the immune response. Infect Immun 72: 4464-4470.
23. Pizarro J C, Vulliez-Le Normand B, Chesne-Seck M L, Collins C R, Withers-Martinez C, et al. (2005) Crystal structure of the malaria vaccine candidate apical membrane antigen 1. Science 308: 408-411.
24. Dutta S, Lalitha P V, Ware L A, Barbosa A, Moch J K, et al. (2002) Purification, characterization, and immunogenicity of the refolded ectodomain of the *Plasmodium falciparum* apical membrane antigen 1 expressed in *Escherichia coli*. Infect Immun 70: 3101-3110.
25. Wilson D W, Crabb B S, Beeson J G (2010) Development of fluorescent *Plasmodium falciparum* for in vitro growth inhibition assays. Malar J 9: 152.
26. Kocken C H, van der Wel A M, Dubbeld M A, Narum D L, van de Rijke F M, et al. (1998) Precise timing of expression of a *Plasmodium falciparum*-derived transgene in *Plasmodium berghei* is a critical determinant of subsequent subcellular localization. J Biol Chem 273: 15119-15124.
27. Coley A M, Parisi K, Masciantonio R, Hoeck J, Casey J L, et al. (2006) The most polymorphic residue on *Plasmodium falciparum* apical membrane antigen 1 determines binding of an invasion-inhibitory antibody. Infect Immun 74: 2628-2636.
28. Dutta S, Haynes J D, Moch J K, Barbosa A, Lanar D E (2003) Invasion-inhibitory antibodies inhibit proteolytic processing of apical membrane antigen 1 of *Plasmodium falciparum* merozoites. Proc Natl Acad Sci USA 100: 12295-12300.

We claim:

1. An isolated antibody that specifically binds to the 1e-loop region of Apical Membrane Antigen-1 (AMA-1) or an antigen binding fragment thereof comprising complementary determining regions (CDRs) 1, 2 and 3 of a heavy chain variable region and complementary determining regions (CDRs) 1, 2 and 3 of a light chain variable region selected from the group:
   heavy chain SEQ ID NO. 27 (CDR1), SEQ ID NO 28 (CDR2) and SEQ ID NO 29 (CDR3); and light chain SEQ ID NO. 32 (CDR1), SEQ ID NO 33 (CDR2) and SEQ ID NO 34 (CDR3);
   heavy chain SEQ ID NO. 37 (CDR1), SEQ ID NO. 38 (CDR2) and SEQ ID NO: 39 (CDR3); and light chain SEQ ID NO. 42 (CDR1), SEQ ID NO. 43 (CDR2) and SEQ ID NO: 44 (CDR3); and
   heavy chain SEQ ID NO. 47 (CDR1), SEQ ID NO. 48 (CDR2) and SEQ ID NO. 49 (CDR3); and light chain SEQ ID NO. 52 (CDR1), SEQ ID NO. 53 (CDR2) and SEQ ID NO. 54 (CDR3);
   wherein the antibody or an antigen binding fragment thereof recognizes an epitope of about 5 to about 11 amino acids of SEQ ID NO: 1.

2. The isolated antibody, or antigen binding fragment thereof, of claim 1 that specifically binds to an epitope consisting of SEQ ID NO: 1.

3. The isolated antibody, or antigen binding fragment thereof, of claim 1 that inhibits the binding of AMA-1 to rhoptry neck protein RON2.

4. The isolated antibody, or antigen binding fragment thereof, of claim 1 comprising a heavy chain variable region ($V_H$) sequence and light chain variable region ($V_L$) sequence that are selected from the group:
   SEQ ID NO: 26 ($V_H$) and SEQ ID NO: 31 ($V_L$);
   SEQ ID NO: 36 ($V_H$) and SEQ ID NO: 41 ($V_L$); and
   SEQ ID NO: 46 ($V_H$) and SEQ ID NO: 51 ($V_L$).

5. An isolated antibody or an antigen binding fragment thereof comprising complementary determining regions (CDRs) 1, 2 and 3 of a heavy chain variable region of:
   SEQ ID NO. 57 (CDR1), SEQ ID NO 58 (CDR2), and SEQ ID NO 59 (CDR3); and complementary determining regions (CDRs) 1, 2 and 3 of a light chain variable region of:
   SEQ ID NO. 62 (CDR1), SEQ ID NO 63 (CDR2) and SEQ ID NO 64 (CDR3);
   wherein the antibody or antigen binding fragment thereof specifically binds to domain III of AMA-1 and recognizes an epitope of about 5 to about 17 amino acids of SEQ ID NO:2.

6. The isolated antibody, or antigen binding fragment thereof, of claim 5, that specifically binds to an epitope consisting of about 8 to about 17 amino acids of SEQ ID NO:2.

7. The isolated antibody, or antigen binding fragment thereof, of claim 5 that inhibits the proteolytic processing of AMA-1 within a cell infected with P. falciparum.

8. The isolated antibody, or antigen binding fragment thereof, of claim 5 comprising a heavy chain variable region ($V_H$) sequence of SEQ ID NO: 56 and a light chain variable region ($V_L$) sequence of SEQ ID NO. 61.

9. A composition comprising (i) at least one isolated antibody or antigen binding fragment thereof that specifically binds to the 1e-loop region of Apical Membrane Antigen-1 (AMA-1), comprising complementary determining regions (CDRs) 1, 2 and 3 of a heavy chain variable region and complementary determining regions (CDRs) 1, 2 and 3 of a light chain variable region selected from the group:
   heavy chain SEQ ID NO. 27 (CDR1), SEQ ID NO 28 (CDR2) and SEQ ID NO 29 (CDR3); and light chain SEQ ID NO. 32 (CDR1), SEQ ID NO 33 (CDR2) and SEQ ID NO 34 (CDR3);
   heavy chain SEQ ID NO. 37 (CDR1), SEQ ID NO. 38 (CDR2) and SEQ ID NO: 39 (CDR3); and light chain SEQ ID NO. 42 (CDR1), SEQ ID NO. 43 (CDR2) and SEQ ID NO: 44 (CDR3); and
   heavy chain SEQ ID NO. 47 (CDR1), SEQ ID NO. 48 (CDR2) and SEQ ID NO. 49 (CDR3); and light chain SEQ ID NO. 52 (CDR1), SEQ ID NO. 53 (CDR2) and SEQ ID NO. 54 (CDR3); and
   (ii) at least one isolated antibody or antigen binding fragment thereof that specifically binds to domain III of AMA-1, comprising complementary determining regions (CDRs) 1, 2 and 3 of a heavy chain variable region of:
   SEQ ID NO. 57 (CDR1), SEQ ID NO 58 (CDR2), and SEQ ID NO 59 (CDR3); and complementary determining regions (CDRs) 1, 2 and 3 of a light chain variable region of:
   SEQ ID NO. 62 (CDR1), SEQ ID NO 63 (CDR2) and SEQ ID NO 64 (CDR3).

10. A method of treating malaria comprising administering an effective amount of the isolated antibody, or an antigen binding fragment thereof, of claim 1.

11. A method of treating malaria comprising administering an effective amount of the isolated antibody, or an antigen binding fragment thereof, of claim 5.

12. A method of treating malaria comprising administering an effective amount of the composition of claim 9.

* * * * *